(12) United States Patent
Kumar-Singh et al.

(10) Patent No.: US 8,324,182 B2
(45) Date of Patent: Dec. 4, 2012

(54) HUMANIZED MODEL OF MEMBRANE ATTACK COMPLEX (MAC) FORMATION ON MURINE RETINA AND COMPOSITIONS, KITS AND METHODS FOR TREATMENT OF MACULAR DEGENERATION

(75) Inventors: Rajendra Kumar-Singh, Boston, MA (US); Siobhan M Cashman, Boston, MA (US); Kasmir Ramo, Cambridge, MA (US)

(73) Assignee: Tufts University, Boston, MA (US)

( * ) Notice: Subject to any disclaimer, the term of this patent is extended or adjusted under 35 U.S.C. 154(b) by 54 days.

(21) Appl. No.: 12/867,566

(22) PCT Filed: Feb. 13, 2009

(86) PCT No.: PCT/US2009/000947
§ 371 (c)(1),
(2), (4) Date: Aug. 13, 2010

(87) PCT Pub. No.: WO2009/102488
PCT Pub. Date: Aug. 20, 2009

(65) Prior Publication Data
US 2011/0015136 A1 Jan. 20, 2011

Related U.S. Application Data

(60) Provisional application No. 61/070,650, filed on Mar. 25, 2008, provisional application No. 61/066,288, filed on Feb. 19, 2008, provisional application No. 61/066,062, filed on Feb. 15, 2008.

(51) Int. Cl.
*A61K 48/00* (2006.01)
*A01N 61/00* (2006.01)
(52) U.S. Cl. .................................. 514/44 R; 514/1
(58) Field of Classification Search ............... 514/44 R, 514/1
See application file for complete search history.

(56) References Cited

U.S. PATENT DOCUMENTS

| 4,405,712 A | 9/1983 | Vande Woude et al. |
| 4,650,764 A | 3/1987 | Temin et al. |
| 4,797,368 A | 1/1989 | Carter et al. |
| 4,861,719 A | 8/1989 | Miller |
| 4,980,289 A | 12/1990 | Temin et al. |
| 5,112,767 A | 5/1992 | Roy-Burman et al. |
| 5,122,767 A | 6/1992 | Cameron et al. |
| 5,124,263 A | 6/1992 | Temin et al. |
| 5,139,941 A | 8/1992 | Muzyczka et al. |
| 5,624,837 A | 4/1997 | Fodor et al. |
| 5,998,208 A | 12/1999 | Fraefel et al. |
| 7,166,568 B1 | 1/2007 | Sims |
| 7,235,391 B2 | 6/2007 | Wu et al. |
| 7,309,487 B2 | 12/2007 | Inana et al. |
| 2003/0086940 A1 | 5/2003 | Costa et al. |
| 2005/0265995 A1 | 12/2005 | Tomlinson et al. |
| 2006/0263819 A1 | 11/2006 | Hageman et al. |
| 2007/0093443 A1 | 4/2007 | Madison et al. |
| 2007/0196367 A1 | 8/2007 | Dinu |
| 2007/0203190 A1 | 8/2007 | Patil et al. |
| 2008/0267980 A1 | 10/2008 | Tomlinson et al. |
| 2010/0120665 A1 | 5/2010 | Kaleko et al. |

FOREIGN PATENT DOCUMENTS

| EP | 0338841 B1 | 3/1995 |
| WO | WO85/05629 A1 | 12/1985 |
| WO | WO87/04462 A1 | 7/1987 |
| WO | WO89/01036 A1 | 2/1989 |
| WO | WO89/07150 A1 | 8/1989 |
| WO | WO90/02797 A1 | 3/1990 |
| WO | WO90/02806 A1 | 3/1990 |
| WO | WO90/13641 A1 | 11/1990 |
| WO | WO92/05266 A2 | 4/1992 |
| WO | WO92/07943 A1 | 5/1992 |
| WO | WO92/14829 A1 | 9/1992 |
| WO | WO93/14188 A1 | 7/1993 |
| WO | WO97/17987 A1 | 5/1997 |

OTHER PUBLICATIONS

Han et al. Investigative Ophthalmology and Visual Science 52(6):3051-3059, 2001.*
Tatusova et al. "Blast 2 Sequences, a new tool for comparing protein and nucleotide sequences" FEMS Microbiol Lett. 1999, vol. 174, pp. 247-250.
Thompson et al. "Clustal W: improving the sensitivity of progressive multiple sequence alignment through sequence weighting, position-specific gap penalities and weight matrix choice" Nucl Acid Res, 1994, vol. 22, pp. 4673-4680.
Tomkinson et al. "Epstein-Barr Virus Recombinants from Overlapping Cosmid Fragments" J Virol, 1993, vol. 67, pp. 7298-7306.
Tratschin et al. "A Human Parvovirus, Adeno-Associated Virus, as a Eucaryotic Vector: Transient Expression and Encapsidation of the Procaryotic Gene for Chloramphenicol Acetyltransferase" Mol Cellul Biol, 1984, vol. 4, pp. 2072-2081.
Tratschin et al. "Adeno-Associated Virus Vector for High-Frequency Integration, Expression, and Rescue of Genes in Mammalian Cells" Mol Cellul Biol, 1985, vol. 5, pp. 3251-3260.

(Continued)

*Primary Examiner* — Marcia S Noble
(74) *Attorney, Agent, or Firm* — Lawson & Weitzen, LLP; Sonia K. Guterman; Teofilo Javier, Jr.

(57) ABSTRACT

Methods and compositions for treating a subject having age-related macular degeneration (AMD), methods of assaying human macular degeneration (MD), and methods and kits for assaying potential therapeutic agents for treatment of human MD are provided herein.

15 Claims, 34 Drawing Sheets

OTHER PUBLICATIONS

Urlaub et al. "Isolation of Chinese hamster cell mutants deficient in dihydrofolate reductase activity" Proc Natl Acad Sci, 1980, vol. 77, pp. 4216-4220.

van Leeuwen et al. "Epodemilogy of age-related maculopath: a review" Eur J Epidemoil, 2003, vol. 18, pp. 845-854.

van Zijl et al. "Regeneration of Herpesviruses from Molecularly Cloned Subgenomic Fragments" J Virol, 1998, vol. 62, pp. 2191-2195.

Venkateswaran et al. "Production of Anti-Fibroblast Growth Factor Receptor Monoclonal Antibodies by in Vitro Immunization" Hybridoma, 1992, vol. 11, pp. 729-739.

Walsh et al. "Phenotypic Correction of Fanconi Anemia in Human Hematopoietic Cells with a Recombinant Adeno-associated Virus Vector" J Clin Investig, 1994, vol. 94, pp. 1440-1448.

Yu et al. "Mapping the Active Site of CD59" J Exp Med, 1997, vol. 185, pp. 745-753.

Zhou et al. "Adeno-associated virus-2 mediated gene transfer in murine hematopoietic progenitor cells" Exper Hematol, 1993, vol. 21, pp. 928-933.

Zuffrey et al. "Multiply attenuated lentiviral vector achieves efficient gene delivery in vivo" Nat Biotechnol, 1997, vol. 15, pp. 871-875.

Anderson et al. "A Role for Local Inflammation in the Formation of Drusen in the Aging Eye" J Ophthalmol, 2002, pp. 411-431, vol. 134.

Cohen et al. "Generation of varicella-zoster virus (VZV) and viral mutants from cosmid DNAs: VZV thymidylate synthetase is not essential for replication in vitro" Proc Natl Acad, vol. 90, pp. 7376-7380.

Cosset et al. "A New Avian Leukosis Virus-Based Packaging Cell Line That Uses Two Seperate Transcomplementing Helper Genomes" J Virol, 1990, vol. 64, pp. 1070-1078.

Cunningham et al. "A cosmid-based system for constructing mutants of herpes simplex virus type 1" Virol, 1993, vol. 197, pp. 116-124.

Davies et al. "CD59, An LY-6-like protein expressed in human lymphoid cells, regulates the action of the complement membrane attack complex on homologous cells" J Exp Med, 1989, vol. 170, pp. 637-654.

Dull et al. "A Third-Generation Lentivirus Vector with a Conditional Packaging System" J Virol, 1998, vol. 72, pp. 8463-8471.

Edwards et al. "Complement Factor H Polymorphism and Age-Related Macular Degeneration" Science, 2005, vol. 308, pp. 421-424.

Eglitis et al. "Retroviral vectors for introduction of genes into Mammalian cells" BioTechniques, 1988, vol. 6, No. 7, pp. 608-614.

Evans et al. "High efficiency vectors for cosmid microcloning and genomic analysis" Gene, 1989, vol. 79, pp. 9-20.

Flotte et al. "Gene expressions from Adeno-associated virus vectors in airway epithellal cells" Am J Respir Cell Mol Biol, 1992, vol. 7, pp. 349-356.

Graham et al. "Charasterisitics of a human cell transformed by DNA from human adenovirus Type 5" J Gen Cirol, 1977, vol. 36, pp. 59-72.

Graham et al. "Chapter 11 Manipulation of Adenovirus Vectors in Methods" in Methods in Molecular Biology, vol. 7: Gene Transfer and Expression Protocols, Ed by E.J. Murray, 1991, pp. 109-128; The Humama Press Inc.: Clinton, NJ.

Hageman et al. "A Common haplotype in the complement regulatory gene factor H (HF1/CFH) prediposes individuals to age-related macular degeneration" Proc Natl Acad Sci, 2005, vol. 102, pp. 7227-7232.

Haines et al. "Complement Factor H Variant Increases the Risk of Age-Related Macular Degeneration" Science, 2005, vol. 308, pp. 419-421.

Hamilton et al. "Regulatory Control of the Terminal Complement Proteins at the Surface of Human Endothelial Cells: Neutralization of a C5b-9 Inhibitor by Antibody to CD59" Blood, 1990, vol. 76, No. 12, pp. 2572-2577.

Harada et al. "Monocional antibody G6K12 specific for membrane-associated differentation marker of human stratified squamous epithelia and squamous cell carcinoma" J Oral Pathol Med, vol. 22, pp. 145-152.

Holguin et al. "Isolation and Characterization of a Membrane Protein from Normal Human Erythrocytes That Inhibits Reactive Lysis of the Erythrocytes of Paroxysmal Nocturnal Hemoglobinuria" J Clin Investig Inc, 1989, vol. 84, pp. 7-17.

Inai et al. "Immunohistochemical detection of an enamel protein-related epitope in rat bone at an early stage of osteogenesis" Histochemistry, 1993, vol. 99, pp. 355-362.

Johnson et al. "A Potential Rule for Immune Complex Pathogenesis in Drusen Formation" Exp Eye Res, 2000, vol. 70, pp. 441-449.

Kafri et al. "Sustained expression of genes delivered directly into liver and muscle by lentiviral vectors" Nat Genet, 1997, vol. 17, pp. 314-317.

Kaplitt et al. "Long-term gene expression and phenotypic correction using adeno-associated virus vectors in the mammalian brain" Nat Genet, 1994, vol. 8, pp. 148-154.

Kaufman et al. "Amplification and Expression of Sequences Contransfected with a Modular Dihydrofolate Reductase Complementary DNA Gene" J Mol Biol, 1982, vol. 159, pp. 601-621.

Klein et al. "Complement Factor H Polymorphism in Age-Related Macular Degeneration" Science, 2005, vol. 308, pp. 385-389.

Klein et al. "Fifteen-year cumulative incidence of age-related macular degeneration" Ophthalmology, 2007, vol. 114, pp. 253-262.

Korman et al. "Expression of human class II major histocompatibility complex antigens using retrovirus cectors" Proc Natl Acad Sci, 1987, vol. 84, pp. 2150-2154.

Leface et al. "Gene Transfer into Hematopoietic Progenitor Cells Mediated by an Adeno-Associated Virus Vector" Virol, 1988, vol. 162, pp. 483-486.

Laughlin et al. "Latent Infection of KB Cells with Adeno-Associated Virus Type 2" J Virol, 1986, vol. 60, pp. 515-524.

Lebkowski et al. "Adeno-Associated Virus: a Vector System for Efficient Introduction and Integration of DNA into a Variety of Mammalian Cell Types" Mol Cell Biol, 1988, vol. 8, pp. 3988-3996.

Levrero et al. "Defective and nondefective adenovirus vectors for expressing foreign genes in vitro and in vivo" Gene, 1991, vol. 101, pp. 195-202.

Markowitz et al. "A Safe Packaging Line for Gene Transfer: Separating Viral Genes on Two Different Piasmids" J Virol, 1988, vol. 62, pp. 1120-1124.

McLauglin et al. "Adeno-Associated Virus General Transduction Vectors: Analysis of Proviral Structures" J Virol, 1988, vol. 62, pp. 1963-1973.

Miller et al. "Redesign of Retrovirus Packaging Cell Lines To Avoid Recombination Leading to Helper Virus Production" Mol Cell Biol, vol. 6, pp. 2895-2902.

Miller et al. "Improved Retroviral Vectors for Gene Transfer and Expression" Biotechniques, 1989, vol. 7, pp. 980-990.

Morgenstern et al. "Advanced mammalian gene transfer: high titre retroviral vectors with multiple drug selection markers and a complementary helper-free packaging cell line" Nucl Acid Res, 1990, vol. 18, pp. 3587-3596.

Morgenstern et al. "DIALIGN: Finding local similarities by multiple sequence alignment" Bioinformatics, 1998, vol. 14, pp. 290-294.

Mulder et al. "Characterization of two human monoclonal antibodies reactive with HLA-B12 and HLA-B60, respectively, raised by in vitro secondary immunization of peripheral blood lymphocytes" Hum Immunol, 1993, vol. 36, pp. 186-192.

Muzyczka et al. "Use of Adeno-Associated Virus as a General Transduction Vector for Mammalian Cells" Curr Top Microbiol Immunol, 1992, vol. 158, pp. 97-129.

Naldini et al. "In Vivo Gene Delivery and Stable Transduction of Nondividing Cells by a Lentiviral Vector" Science, 1996, vol. 272, pp. 263-267.

Notredame et al. "SAGA: Sequence alignment by genetic algorithm" Nucl Acid Res, 1996, vol. 24, pp. 1515-1524.

O'Connor et al. "Construction of Large DNA Segments in *Escherichia coli*" Science, 1989, vol. 244, pp. 1307-1312.

Ohi et al. "Construction and replication of an adeno-associated virus expression vector that contains human beta-globin cDNA" Gene, 1990, vol. 1990, pp. 279-282.

Petranka et al. "Structure of the CD59-encoding gene: Further evidence of a relationship to murine lymphocyte antigen Ly-6 protein" Proc Natl Acad Sci, 1992, vol. 89, pp. 7876-7879.

Ramo et al. "Evaluation of Adenovirus-Delivered Human CD59 as a Potential Therapy for AMD in a Model of Human Membrane Attack Complex Formation of Murine RPE" Investing Ophthalmol Vis Sci, 2008, vol. 49, pp. 4126-4136.

Rollins et al. "The Complement-Inhibitory Activity Capacity to Block Incorporation of of CD59 Resides in its C9 Into Membrane C5b-9" J Immunol, vol. 144, pp. 3478-3483.

Sakoda et al. "A High-Titer Lentiviral Production System Mediates Efficient Transduction of Differentiated Cells Including Beating Cardiac Myocytes" J Mol Cell Cardiol, 1999, vol. 31, pp. 2037-2047.

Sumulski et al. "Helper-Free Stocks of Recombinant Adeno-Associated Viruses: Normal Integration Does Not Require Viral Gene Expression" J Virol, vol. 63, 1989, pp. 3822-3828.

Sumulski et al. "Targeted integration of adeno-associated virus (AAV) into human chromosome 19" The EMBO J, 1991, vol. 10, pp. 3941-3950.

Shelling et al. "Targeted integration of transfected and infected adeno-associated virus vectors containing the neomycin resistance gene" Gene Ther, 1994, vol. 1, pp. 165-169.

Sims et al. "Regulatory Control of Complement on Blood Platelets" J Biol Chem, 1989, vol. 264, pp. 19228-19235.

Stauber et al. "Rapid generation of monoclonal antibody-secreting hybridomas against African horse sickness virus by in vitro immunization and the fusion/cloning technique" J Immunol Method, 1993, vol. 161, pp. 157-168.

Bora et al. "CD59, a Complement Regulatory Protein, Controls Choroidal Neovascularization in a Mouse Model of Wet-Type Age-Related Macular Degeneration" J Immunol, 2007, vol. 178, pp. 1783-1790.

Harris et al. "Characterization of the mouse analogues of CD59 using novel monoclonal antibodies: tissue distribution and functional comparison" Immunol, 2003, vol. 109, pp. 117-126.

* cited by examiner

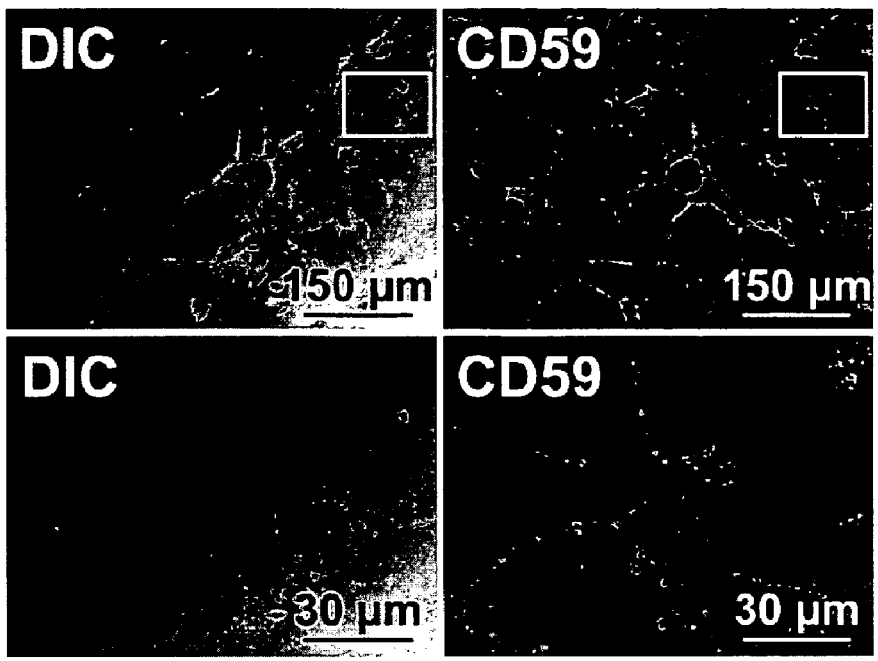
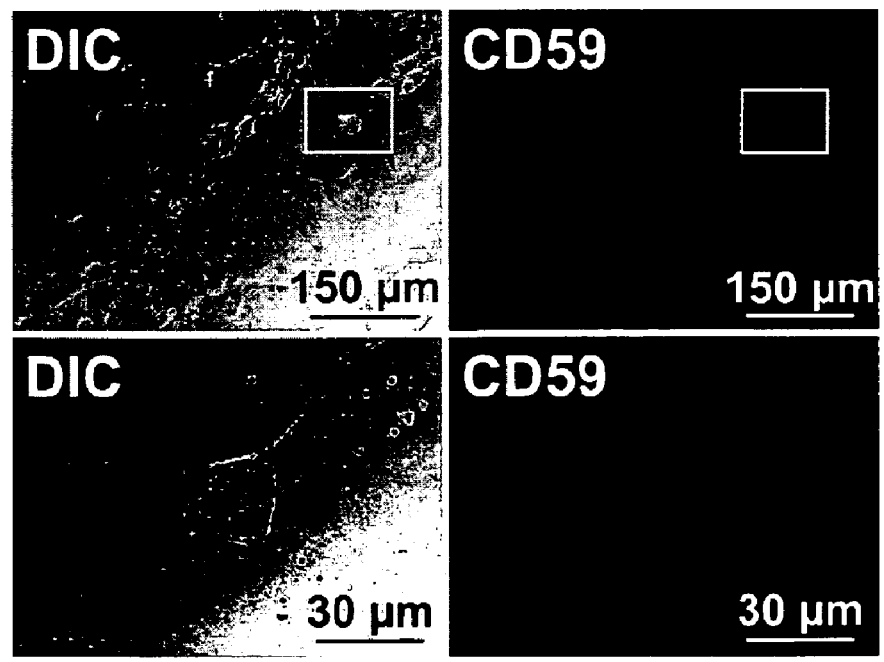
Figure 1C

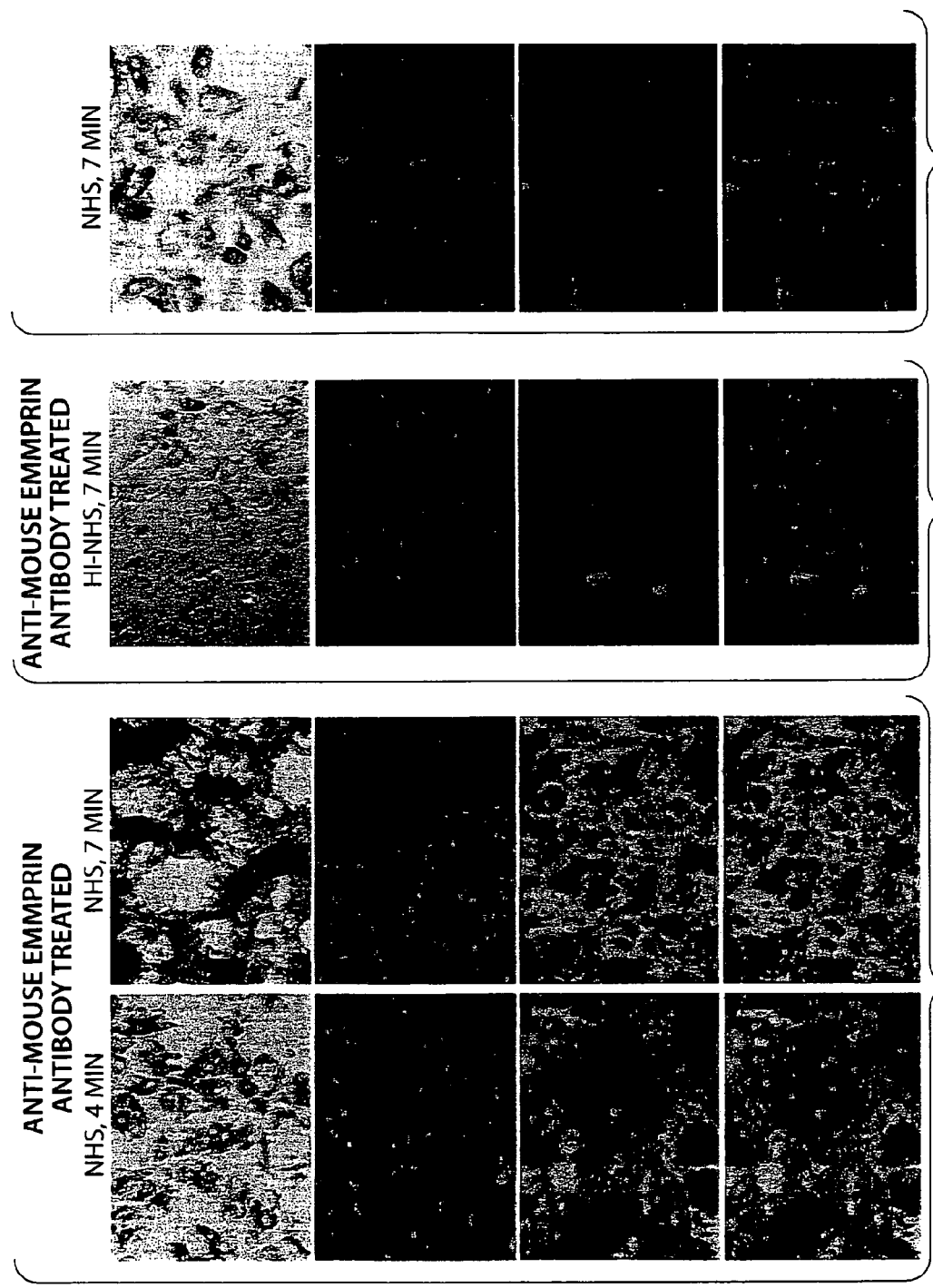

HUMANIZED MODEL OF MEMBRANE ATTACK COMPLEX (MAC) FORMATION ON MURINE RETINA AND COMPOSITIONS, KITS AND METHODS FOR TREATMENT OF MACULAR DEGENERATION

RELATED APPLICATIONS

This application claims the benefit of International application PCT/US2009/000947 entitled, "A humanized model of membrane attack complex (MAC) formation on murine retina and compositions, kits and methods far treatment of macular degeneration" filed Feb. 13, 2009, which claims the benefit of U.S. provisional application Ser. Nos. 61/066,062 filed Feb. 15, 2008, 61/066,288 filed Feb. 19, 2008, and 61/070,650 filed Mar. 25, 2008 in the U.S. Patent and Trademark Office, all of which are hereby incorporated by reference herein in their entireties.

GOVERNMENT SUPPORT

This invention was made with government support under EY014991 and EY013837 awarded by the National Institutes of Health. The government has certain rights in the invention.

TECHNICAL FIELD

Methods and compositions for treating a subject having age-related macular degeneration (AMD), methods of assaying human macular degeneration (MD), and methods and kits for assaying potential therapeutic agents for treatment of human MD are provided herein.

BACKGROUND

Age-related macular degeneration (AMD) is a disease associated with aging that gradually destroys sharp, central vision, and is the leading cause of blindness in the elderly (Klein et al. *Opthalmology* 114:253-262, 2007). The macula is a specific tissue located in the center of the retina, the light-sensitive tissue at the back of the eye that converts light or an image into electrical impulses.

AMD is classified as either wet or dry (Inana et al. U.S. Pat. No. 7,309,487). Wet AMD is characterized by growth of abnormal blood vessels behind the retina under the macula. These new blood vessels are fragile and often leak blood and fluid. The blood and fluid raise the macula from its normal place at the back of the eye, causing loss of central vision. Wet AMD is treated with laser surgery, photodynamic therapy, and injections into the eye. None of these treatments, however, cures wet AMD, rather the treatments slow progression of the disease. Dry AMD is characterized by slow breakdown of light-sensitive cells in the macula, gradually blurring central vision in the affected eye. Over time, less of the macula functions and central vision is gradually lost. There is no known form of treatment for advanced stage dry AMD, and vision loss is inevitable. A specific high-dose formulation of antioxidants and zinc has been shown to prevent intermediate stage AMD from progressing to advanced AMD.

There is a need for methods of assaying (i.e., prognosticating or diagnosing) human macular degeneration (MD), methods of assaying among chemical entities to identify potential therapeutic agents to treat AMD, and methods of treating a human subject having AMD.

SUMMARY

An aspect of the invention herein provides a method for treating AMD in a subject, the method involving contacting retinal pigment epithelium (RPE) of the subject with a CD59 protein composition, in which the retina is treated for AMD.

In related embodiments of the method, contacting the RPE is delivering at least one composition selected from the group consisting of: a nucleic acid vector with a gene encoding CD59 protein; CD59 protein; or CD59 expressed directly from naked nucleic acid.

In related embodiments of any of the above methods, the vector is a viral vector or a plasmid; for example, the viral vector is derived from a genetically engineered genome of at least one virus selected from the group consisting of adenovirus, adeno-associated virus, a herpesvirus, and a lentivirus. For example, the lentivirus is a retrovirus.

In various embodiments of the method, delivery of protein or nucleic acid is by at least one injection route selected from the group consisting of intravenous, intra-ocular, intra-muscular, subcutaneous, and intraperitoneal. In an embodiment of the method, the macular degeneration is dry.

An aspect of the invention provides a method of assaying extent of human MD in a model cell system or a method in a model cell system of assaying a serum complement component for prognosis or diagnosis of macular degeneration (MD), the method including: exposing a first sample of cells to serum and measuring resulting lysis, and comparing extent of lysis to that in a second sample of control cells not so exposed to serum, such that the extent of lysis in the first sample compared to that in the second sample is a measure of complement-induced MD.

An aspect of the invention provides a method of assaying in a model cell system potential therapeutic agents for human MD, the method including: contacting a first sample of cells to serum and measuring resulting lysis, and contacting a second sample of otherwise identical control cells with serum and a source of human CD59 and measuring resulting lysis; and contacting at least a third sample of cells to a candidate therapeutic composition and otherwise identically to serum, such that the extent of lysis of the third sample compared to that in the first and second sample is a measure of protection by the candidate composition, thereby providing the method of assaying for potential therapeutic agents.

A related embodiment of the above methods further includes contacting cells or tissues with a recombinant vector having a gene capable of expressing CD59. Lysis is measured for example by propidium iodide uptake and cell sorting. In a related embodiment of the above methods, the cells are hepatocytes. In related embodiments the cells are of murine origin. In a related embodiment of the above methods, the source of CD59 is human. In a related embodiment of the above methods the serum is normal human serum. Alternatively, the serum is from a diseased subject, for example, the diseased subject has MD.

An aspect of the invention provides a method of diagnosing or prognosing presence or progression of macular degeneration, the method including determining extent of membrane attack complex (MAC) deposition on retina. In a related embodiment of the method, determining extent of MAC deposition is analyzing by immunohistochemistry with antibodies that are specific for human MAC.

An aspect of the invention provides a pharmaceutical composition for treating macular degeneration including CD59 protein or a source of expression of CD59 protein in vivo, in which the composition is formulated for ocular delivery, in a dose effective to treat macular degeneration. In various related embodiments of the composition, the CD59 protein or source of expression of CD59 protein is at least one selected from the group consisting of: a nucleic acid vector with a gene encoding CD59 protein; a viral vector with a gene encoding CD59 protein; and a CD59 protein.

In related embodiments of the composition, the composition formulated for ocular delivery is at least one selected from the group consisting of: injection, eye drop, and ointment. In a related embodiment of the composition, injection is at least one selected from the group consisting of: intraocular injection, subconjunctival injection, and subtenon injection. In a related embodiment, the composition further includes at least one drug selected from the group consisting of: anti-tumor, antiviral, antibacterial, anti-mycobacterial, anti-fungal, anti-proliferative and anti-apoptotic. In a related embodiment, the CD59 protein is expressed as a soluble protein. In a related embodiment, the CD59 protein has a deletion encoding a glycosyl phosphatidyl inositol (GPI) anchoring domain.

An aspect of the invention provides a kit for assaying MAC deposition on ocular tissue or cells and for screening agents that inhibit deposition, the kit includes anti-MAC antibody, a container, and instructions for use with normal human serum. In a related embodiment, the kit further includes anti-emmprin antibody and/or normal human serum. In another related embodiment, the kit further includes CD59 protein as a positive control and the CD59 protein is a soluble form or a membrane-bound form, the latter for example embedded in a liposome preparation. In other related embodiments of the kit, at least one of the antibody, the serum, and the CD59 protein is a lyophil.

An aspect of the invention provides a method in a model cell system of assaying a serum complement component for prognosis or diagnosis of macular degeneration (MD), the method including: contacting detectably labeled cells with serum from a subject and measuring amount of extracellular and/or intracellular detectable agent for contacted cells; and comparing extracellular and/or intracellular agent in the cells to that in detectably labeled control cells not exposed to the serum and otherwise identical, such that amount of extracellular and/or intracellular agent in the contacted cells is compared to that in the control cells, such that a greater amount of extracellular detectably labeled agent in cells contacted with serum compared to the control cells is an indication of prognosis or diagnosis of MD.

An aspect of the invention provides a method of assaying in a model cell system a potential therapeutic agent for efficacy in treatment of human macular degeneration (MD), the method including: contacting a first sample of detectably labeled cells with serum from a subject and measuring amount of extracellular and/or intracellular detectable agent, and contacting a second sample of otherwise identical detectably labeled control cells with serum and a source of human CD59 protein and measuring amount of extracellular and/or intracellular detectable agent; and contacting at least a third sample of detectably labeled cells to at least one candidate therapeutic composition and otherwise identically to serum and measuring amount of extracellular and/or intracellular detectable agent, such that the amount of extracellular and/or intracellular detectable agent of the third sample compared to that in the first sample and the second sample is a measure of protection by the candidate composition, such that a greater amount of extracellular detectably labeled agent is an indication of MD, thereby assaying for a potential therapeutic agent for efficacy in treatment of human MD.

In various embodiments of the above methods, the detectable agent is at least one composition selected from the group consisting of a recombinant vector having a gene capable of expressing a detectable protein, a fluorescent agent, a colorimetric agent, an enzymatic agent, and a radioactive agent. For example, the detectable protein is at least one fluorescent protein selected from the group consisting: green fluorescent protein, aequorin, cyan fluorescent protein, DsRed fluorescent protein, enhanced green fluorescent protein, and yellow fluorescent protein. In other embodiments, the detectable agent is not a protein, for example, the detectable agent is at least one fluorescent agent selected from the group consisting of: Indocyanine Green, Doxorubicin, Riboflavin, Chlorophyll, and Porphyrin. In other embodiments, the detectable protein is enzyme, for example, β-galactosidase or alkaline phosphatase.

In embodiments of the above methods, the cells are hepatocytes; exemplary cells are of murine origin. In embodiments of the above methods, the source of CD59 protein is human. In certain embodiments of the above methods, the serum is normal human serum. Alternatively, the serum is from a diseased subject. In general, the subject is in need of diagnosis or prognosis of MD. In other embodiments, the CD59 protein is soluble. In other embodiments the protein is membrane-bound.

BRIEF DESCRIPTION OF THE DRAWINGS

FIG. 1 panel B is a photograph of Western blots using a monoclonal antibody specific for binding to human CD59 (top) and for control protein actin (bottom), showing presence of human CD59 in lysates of cells contacted with AdCAGCD59 (dark band at approximately 18 kD in the mouse hepa-1c1c7 cell lysate group, left channel). CD59 signal was not detected in cell lysates from cells contacted with the control virus vector or in lysates in control cells not pretreated with vector (mouse hepa-1c1c7 cell lysate group, middle and right channels). Endogenous human CD59 was also detected in human embryonic retinoblast (911) cell lysates (faint band at approximately 18 kD in the 911 cell lysate group). This signal was much weaker compared to the signal from the mouse cells contacted with AdCAGCD59 (comparing dark band at approximately 18 kD in the mouse hepa-1c1c7 cell lysate group, left channel to faint band at approximately 18 kD in the 911 cell lysate group). The second Western blot was a control for expression of housekeeping gene β-actin.

FIG. 1 panel C is a set of photomicrographs showing AdCAGCD59 contacted cells (on the left), and these cells immunostained with anti-hCD59 antibody (right indicated CD59). The left top photomicrograph was visualized using differential interference contrast (DIC) of the cells, at two different magnifications (length bars 100 μm and 20 μm). The right photomicrographs show immunohistochemistry detection of these cells for expression of CD59 and localization on the cell membrane. A substantial amount or possibly all of the cells were found to express CD59 protein. FIG. 1 panel C (right) is a set of photomicrographs of control cells (contacted with control vector AdCAGGFP) treated as in the left photomicrographs. These data show that CD59 was not expressed in these cells.

FIG. 2 panel A is a line graph showing percent of lysis of control cells not contacted with vector, on the ordinate, as a function of concentration of serum (normal human serum, herein NHS), on the abscissa, which cells were incubated. Lysis of untreated control cells was observed to be a function of serum concentration during the incubation. The lowest serum concentration that yielded maximal cell lysis was 1% (1/100 dilution; cell lysis was 96.06%±0.87%). This serum concentration was used in subsequent Examples herein.

FIG. 2 panels B, C, and D are printouts of cell sorting data showing results of human serum cell lysis assays with extent of propidium iodide (PI) labeling of cells shown on the abscissa (acquired in the FL3-H channel) and the number of cells on the ordinate. FIG. 2 panel B shows that in untreated cells (labeled uninfected), the cells treated with HI-NHS sorted to a location of lesser PI uptake cells treated with NHS (greater PI uptake). FIG. 2 panel C shows that cells contacted with AdCAGGFP vector were sorted similarly as untreated cells. FIG. 2 panel D shows that substantially all of the cells treated with vector AdCAGCD59 were sorted to the same position as those treated with heat inactivated NHS (HI-NHS), i.e., susceptibility to NHS was substantially or even entirely decreased by pretreatment with AdCAGCD59. In this example, PI is preferentially taken up by non-living cells, viz., the peak on the right. Cells contacted with the AdCAGCD59 vector were significantly protected, i.e., reducing complement mediated cell lysis to 12.29%±0.18%. FIG. 2 panel C shows that mouse cells contacted with the control vector (AdCAGGFP) were susceptible to cell lysis due to human serum complement (cell lysis was 95.27%±0.01%). Similarly, FIG. 2 panel B shows that control cells not pretreated or contacted with vector were susceptible to human complement and cell lysis. These data show that cells were protected from lysis due to expression of human CD59 from the AdCAGCD59 vector, rather than from contact with an adenovirus vector.

FIG. 2 panel E is a bar graph comparing percent cell lysis (ordinate) of different groups of cells on the abscissa: control cells (not pretreated with vector, and cells contacted with control vector AdCAGGFP) to cells contacted with AdCAGCD59. Each bar represents a different treatment sample of the cells. The data in this graph show that cells contacted with AdCAGCD59 vector were significantly protected, as complement mediated cell lysis was 12.29%±0.18% (right bar). Cells treated with the control vector AdCAGGFP were susceptible to human complement with cell lysis of 95.27%±0.01% (middle bar). Untreated cells were susceptible to human complement and cell lysis (also about 95% cell lysis; left bar). These data show that human CD59 pretreatment of cells with AdCAGCD59 vector protected the cells from lysis.

FIG. 2 panel F is a line graph showing percent cell lysis (ordinate) of pretreated cells as a function of multiplicity (vector particles/cell of pretreatment; abscissa). In cells pretreated with AdCAGCD59 vector, cell lysis decreased with increasing multiplicity. Treatment with 250 virus particles (vp/cell) resulted in inhibition of cell lysis by more than 50%. Cells treated with the control vector showed complete lysis of cells even at highest multiplicities.

FIG. 3 panel A shows mouse cells on poly-D-lysine coated chamberslides incubated with 10% NHS at 37° C. for one to ten minutes and subsequently washed and fixed. The left photomicrographs are visualized by DIC at different magnifications (as indicated by bars of length 100 µm and 20 µm). The right photomicrographs show results of cells contacted with anti-MAC antibody and with DAPI at different magnifications (100 µm and 20 µm). DAPI is 4'-6-Diamidino-2-phenylindole, a compound that forms fluorescent complexes with natural double-stranded DNA. These photomicrographs show that incubation of cells with NHS for five minutes caused significant changes in cell morphology compared to control cells incubated with HI-NHS; cells lost their extensive cytoplasmic processes and became round and granular (FIG. 3 panel A, left photomicrographs) compared to cells treated with HI-NHS (FIG. 3 panel B, left photomicrographs). Immunocytochemical analysis using a monoclonal antibody directed to a neoepitope on the C5b-9 complex showed extensive membrane staining at the borders of cells treated with NHS confirming deposition of the MAC on these cells (FIG. 3 panel A) compared to control cells treated with HI-NHS (FIG. 3 panel B).

FIG. 3 panel B shows results of examples similar to that in FIG. 3 panel A, except using HI-NHS. The data show that the cells did not change morphology, i.e., the HI-NHS did not have the same deleterious effect on cells as NHS.

FIG. 3 panel C is a set of photomicrographs taken with DIC, in which the left photomicrograph shows cells contacted with NHS and then stained with trypan blue, and the right photomicrograph shows cells contacted with HI-NHS and then stained with trypan blue. Lysis of a substantial number of NHS treated cells was observed as determined by trypan blue staining (left); substantially no lysis was observed with HI-NHS contacted cells (right), as indicated by normal cell morphology and absence of trypan blue uptake (right). Further, cells treated with HI-NHS maintained a normal cell morphology, while those exposed to NHS lost processes associated with normal cells. Images are representative of three independent experiments for each type of serum tested.

FIG. 4 panel B is a set of photomicrographs of another sample of cells pretreated with the AdCAGCD59 vector expressing CD59 with the same experimental protocol as FIG. 4 panel A. In contrast to data in FIG. 4 panel A, cells pretreated with the CD59 vector retained normal morphology, and were protected from MAC stain even after seven minutes of incubation with NHS. Images are representative of three independent experiments for each type of serum experiment.

FIG. 4 panel C is a set photomicrographs taken by DIC of cells pretreated with AdCAGGFP and then stained with trypan blue (left), and cells pretreated with AdCAGCD59 and then stained with trypan blue (right).

FIG. 4 panels A, B, and C show that pretreating mouse hepa-1c1c7 cells with AdCAGCD59 vector significantly protected these cells from MAC deposition and lysis (FIG. 4 panel B and 4 panel C right photomicrograph). Cells pretreated with CD59 expressing vector and then exposed to NHS for five minutes maintained normal healthy morphological characteristics (FIG. 4 panel B, upper row, middle photomicrograph and lower right photomicrograph). Cells pretreated with the control adenovirus vector and expressing GFP were not protected against MAC deposition after five minutes of NHS treatment (FIG. 4 panel A). Abnormal morphological changes were observed in these cells including loss of cytoplasmic processes and round and granular shape (FIG. 4 panel A, upper row, middle and lower right photomicrographs). MAC immunostaining was observed (FIG. 4 panel A, middle row, middle and lower right photomicrographs), and lysis of a substantial amount of control cells was observed by trypan blue staining (FIG. 4 panel C, left photomicrograph).

Figure 4A:
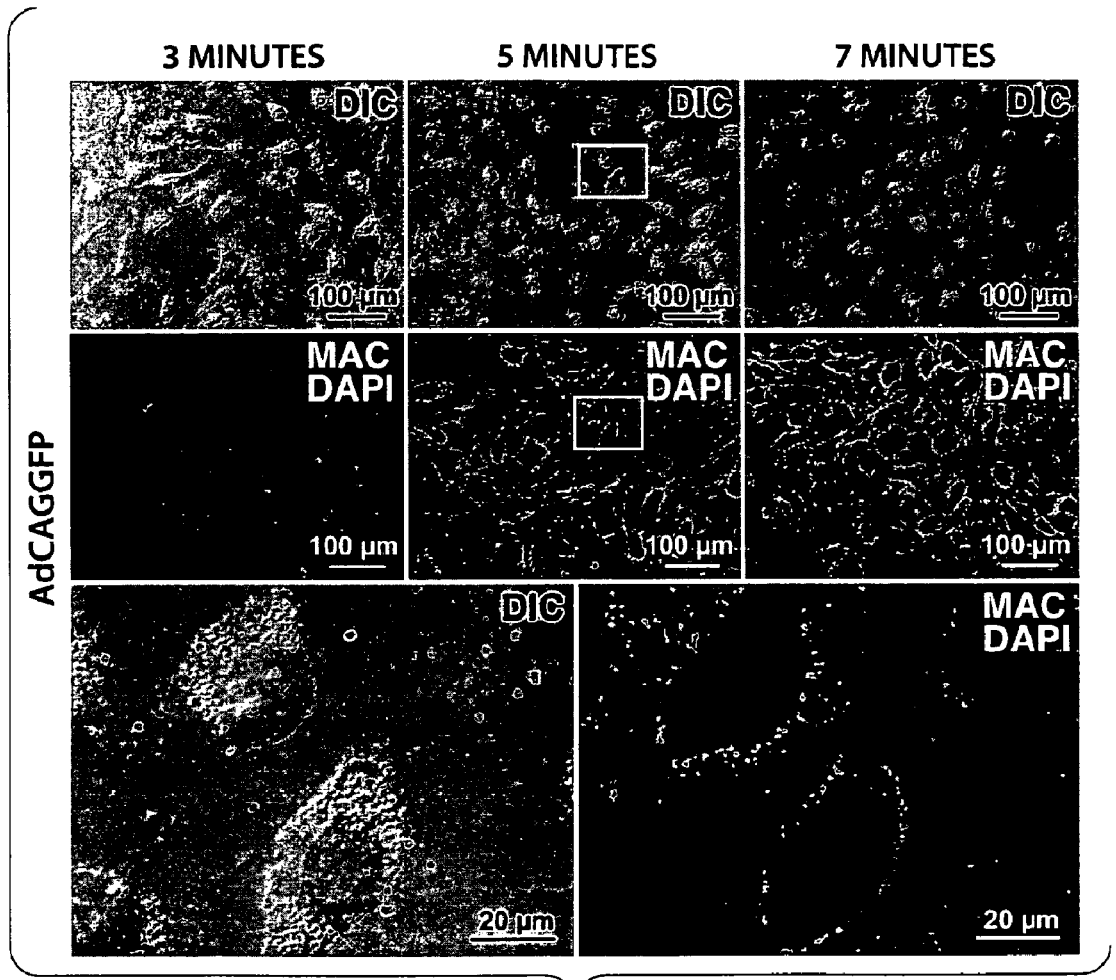
FIG. 4 panel A is a set of photomicrographs of mouse hepa-1c1c7 cells pretreated with the control vector AdCAGGFP and then incubated with NHS for three, five, and seven minutes, and visualized by several methods. The top row shows cells visualized by DIC; the middle row shows the same cells visualized by MAC/DAPI; and the lower row show increased magnification of the highlighted portions of the photomicrographs at five minutes. The cells showed increasing lysis and loss of normal morphology during the time course NHS incubation, after five minutes and seven minutes. Images are representative of three independent experiments for each type of serum tested.
Figure 4B:
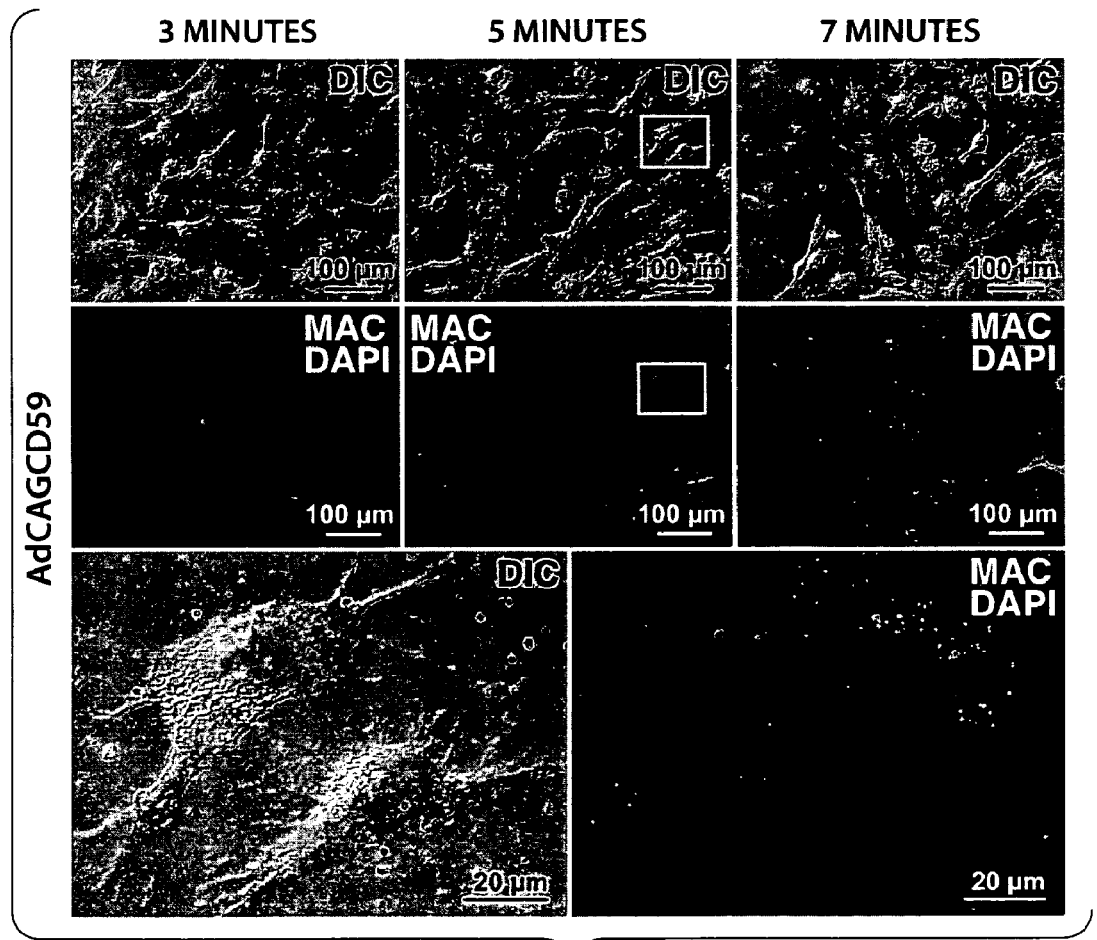
Figure 4C:
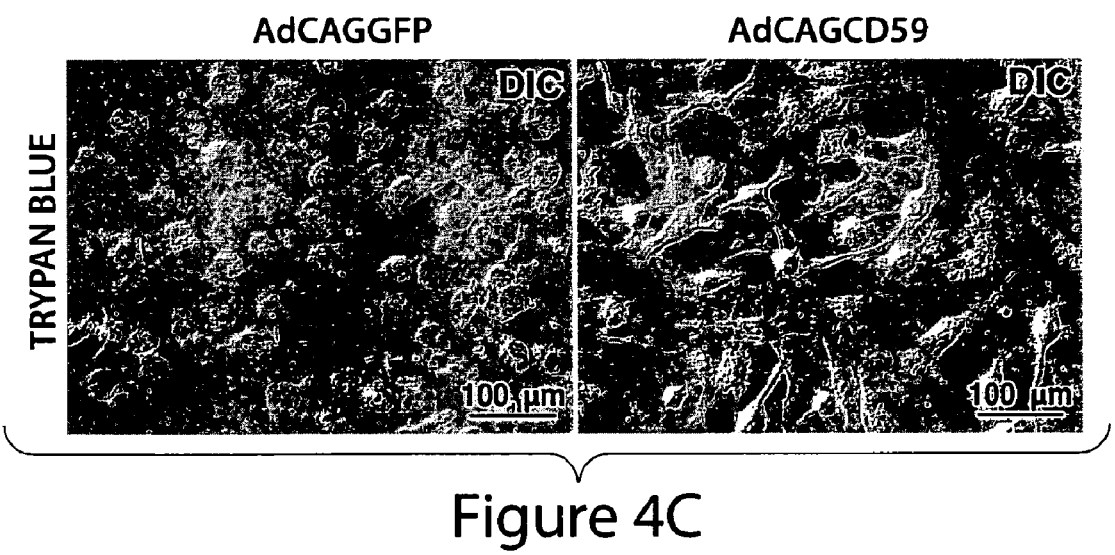

These photomicrographs further show a small extent of MAC staining in some AdCAGCD59 pretreated cells after seven minutes of NHS treatment (FIG. 4 panel B, middle row, right photograph). Control cells pretreated with AdCAGGFP after seven minutes of NHS treatment, MAC staining was significantly stronger (FIG. 4 panel A, middle row, right photomicrograph) than in cells treated with AdCAGCD59 (FIG. 4 panel B, middle row, right photmicrograph).

Figure 5:
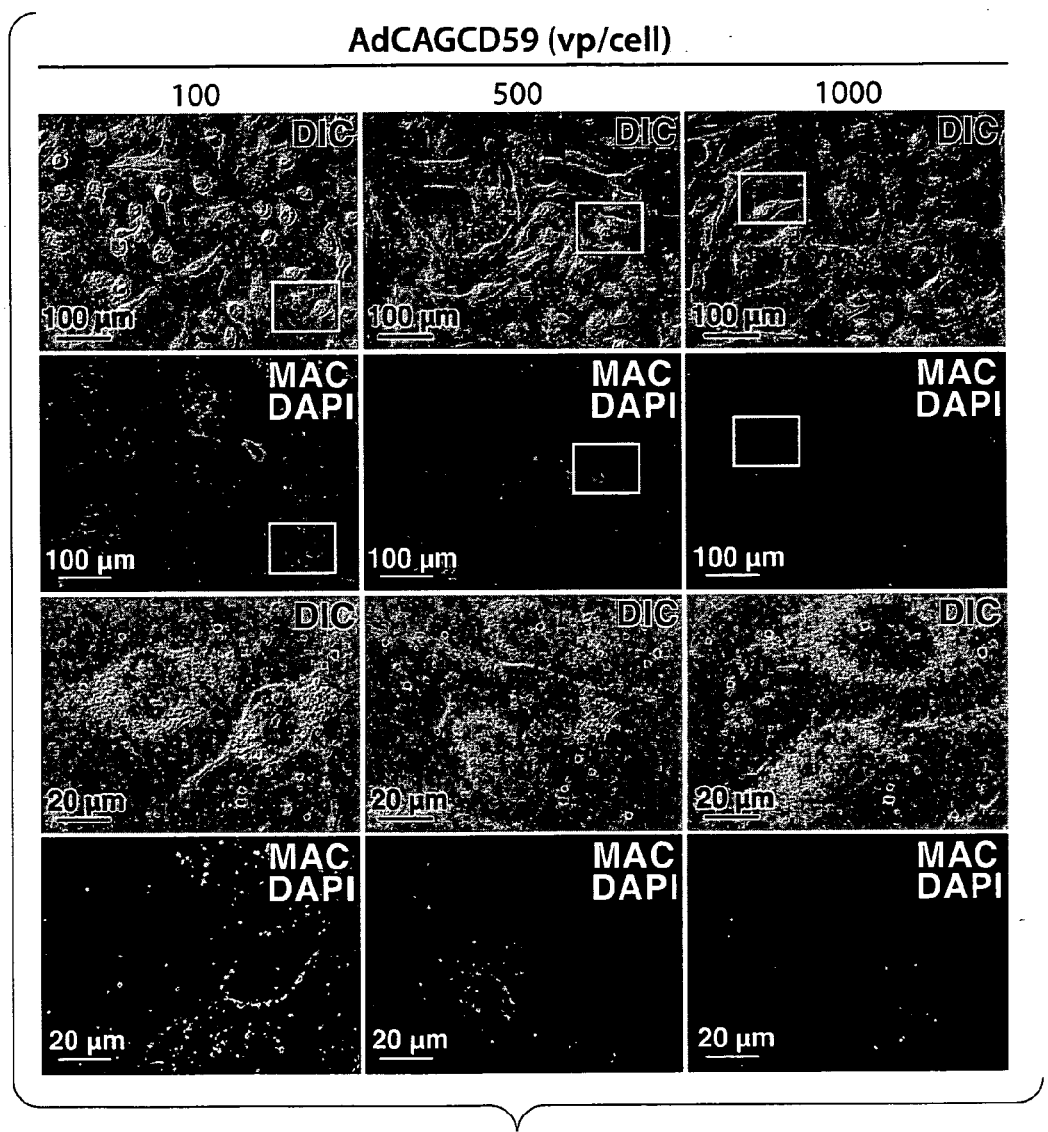
Figure 6A:
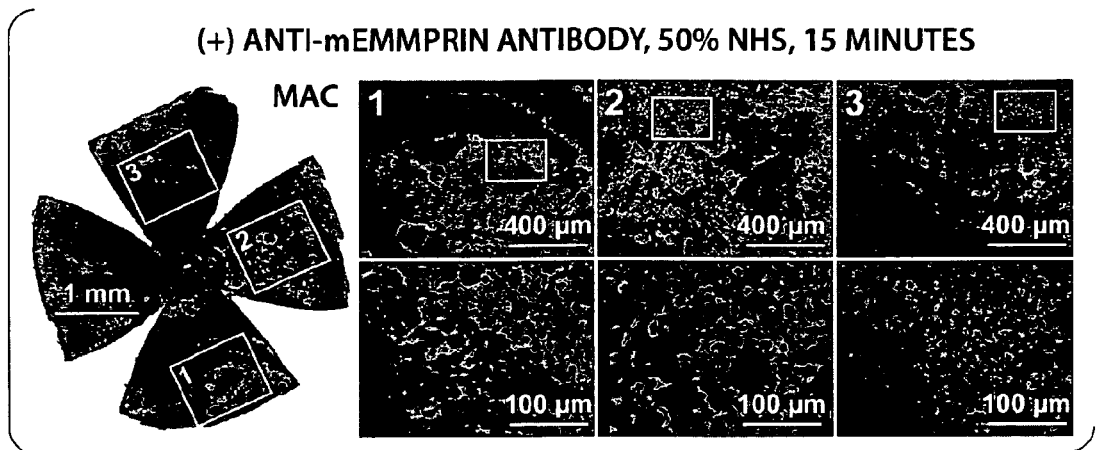
Figure 6B:
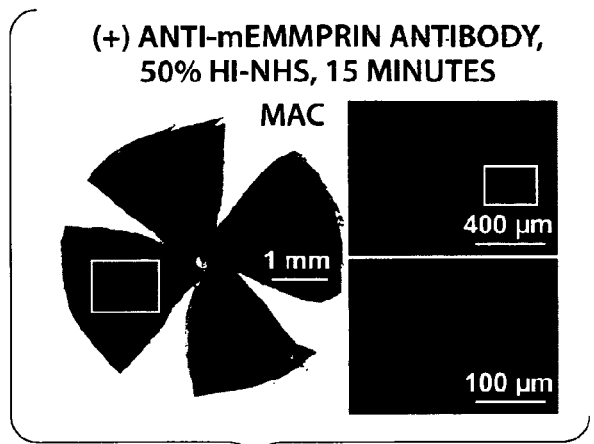
Figure 6C:
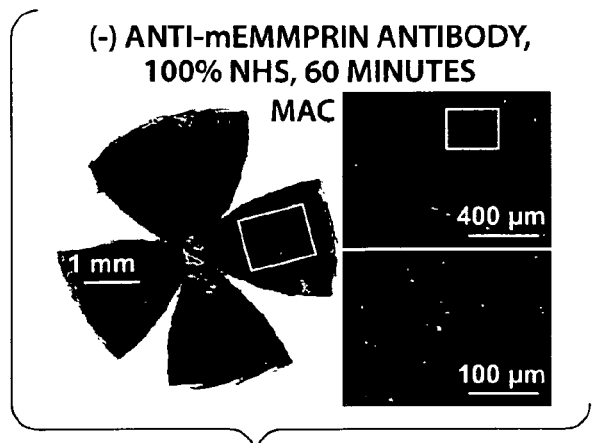
Figure 6D:
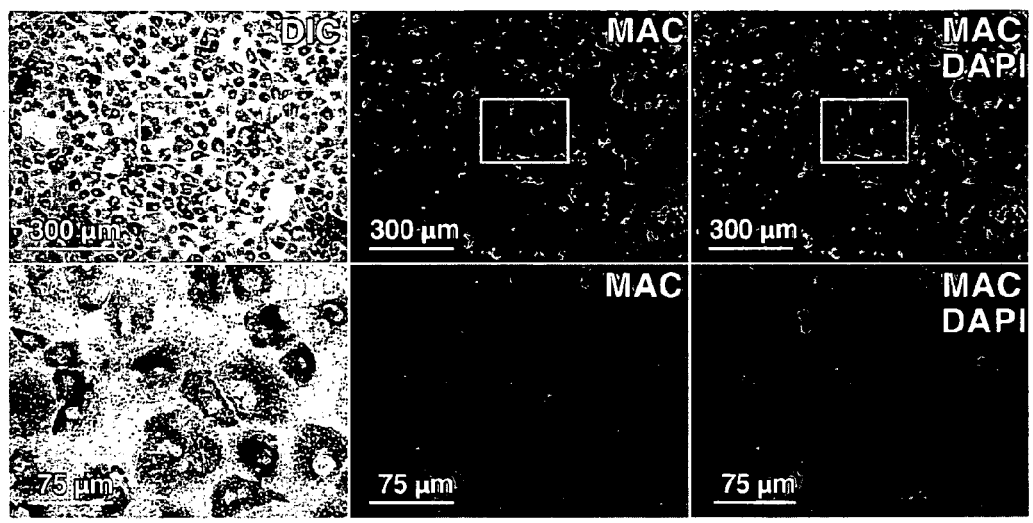
Figure 6E:
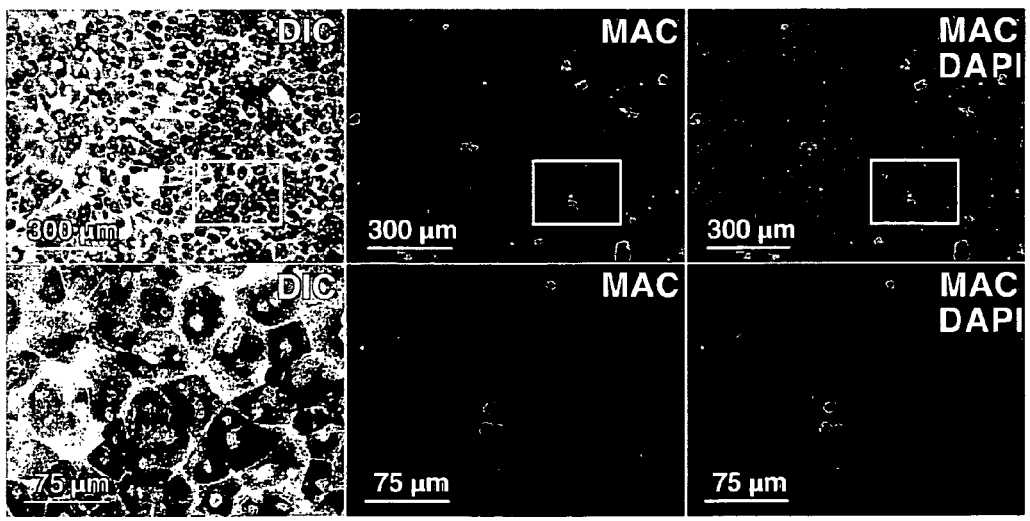

FIG. 5 is a set of photographs showing the effect on cells of pretreatment at different multiplicities of vector particles per cell (vp/cell) of vector AdCAGCD59 particles per cell, at two magnifications (see distance bars), on survival with NHS for five minutes. Left column: cells treated with 100 vp/cell and five minutes of NHS treatment, visualized under four conditions. Middle column: cells treated with 500 vp/cell and five minutes of NHS treatment. Right column: 1000 vp/cell and five minutes of NHS treatment. These photomicrographs show that MAC immunostaining was reduced in cells pretreated at higher multiplicities with AdCAGCD59 vector. Cells pretreated at higher vector multiplicities further show a greater percent of normal morphologies. FIG. 5 shows the inverse relationship between human MAC deposition and amount of adCAGCD59 adenovirus used to pretreat cells.

FIG. 6 is a set of photomicrographs of murine eyecups (panels A, B, and C) and primary murine RPE cells (panels D and E) incubated with (+) or without (−) a complement activating anti-mouse emmprin antibody (indicated anti-mEmmprin antibody in the figures), followed by treatment as indicated with NHS or control HI-NHS for time periods shown in the figure. Eyecups and RPE cells were tested for human MAC deposition. Primary RPE cells were labeled with DAPI. Images are representative of at least three independent experiments each for set of eyecups (n=4 eyecups for each condition) and each set of primary RPE cells.

FIG. 6 panel A (left) shows human MAC deposition immunochemistry data obtained from eyecup tissues (dissected to a flat surface, length bar 1 mm) contacted with an anti-emmprin antibody then by 50% NHS. Photomicrographs 1-3 (right) show two magnifications (length bars 100 and 400 µm) of the dissected cells. Extensive MAC immunostaining of eyecup cells was observed, and the RPE monolayer of these eyecups appeared convoluted and various patterns of staining were observed.

FIG. 6 panel B shows data as in FIG. 6 panel A, however using HI-NHS. No MAC immunostaining on the RPE of the murine eyecups was observed, compared to extensive immunostaining observed of cells incubated with NHS (FIG. 6 panel A).

FIG. 6 panel C shows data as in FIG. 6 panels A and B, however incubated with 100% NHS for 60 minutes at 37° C., and not contacted anti-emmprin antibody before the addition of the NHS. Data show staining was occasional, scattered and weak.

FIG. 6 panel D shows primary murine RPE cells analyzed by human MAC immunochemistry results, DIC, and DAPI for cells contacted with an anti-emmprin antibody followed by NHS. Cells are shown at two different magnifications (as indicated by bars of length of 300 µm and 75 µm). Extensive MAC immunostaining was observed as was observed for eyecups (FIG. 6 panel B).

FIG. 6 panel E shows results for primary murine RPE cells as in FIG. 6 panel D but with HI-NHS for 7 minutes at 37° C. Less extensive MAC immunostaining was observed than in cells incubated with NHS (FIG. 6 panel D).

Figure 7:
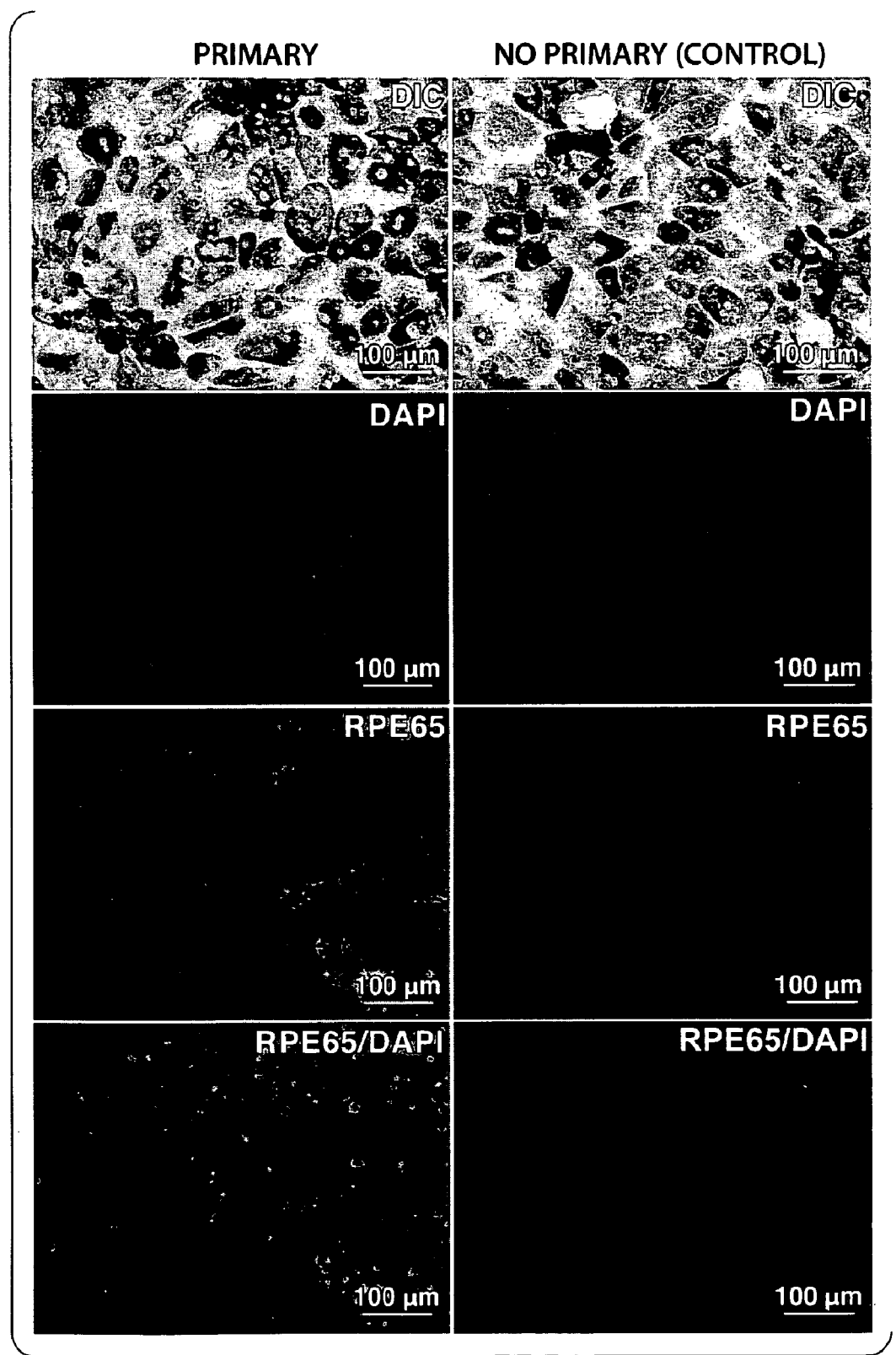
Figure 9A:
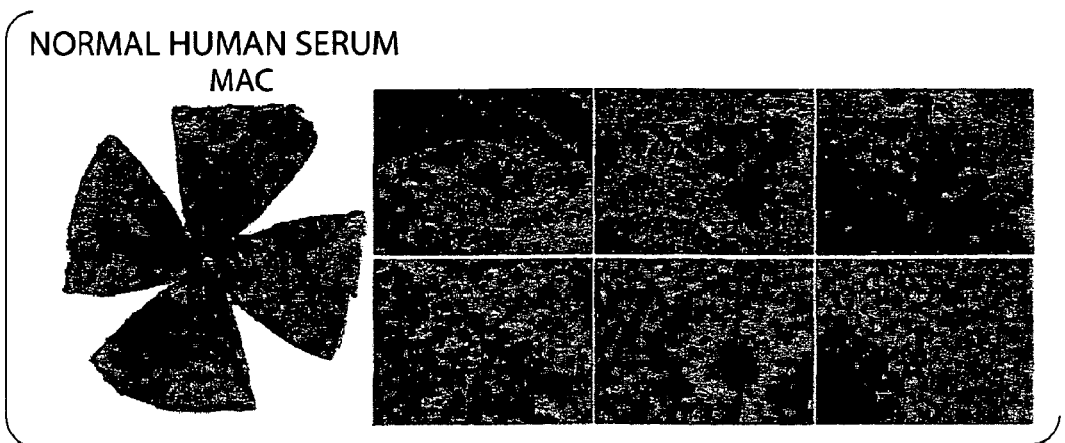
Figure 9B:
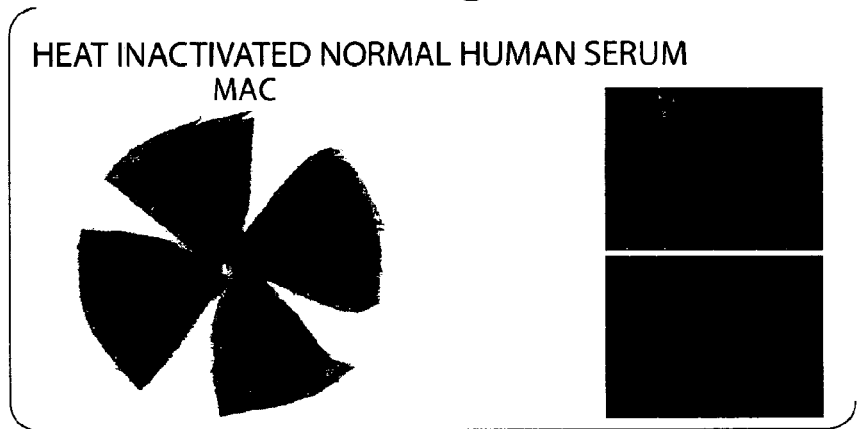
Figure 9C:
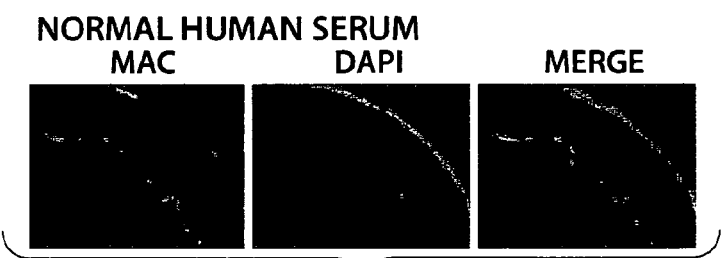
Figure 9D:
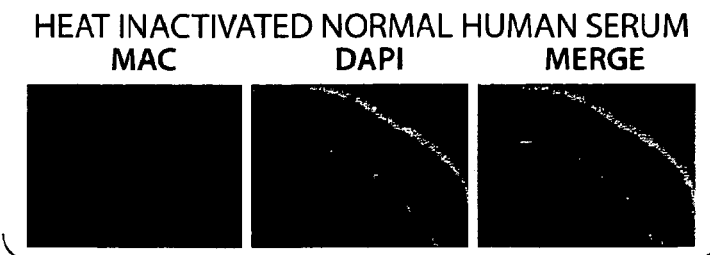

FIG. 7 is a set of photomicrographs showing of RPE cells tested analyzed with a double antibody assay using anti-mouse RPE65 antibody (indicated RPE65 in the figure, third row) visualized by an appropriate Cy3-conjugated secondary antibody. The column on the left shows photomicrographs of cells stained with anti-mouse RPE65 antibody (Primary). The column on the right shows photomicrographs of control cells not contacted with the primary anti-RPE65 antibody and further treated with secondary antibody, indicated in the figure as No Primary (Control). Cells were visualized by each of DIC, DAPI, and by superimposing the RPE65 and DAPI staining (indicated RPE65/DAPI, fourth row).

FIG. 8 is a set of photomicrographs showing data obtained by contacting RPE cells with anti-emmprin antibody and 50% NHS for four minutes (FIG. 8 panel A, left column), or contacting RPE cells with the anti-emmprin antibody and 50% NHS for seven minutes (FIG. 8 panel A, right column), or contacting RPE cells with the anti-emmprin antibody and 50% HI-NHS for seven minutes (FIG. 8 panel B), or contacting RPE cells with 50% NHS alone for seven minutes (control; FIG. 8 panel C). Top row: cells visualized by BF; second row: cells stained with DAPI; third row: cells contacted with anti-human C5b-9 antibody; and fourth row: merges of the DAPI and antibody second and third row results.

FIG. 8 panel A shows extensive MAC immunostaining on the RPE cells treated with the anti-emmprin antibody and 50% NHS for four minutes (left column, third row), and after seven minutes of NHS treatment. This Fig. shows that a substantial amount of RPE cells have detached from the slide (right column, third row). FIG. 8 panel A also shows that cell aggregates of high confluence areas occasionally remain and that these areas are strongly positive for MAC (left and right columns, third row). FIG. 8 panel B shows that HI-NHS treated cells did not bind to anti-MAC antibody (third row).

FIG. 9 is a set of photographs showing mouse eyecup tissues and photomicrographs of mouse cornea tissues.

FIG. 9 panel A shows results for eyecup tissues (dissected to present a flat surface) contacted with an anti-mouse emmprin antibody followed by addition of NHS (final concentration 50% for 15 minutes at 37° C.). After exposure to NHS, RPE monolayer appeared convoluted and displayed various patterns of staining due to different amounts of MAC deposition and various amounts of cell damage.

FIG. 9 panel B shows results for eyecup tissues contacted with an anti-mouse emmprin antibody followed by addition of HI-NHS (final concentration 50% for 15 minutes at 37° C.). Cells contacted with HI-NHS show absence of MAC immunostaining in RPE cells and corneal endothelium.

FIG. 9 panel C shows results for cornea tissues contacted with an anti-mouse emmprin antibody followed by addition of NHS (final concentration 50% for 20 minutes at 37° C.). After exposure to NHS, RPE monolayer appeared convoluted and displayed various patterns of staining due to different amounts of MAC deposition and various amounts of cell damage.

FIG. 9 panel D shows sells contacted with HI-NHS show absence of MAC immunostaining in RPE cells and corneal endothelium.

Figure 10A:
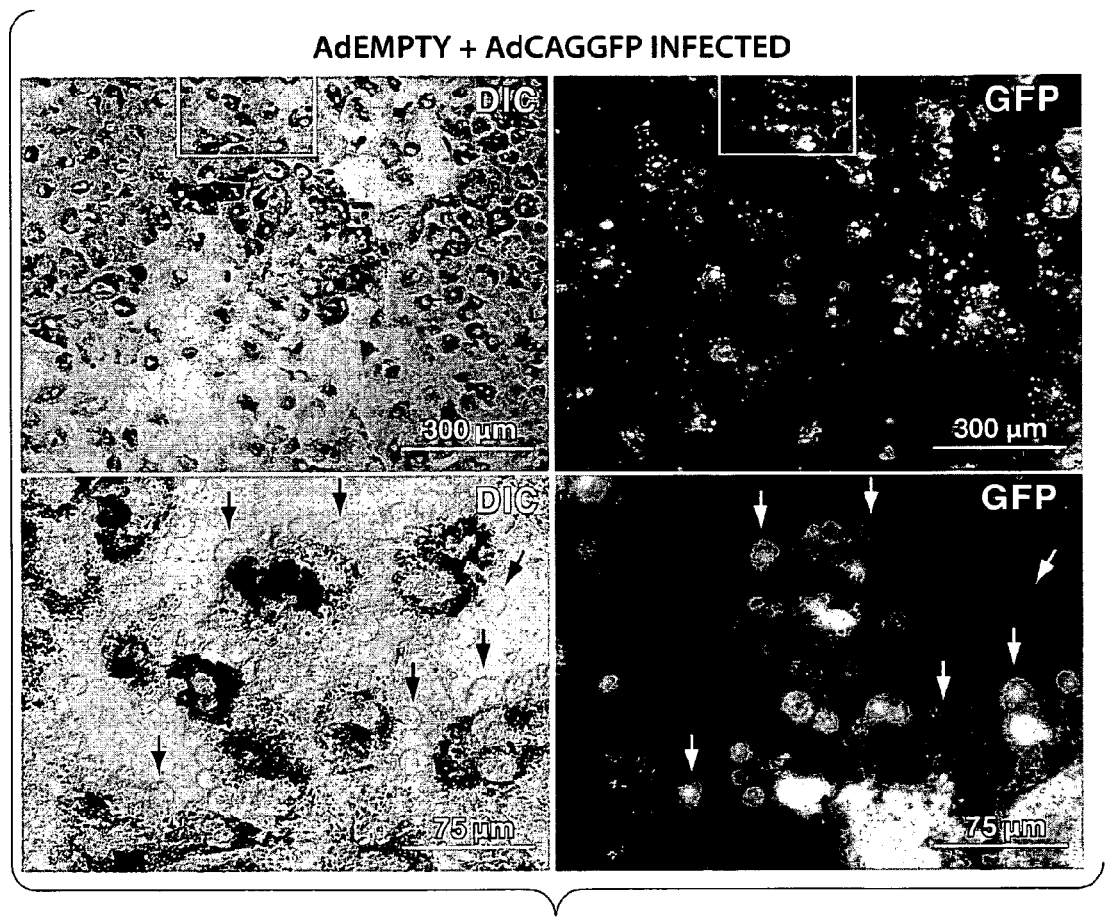
Figure 10B:
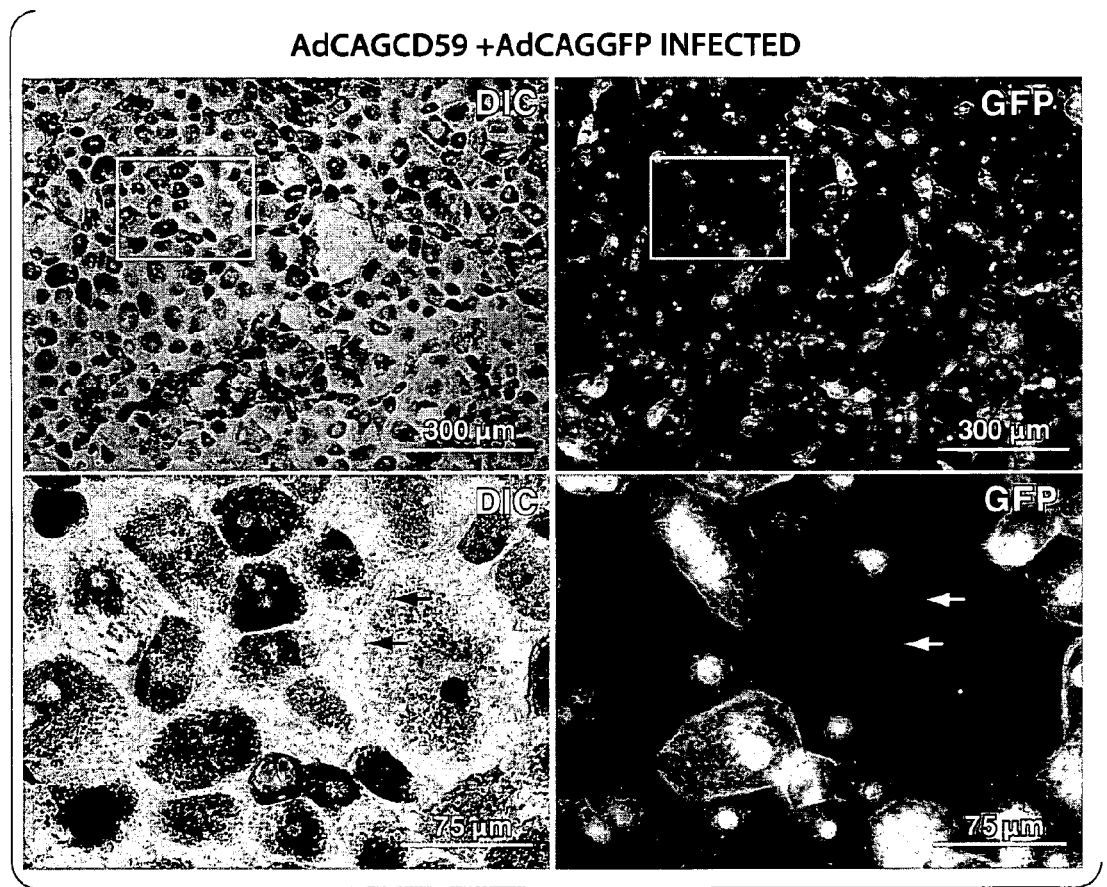
Figure 11A:
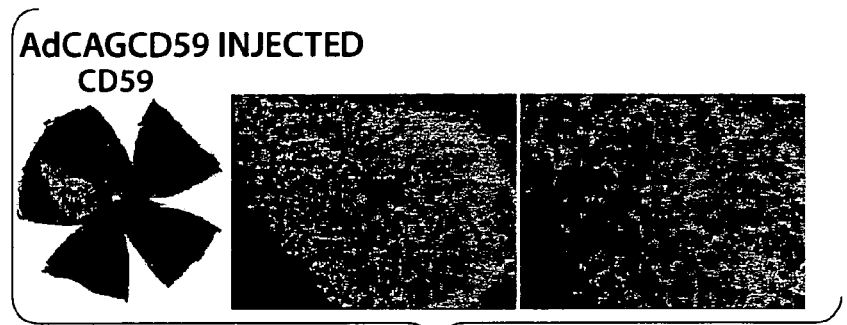
Figure 11B:
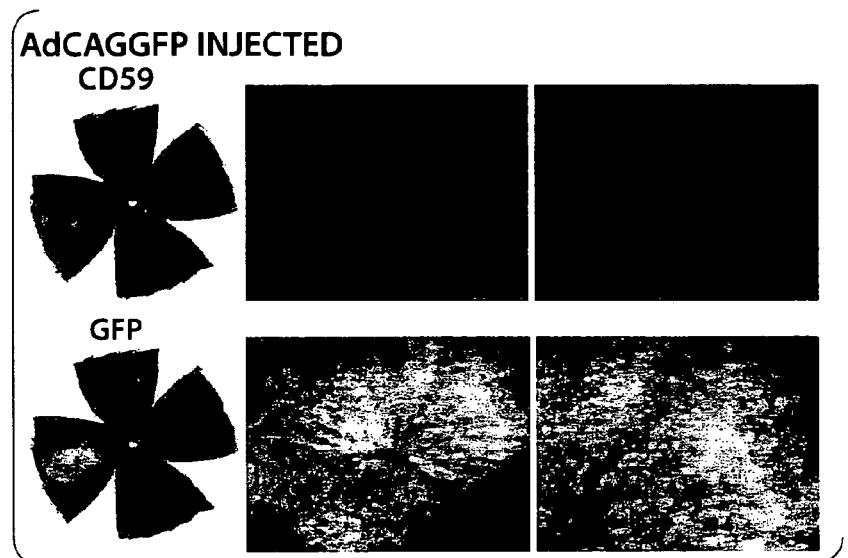
Figure 11C:
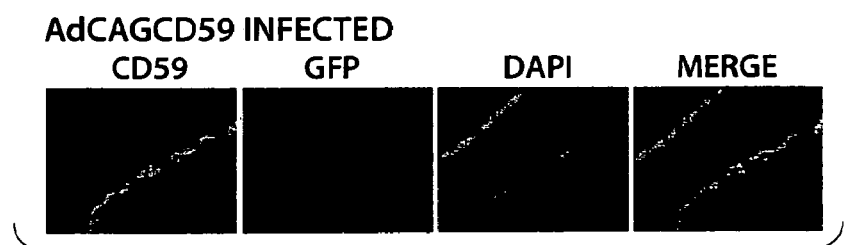
Figure 11D:
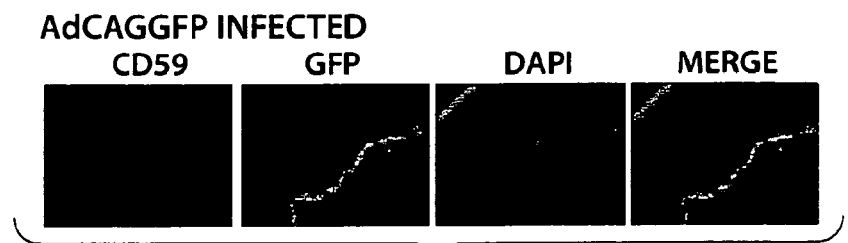
Figure 12A:
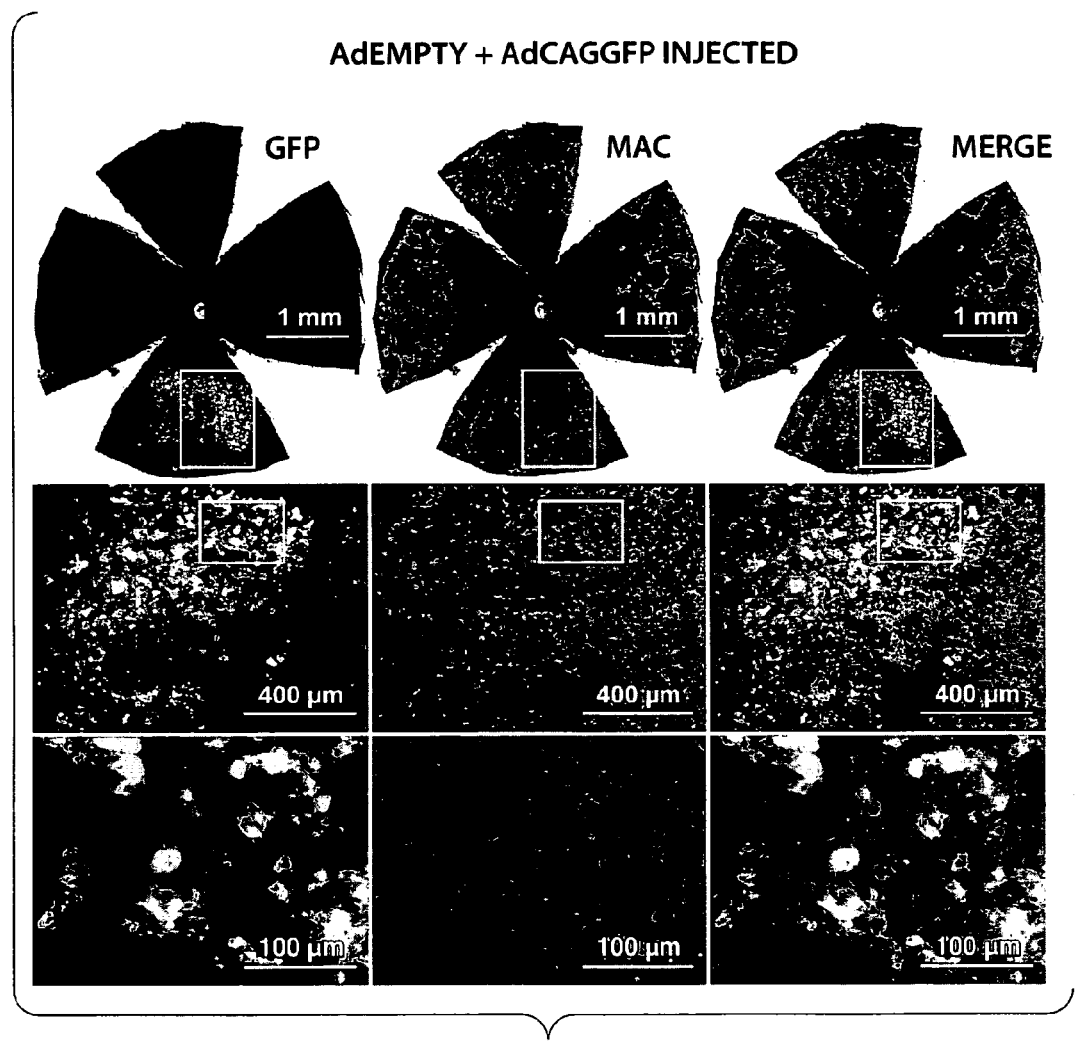
Figure 12B:
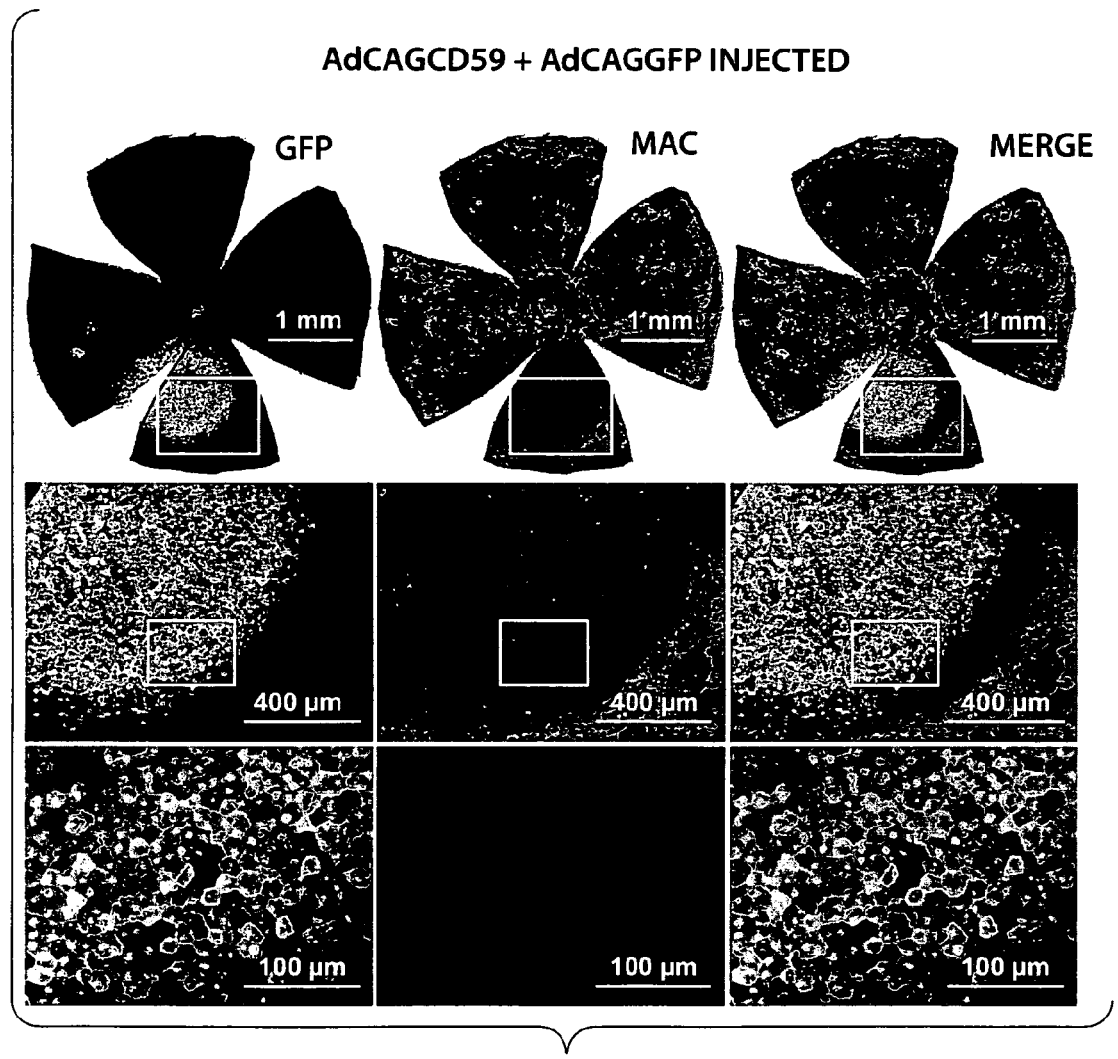
Figure 12C:
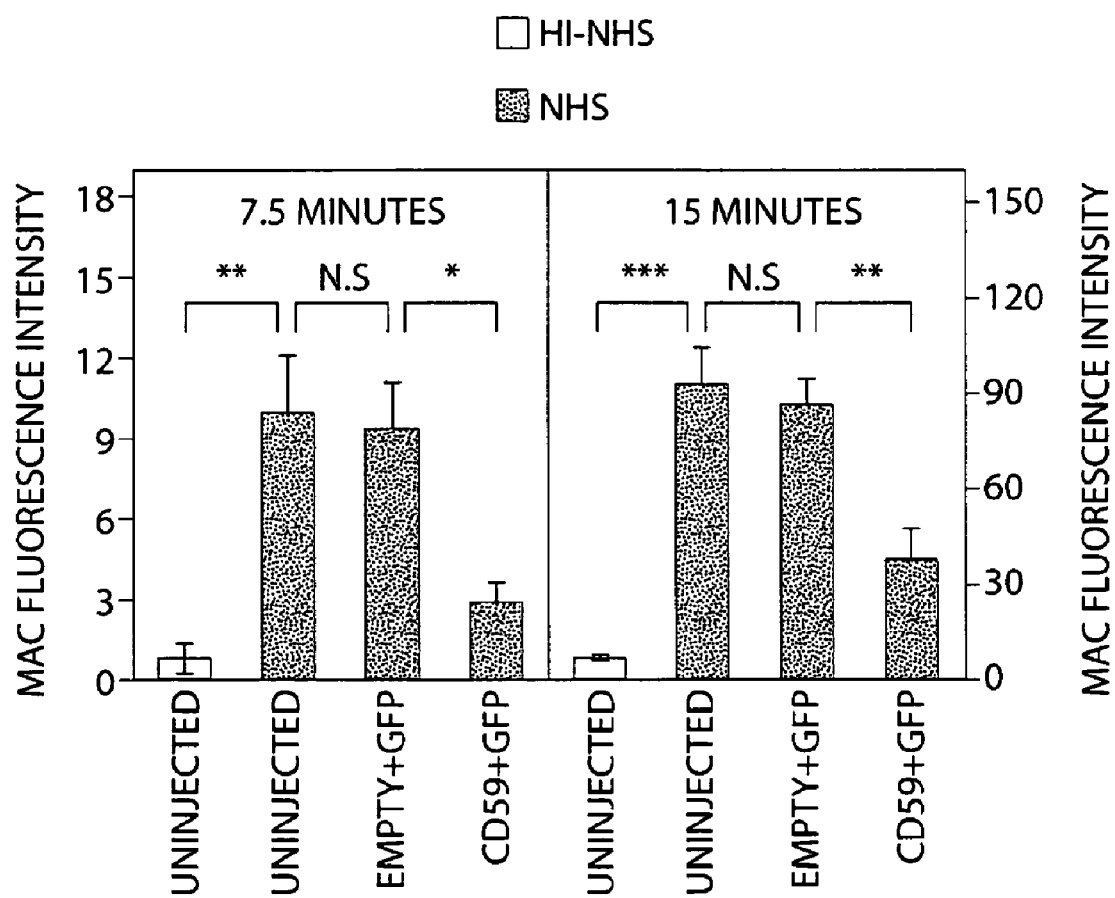
Figure 12D:
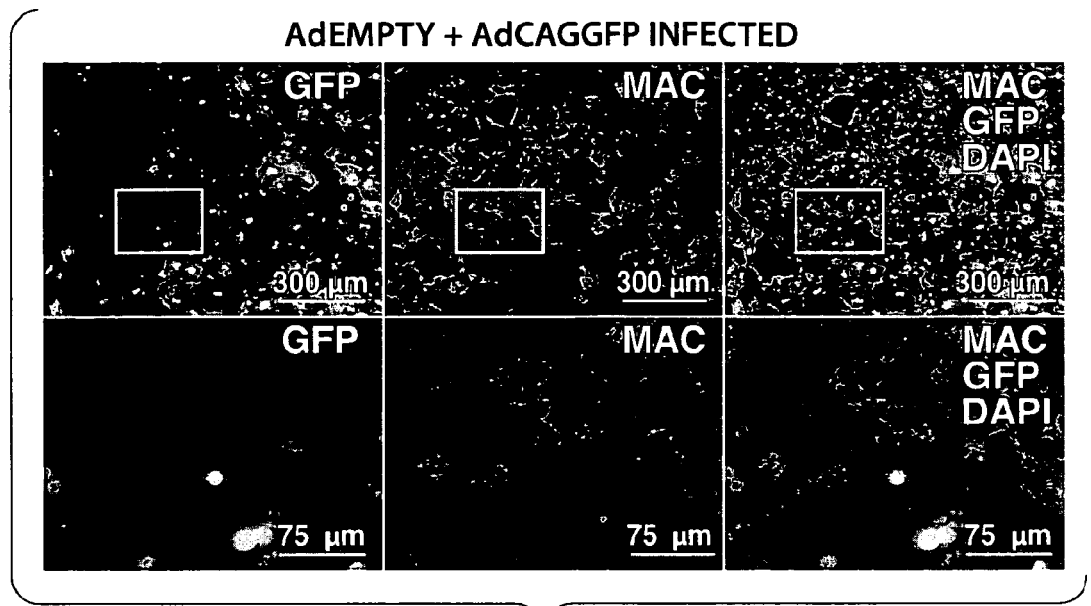
Figure 12E:
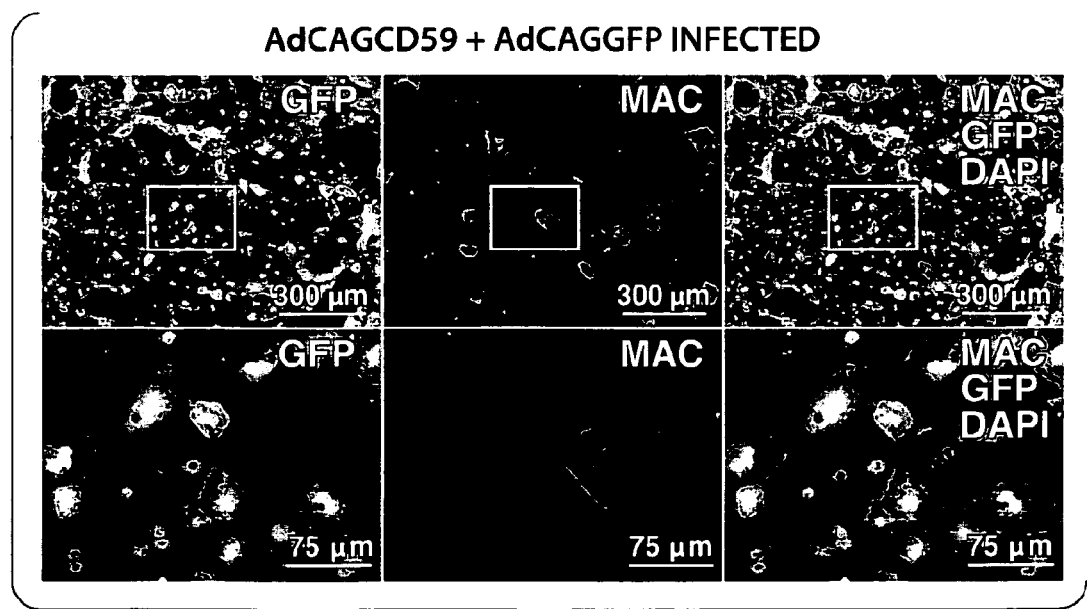

FIG. 10 is a set of photomicrographs of cells pre-treated with mixtures of control vectors and hCD59 expressing vectors.

FIG. 10 panel A shows primary mouse RPE cells pre-treated with a mixture of AdEMPTY+AdCAGGFP (4:1 ratio, total of 1×10³ vp/cell), then contacted three days post infection with anti-emmprin antibody and with 50% NHS for 7 minutes after washings and fixation. Cells were observed with DIC (left) or by GFP fluorescence (right).

FIG. 10 panel B shows primary mouse RPE cells pre-treated as in FIG. 10 panel A except with a mixture of AdCAGCD59+AdCAGGFP. Use of AdCAGGFP revealed vesicles (FIG. 10 panels A and B, arrows). The data show inhibition of MAC-associated vesiculation by adenovirus-mediated delivery of hCD59.

FIG. 11 is a set of photographs of dissected tissues, and a set of photomicrographs of these tissues to analyze cell data.

FIG. 11 panel A shows eyecup tissues pre-treated for six days by subretinal injection of either AdCAGCD59. Tissues were stained by immunohistochemistry for expression of CD59, and tissue fluorescence of GFP was detected directly. FIG. 11 panel B shows eyecup tissues as in FIG. 11 panel A, except pre-treated with control vector AdCAGGFP. FIG. 11 panel C shows cornea tissues were harvested from mice and pre-treated ex vivo for three days with either AdCAGCD59. FIG. 11 panel D shows cornea tissues as in FIG. 11 panel C except pre-treated with control vector AdCAGGFP.

Data from FIG. 11 panels A and C show expression of human CD59 by murine RPE and corneal endothelium following pre-treatment with AdCAGCD59. AdCAGCD59 and AdCAGGFP pre-treated corneas visualized with anti-CD59 antibody.

FIG. 12 is a set of photographs, photomicrographs and a bar graph of data from flatmounts of eyecups from eyes pretreated by injection with a mixture of control vectors AdEMPTY+AdCAGGFP, in FIG. 12 panel A, and vectors AdCAGCD59+AdCAGGFP in FIG. 12 panel B (9:1 ratio, 3×10⁸ vp/cell). Cells were contacted six days post-injection with the anti-mouse emmprin antibody followed by 50% NHS for 15 minutes. GFP (left in each set) shows fluorescence at the site of injection (1 mm length bar), and photomicrographs below are two magnifications of the site of injection (length bars 400 μm and 100 μm). MAC shows MAC staining with anti-human C5b-9 antibody, with photomicrographs below magnifications of the site of injection (as indicated by bars of length of 400 μm and 100 μm). Merge is an overlay of the GFP and the MAC dissected tissue photographs (1 mm magnification).

FIG. 12 panels A and B data show that MAC immunostaining of control tissues pretreated with a mixture of control vectors is substantial, and that MAC in control cells was significantly more extensive and stronger than the MAC at the area of GFP expression in tissues receiving injection of the mixture of AdCAGCD59 and AdCAGGFP (FIG. 12 panel B). RPE cells at the GFP expressing area of control injected eyecups were observed to be extensively damaged as indicated by rounded shape, loss of normal hexagonal morphology and loss of defined cell boundaries (FIG. 12 panel A middle row).

FIG. 12 panel B immunohistochemistry for human MAC was significantly reduced on the RPE at the area of GFP expression, correlating with human CD59 expression compared to the rest of the eyecup tissue. RPE cells at this area were observed to be undamaged with defined cell boundaries and normal hexagonal morphology.

FIG. 12 panel C graphs show eyecup tissues contacted with serum for either 7.5 minutes (left graph) or 15 minutes (right graph). Serum was HI-NHS (open bars) or NHS (closed bars). The four types of tissues: uninjected/not pretreated with adenovirus and contacted with HI-NHS (Uninjected, open bar first from the left), uninjected/not pretreated with adenovirus and contacted with NHS (Uninjected, closed bar second from left), tissues injected with a mixture of control adenovirus and contacted with NHS (EMPTY+GFP, closed bar second from the right), tissues injected with a mixture of AdCAGCD59+AdCAGGFP adenovirus and contacted with NHS (CD59+GFP, closed bar first from the right). Data expressed as means±s.e.m. *p<0.01, p<0.001, *p<0.0001 show at both treatment periods that CD59 pre-treated cells had lower levels of MAC.

FIG. 12 panel D is a set of photomicrographs of primary RPE cells injected with a mixture of control vectors (AdEMPTY+AdCAGGFP), then treated with the anti-mouse emmprin antibody followed by 50% NHS for 15 minutes at 37° C. six days post-injection. Images are representative of three separate experiments.

FIG. 12 panel E shows primary RPE cells as in FIG. 12 panel D but injected with a mixture of hCD59 expressing vectors (AdCAGCD59+AdCAGGFP). Significantly less MAC deposition was observed than in comparable cells in FIG. 12 panel D.

Figure 13A:
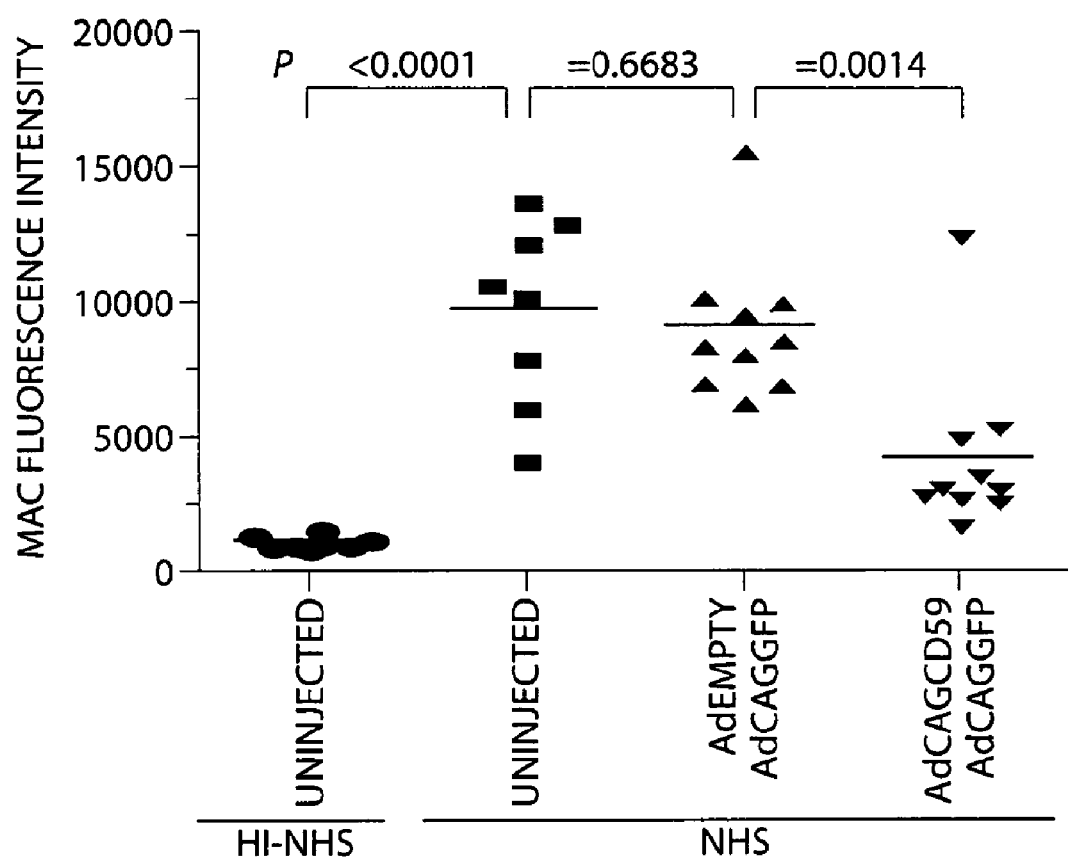
Figure 13B:
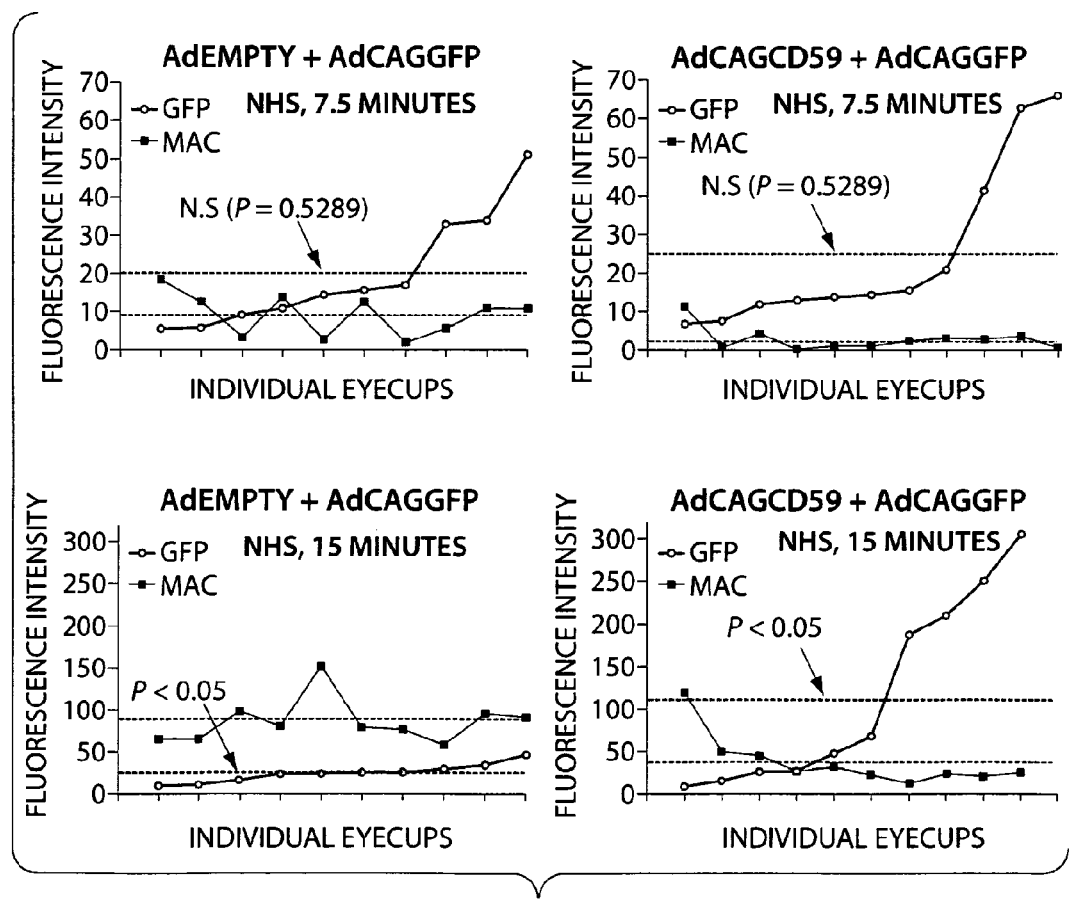
Figure 14A:
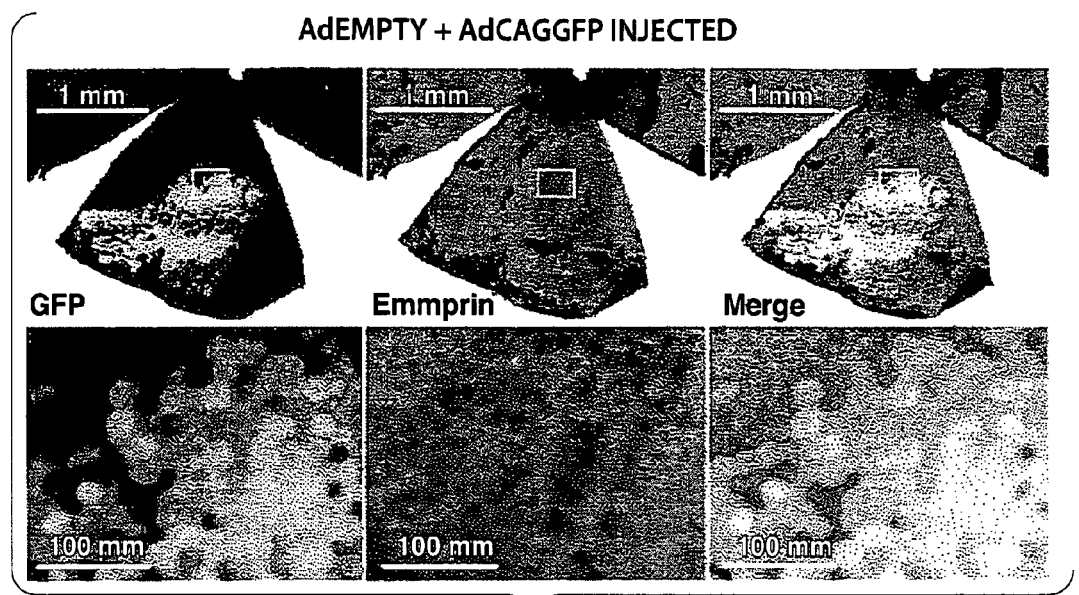
Figure 14B:
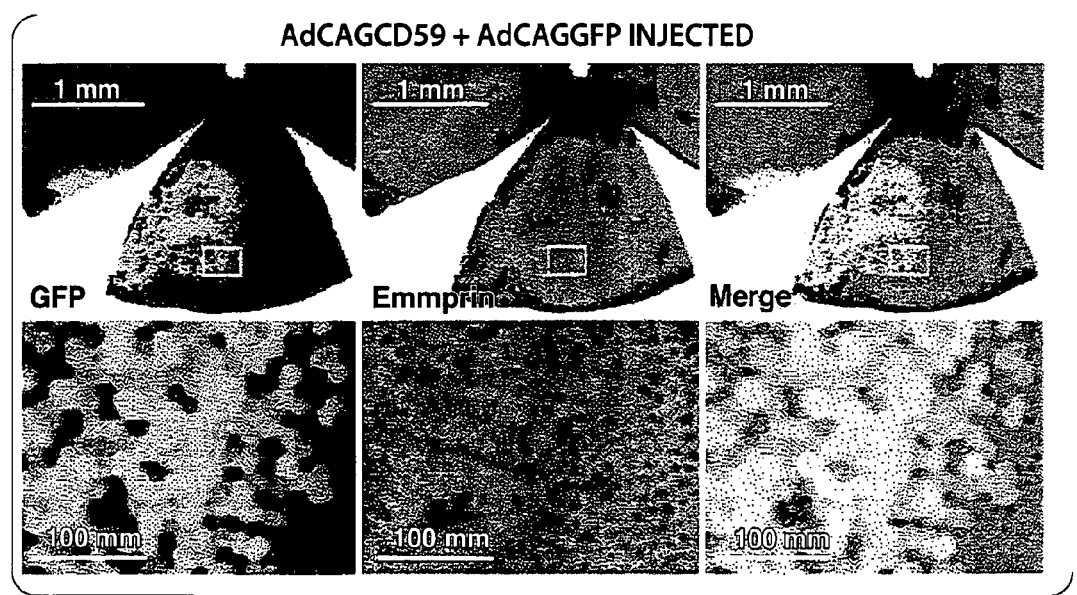
Figure 14C:
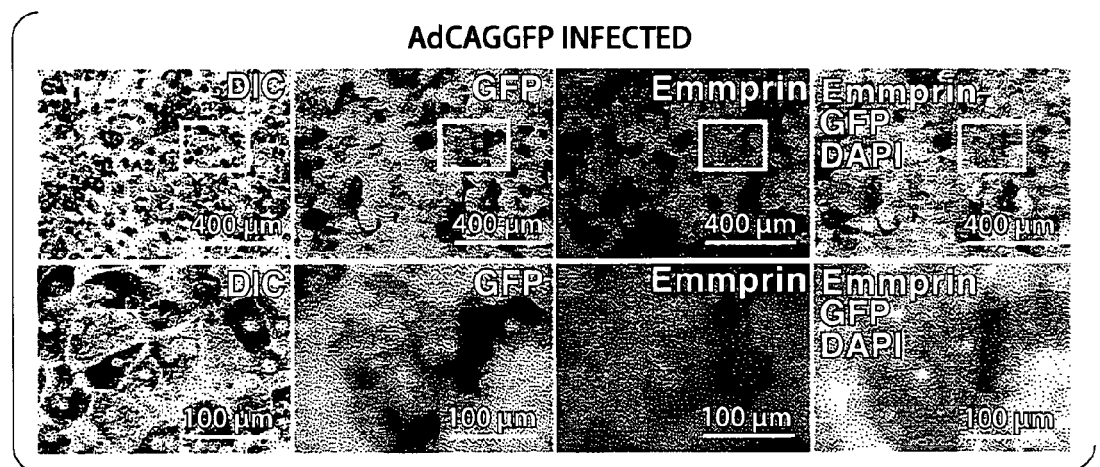
Figure 14D:
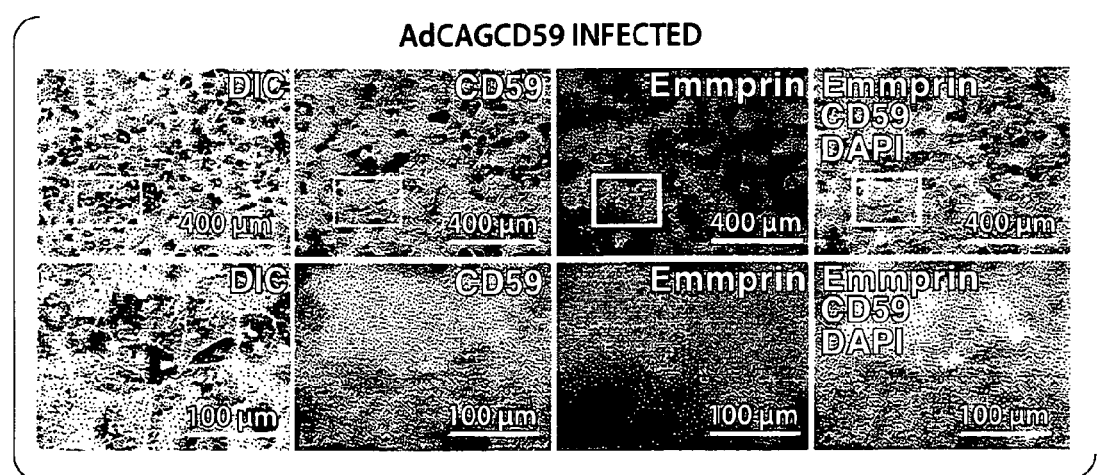

FIG. 13 panel A is a graph showing quantification of the MAC immunofluorescence at the area of GFP expression with MAC fluorescence intensity on the ordinate and nature of injected material to which RPE cells were pretreated on the abscissa. Control cells contacted with NHS have a MAC fluorescence intensity between 5,000 and 15,000, with a median of about 10,000. In contrast, control cells contacted with HI-NHS have a MAC fluorescence intensity of less than 2,500. RPE cells pretreated a mixture of AdEMPTY and AdCAGGFP and contacted with NHS have a MAC fluorescence intensity between 6,000 and 10,000, with a median of about 9,000. RPE cells pretreated with a mixture of AdCAGCD59 and AdCAGGFP and contacted with NHS have a MAC fluorescence intensity between 2,000 and 11,000, with a median less than 5,000 due to one out-lying point. This data show an overall reduction of about 55% in mean MAC fluorescence intensity for AdCAGCD59 and AdCAGGFP injected eyecup tissues (n=10) compared to control injected eyecup tissues (n=10), which was statistically significant (p=0.0014, FIG. 13 panel A).

FIG. 13 panel B is a line graph of quantification of fluorescence intensity at the site of injection (ordinate) of individual eyecup tissues (abscissa). Both GFP fluorescence and MAC immunofluorescence intensity at the area of GFP expression are shown for eyecups from eyes injected with mixtures of control (AdEMPTY+AdCAGGFP, left) vectors or hCD59 expressing vector (AdCAGCD59+AdCAGGFP, right). Length of serum treatment is indicated. The data points are the GFP or MAC fluorescence intensity from one eyecup, arranged from left to right in the order of increasing GFP fluorescence intensity. Lines are the means for each set of data. An inverse relationship was observed between GFP and MAC fluorescence intensities on the AdCAGCD59+AdCAGGFP-pretreated eyecups contacted with NHS. The symbol N.S. signifies that the differences are not statistically significant.

FIG. 14 is a set of photographs and photomicrographs showing immunochemistry data for RPE cells pretreated with control mixture of AdEMPTY and AdCAGGFP (FIG. 14 panel A) or a mixture of AdCAGCD59 and AdCAGGFP (FIG. 14 panel B). Six days post-infection with the indicated adenovirus mixtures, cells were contacted with first primary goat anti-mouse emmprin antibody followed by first secondary Cy3-conjugated donkey anti-goat IgG antibody. GFP shows fluorescence at the site of injection, and below are two magnifications at site of injection. Emmprin shows emmprin immunofluorescence, and two magnifications at the site of injection. Merge is an overlay of the GFP and the emmprin. Images are representative of three separate experiments. Data in FIG. 14 panels A and B show no significant difference in emmprin iummnofluoresence between the area of transgene expression and the rest of the eyecup or ininjected eyecups.

FIG. 14 panel C shows data for RPE cells pretreated by injection with AdCAGGFP. Three days later cells were contacted with first primary goat anti-mouse emmprin antibody followed by first secondary Cy3-conjugated donkey anti-goat IgG antibody, washed, fixed, and were incubated with the second primary-mouse anti-hCD59 antibody followed by second secondary-Cy2-conjugated goat anti-mouse IgG antibody. Cell nuclei were labeled with DAPI and visualized by DIC, GFP, and Emmprin. Images are representative of three separate experiments.

FIG. 14 panel D shows results for RPE cells pretreated by injection as in FIG. 14 panel C except with AdCAGCD59, and immunochemistry was as above. Data in FIG. 14 panels C and D show that no significant change in emmprin was observed due to expression of hCH59 (compared to GFP).

Figure 15:
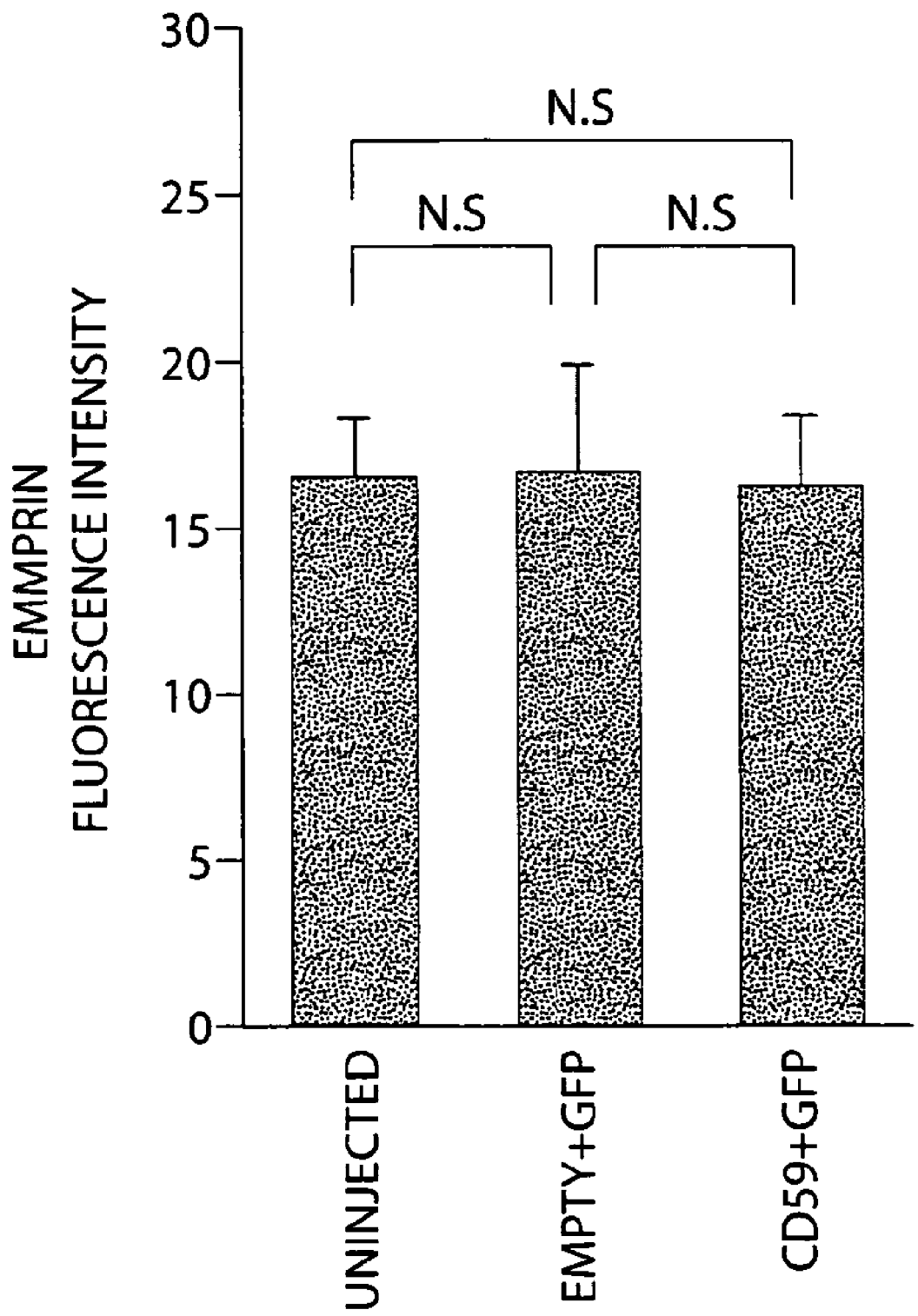

FIG. 15 is a bar graph showing emmprin immunofluorescence (ordinate) by RPE cells that were pretreated with vectors (as shown on the abscissa) before emmprin immunostaining. The RPE cells shown were control not pretreated (left bar), pretreated with a mixture of control vectors (EMPTY+ AdCAGGFP; middle bar), and a mixture of hCD59 expressing vector and GFP (CD59+GFP, right bar). For each group, 12 images (acquired with a 40× objective) from three eyecups were quantified. Graph includes data obtained from experiments shown in FIG. 14 panels A and B. Data are expressed as means±s.e.m. The data show that there was no effect on emmprin staining by the pretreatments.

Figure 16:
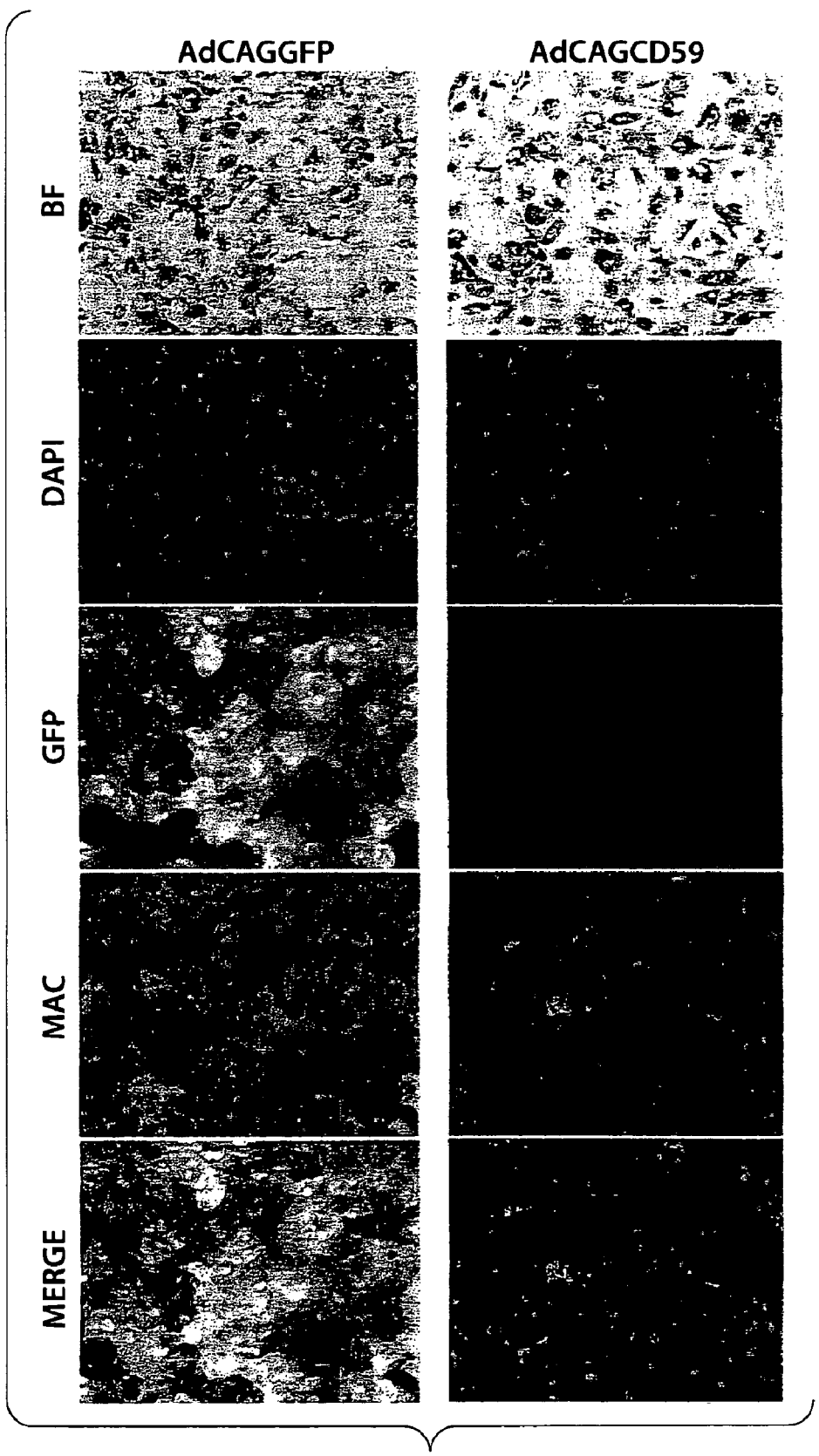
Figure 17A:
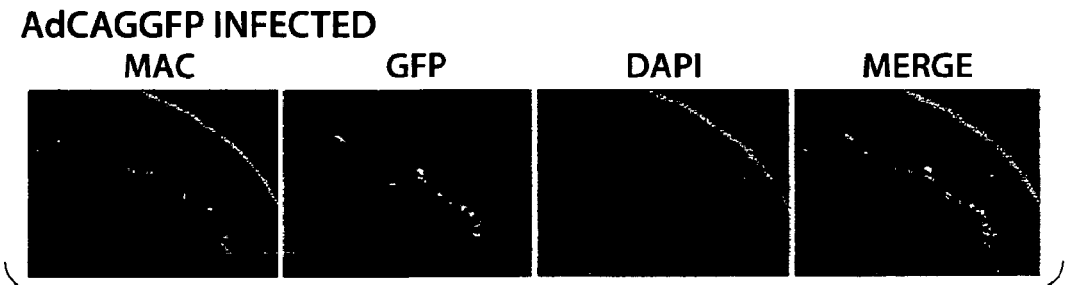
Figure 17B:
Figure 17C:
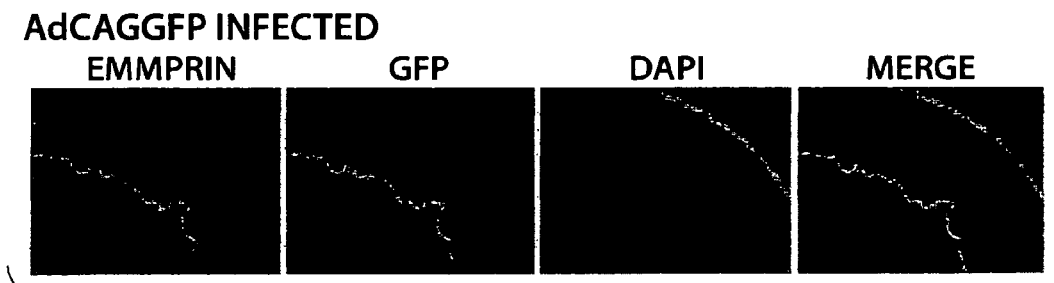
Figure 17D:
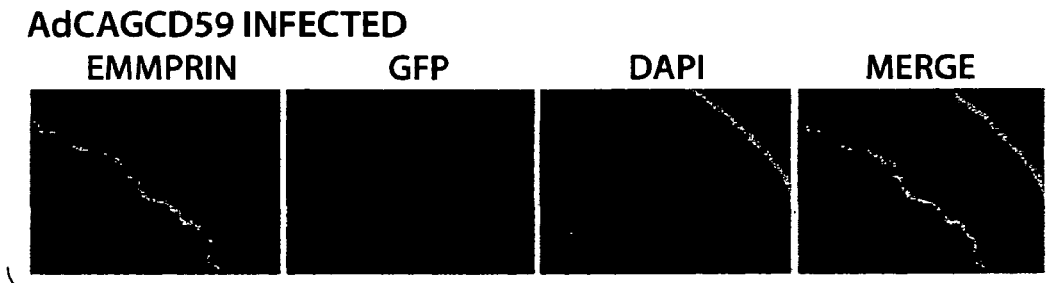
Figure 18A:
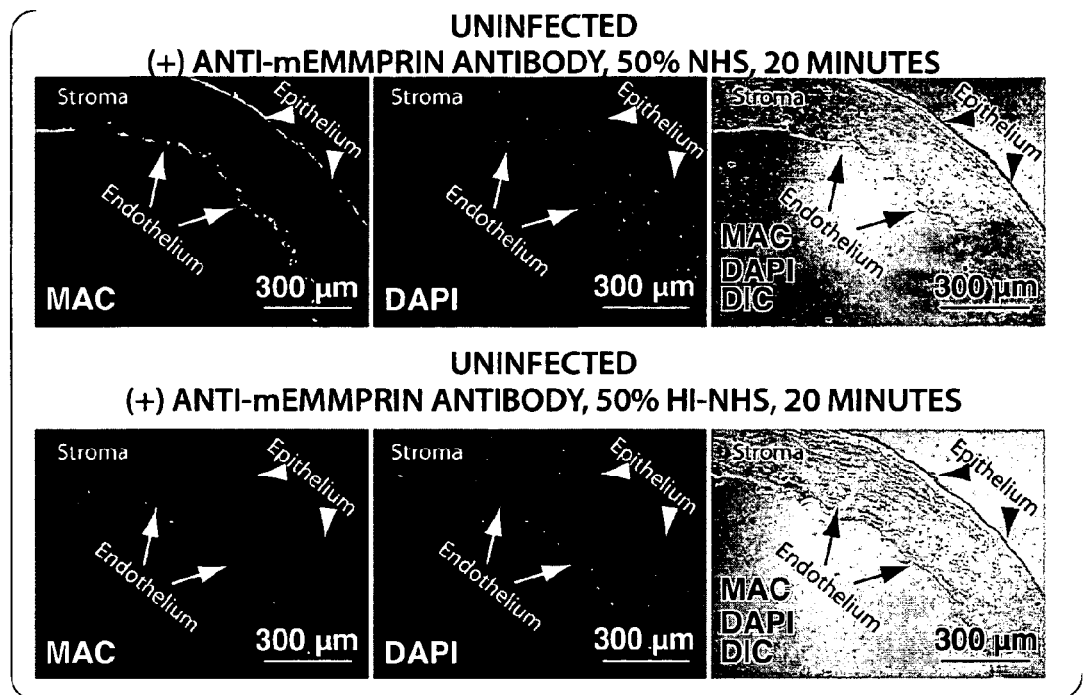
Figure 18B:
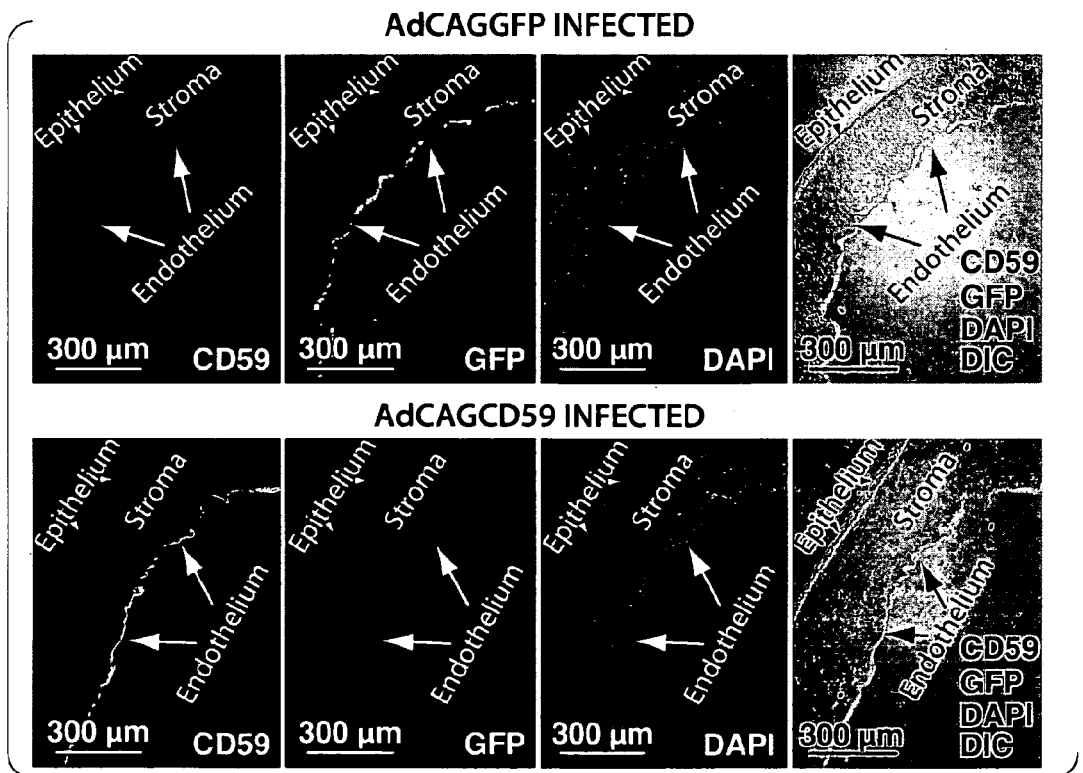
Figure 18C:
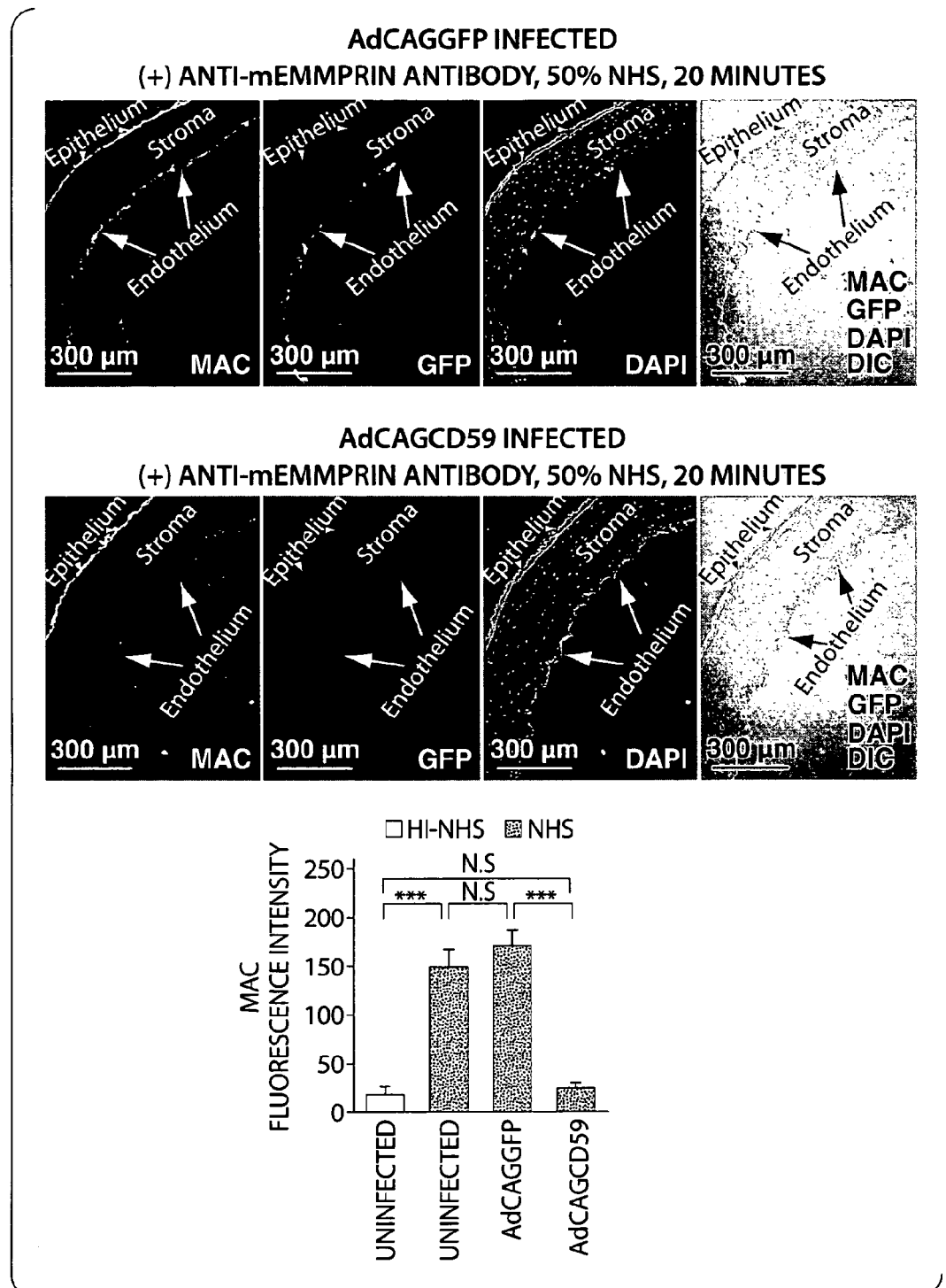
Figure 18D:
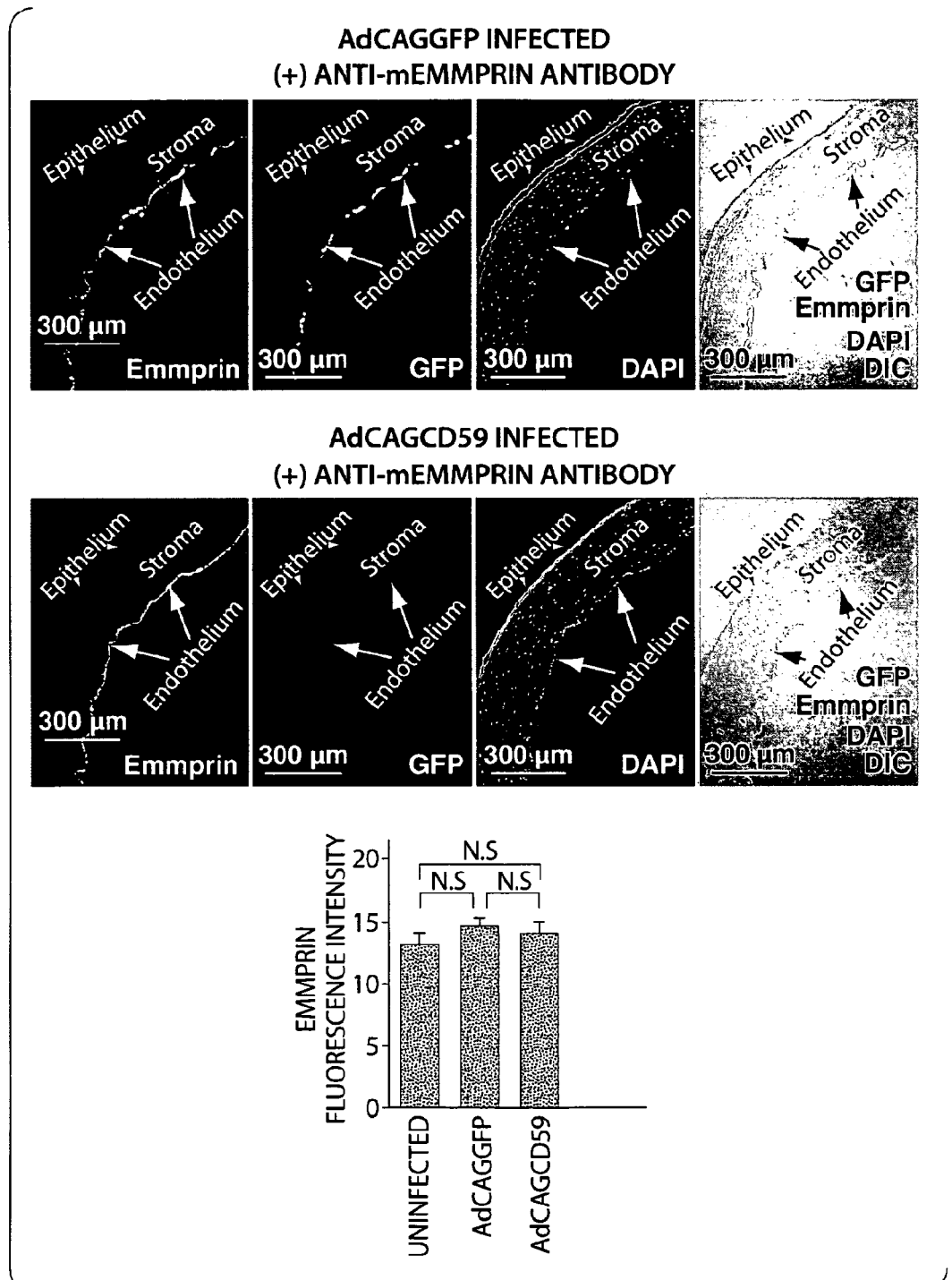

FIG. 16 is a set of photographs of primary mouse RPE cells three days after pretreatment. RPE cells were pretreated with AdCAGGFP (left column) or with AdCAGCD59 (right column). Pigmentation of RPE cells pretreated with AdCAGGFP (BF photograph, left column) was observed to be similar to pigmentation of cells pretreated with AdCAGCD59 (BF photograph, right column). RPE cells pretreated with AdCAGGFP and stained with DAPI showed the same amount of fluorescence (DAPI photograph, left column) compared to RPE cells pretreated with AdCAGCD59 and stained with DAPI (DAPI photograph, right column). RPE cells pretreated with AdCAGGFP showed significantly greater green fluorescence (GFP photograph, left column) compared to RPE cells pretreated with AdCAGCD59 (GFP photograph, right column). RPE cells pretreated with AdCAGGFP followed by anti-mouse emmprin antibody and NHS showed significantly greater MAC immunofluorescence (MAC photograph, left column) compared to RPE cells pretreated with AdCAGCD59 followed by the same anti-mouse emmprin and NHS treatment and detected by anti-human MAC antibody (MAC photograph, right column).

FIG. 17 panel A is a set of photographs showing a section from a cornea pretreated with a control AdCAGGFP and followed by anti-mouse emmprin antibody and NHS. The photograph labeled MAC shows MAC immunostaining with anti-MAC antibody on the endothelium of this cornea. The photograph labeled GFP shows GFP fluorescence on the corneal endothelium. The photograph labeled DAPI shows labeled DNA fluorescence of the corneal cells. The photograph labeled merge shows an overlay of the previous photographs.

FIG. 17 panel B is a set of photographs showing cells pretreated with AdCAGCD59 followed by the same anti-mouse emmprin and NHS treatment as the cornea in FIG. 17 panel A. The photograph labeled MAC shows MAC immunostaining on the endothelium of this cornea. The photograph labeled GFP shows absence of GFP fluorescence by these cells. The photograph labeled DAPI shows labeled DNA fluorescence of the corneal cells. The photograph labeled merge shows an overlay of the previous photographs.

FIG. 17 panel C is a set of photographs showing cells pretreated with a control AdCAGGFP. The photograph labeled emmprin shows emmprin antibody immunostaining of these cells. The photograph labeled GFP shows direct GFP fluorescence by these cells. The photograph labeled DAPI shows labeled DNA fluorescence of these cells. The photograph labeled merge shows an overlay of the previous photographs.

FIG. 17 panel D is a set of photographs showing cells pretreated with AdCAGCD59. The photograph labeled emmprin shows emmprin antibody immunostaining of these cells. The photograph labeled GFP shows direct GFP fluorescence by these cells. The photograph labeled DAPI shows labeled DNA fluorescence of these cells. The photograph labeled merge shows an overlay of the previous photographs.

These photographs show that protection from MAC on the corneal endothelium of AdCAGCD59 pretreated corneas (FIG. 17 panels B and D) was not due to a difference in emmprin expression or anti-emmprin antibody binding, as immunohistochemistry showed no differences in emmprin immunostaining of the corneal endothelium between AdCAGCD59 and AdCAGGFP contacted corneas (FIG. 17 panel C, emmprin photograph compared to FIG. 17 panel D, emmprin photograph). These photographs further show significant reduction in MAC immunostaining on the corneal endothelium of AdCAGCD59 pretreated corneas (FIG. 17 panel B, MAC photograph) compared to MAC immunostaining on the corneal endothelium of AdCAGGFP pretreated corneas (FIG. 17 panel A, MAC photograph).

FIG. 18 is a set of photographs and bar graphs of corneas injected ex vivo with AdCAGGFP or AdCAGCD9 vectors and treated with or without emmprin antibody and NHS or HI-NHS, the bar graphs showing each of MAC and emmprin fluorescence intensity.

FIG. 18 panel A shows emmprin in control corneas not pretreated with vector and contacted with anti-mouse emmprin antibody then with NHS (top row) or HI-NHS (bottom row). MAC staining (red in original not shown here), DAPI (blue in original) and DIC for these corneas were observed. Bright MAC immunostaining was observed on corneal endothelia of the corneas treated with NHS and minimal staining on the corneal endothelia treated with HI-NHS.

FIG. 18 panel B shows an immunohistochemical analysis similar to that in FIG. 18) panel A, but of corneas pretreated for three days with AdCAGGFP or AdCAGCD59 adenovirus (top row and bottom row respectively, $1.5 \times 10^9$ vp). No CD59 expression was observed for the corneas pretreated with the AdCAGGFP adenovirus (top), and strong CD59 expression was observed for corneas pretreated with adCADCD59 adenovirus (bottom).

FIG. 18 panel C shows corneas pretreated with AdCAG-GFP (top) or AdCAGCD59 (bottom) adenovirus, treated with 25 µg/ml goat anti-mouse emmprin antibody and with NHS (top row) or HI-NHS (bottom). The bar graph in FIG. 18 panel C shows quantification of MAC immunofluorescence (ordinate) on the corneal endothelium of twelve sections from four corneas groups in each group pretreated with or without adenovirus (abscissa). The groups include: control (not pretreated, indicated uninfected in the figure) corneas that were contacted with serum, (AdCAGGFP) corneas pretreated with AdCAGGFP adenovirus before contact with serum, and (AdCAGCD59) corneas pretreated with ADCAGCD59 adenovirus before contact with serum. The corneas groups were then exposed either to NHS (solid bars) or HI-NHS (open bars). Graph includes data shown in FIG. 18 panels A and C. Extensive MAC staining was observed for corneas pretreated with AdCAGGFP adenovirus and contacted with NHS. ***$p<0.0001$, N.S., not significant. The data show that MAC in corneas pretreated with CD59 was as low as that of control corneas.

FIG. 18 panel D shows corneas pretreated with of AdCAG-GFP (top row) or AdCAGCD59 (bottom row) adenovirus, and treated only with goat anti-mouse emmprin antibody. These corneas were not treated with NHS or HI-NHS as in FIG. 18 panel C. Emmprin expression, GFP fluorescence, DAPI and DIC staining are shown for these corneas at 300 μm magnification. The bar graph in FIG. 18 panel D shows quantification of MAC immunofluorescence (ordinate) on the corneal endothelium of twelve sections from four corneas groups in each group pretreated with or without vectors (abscissa). The groups include: corneas not pretreated with a vector before contact with NHS (indicated uninfected), corneas pretreated with AdCAGGFP adenovirus before treatment with NHS, and (AdCAGCD59) corneas pretreated with ADCAGCD59 adenovirus before treatment with NHS. Graph comprises data from experiments shown in FIG. 18 panel D and data not shown. Cell nuclei on all corneal sections were labeled with DAPI. All images are representative of sections obtained from four corneas for each group of infection or treatment. N.S., not significant. The data show no significant differences in emmprin among the groups of corneas.

Figure 19:
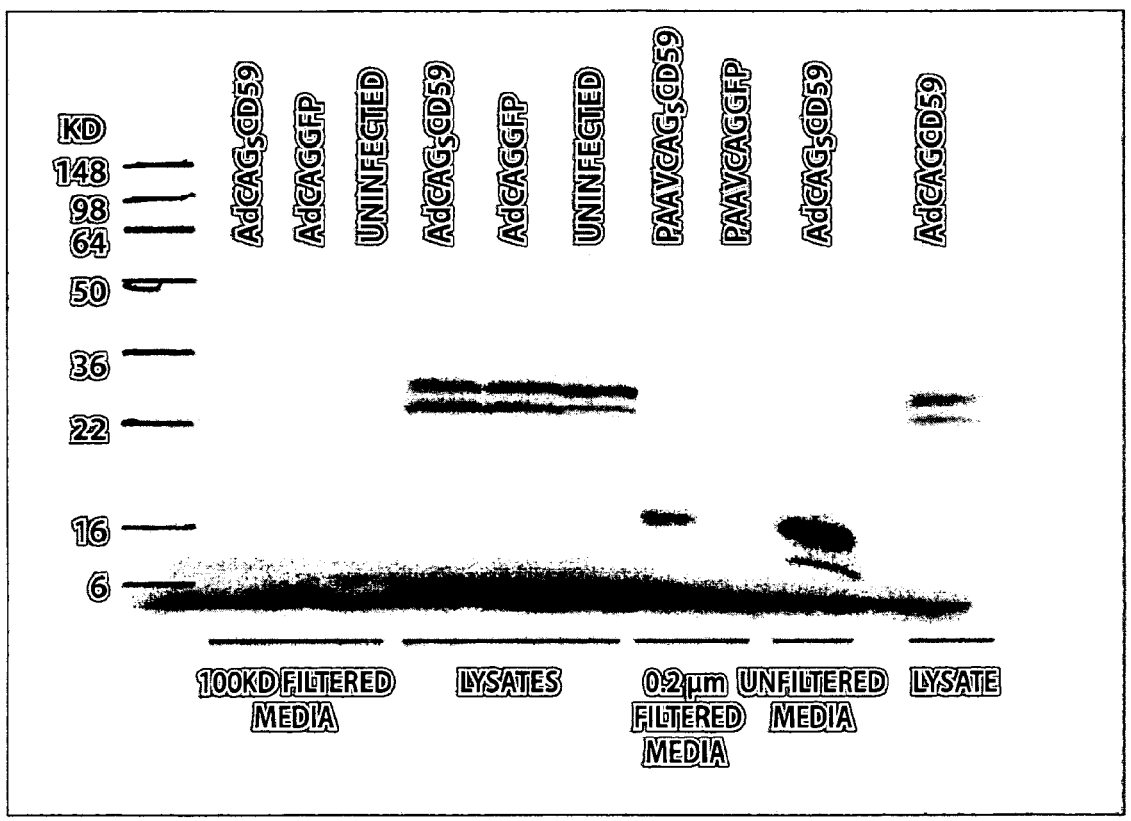

FIG. 19 is a photograph of a western blot of cells pretreated with each of a variety of vectors as indicated, with samples visualized with anti-Cd59 antibody. Human CD59 was observed in a sample of unfiltered media from cells pretreated with AdCAG$_S$CD59 (dark band at approximately 16 kD, second channel from the right indicated CAG$_S$CD59), a vector that expresses a soluble CD59 from which the glycosyl phosphatidyl inositol (GPI) linker had been removed. AdCAG$_S$CD59 thus was constructed to express a soluble and secreted version of the CD59 construct used in examples above that is membrane associated (AdCAGCD59/Lysate, first channel on the right). Molecular weight markers (6 to 148 KDa) are shown in the left channel. Cells were pretreated with plasmids (indicated p) or adenovirus vectors (indicated Ad). Controls were cells not pretreated with either plasmids or vectors (indicated Uninjected), pretreated with the membrane bound CD59 construct (CAGCD59), or pretreated with GFP expressing construct (CAGGFP). Samples were taken of media that were then filtered using a 100 kDa filter, or a 0.2 μm filter, or were unfiltered media, or were lysates. CD59 signal was not detected in lysates from unpretreated cells (sixth channel from the left).

DETAILED DESCRIPTION

Analysis of polymorphisms in several complement regulatory proteins including Factor H have implicated over-active complement in the pathogenesis of AMD (Hageman et al. Proc Natl Acad Sci USA, 102:7227-7232, 2005; Klein et al. Science, 308:385-389, 2005; and Haines et al., Science, 308: 419-421, 2005; Edwards et al., Science, 308:421-424, 2005). Immunohistochemical analysis of drusen, which are yellow deposits under the retina, and retinal pigment epithelium (RPE) from AMD patients indicated the presence of a variety of complement proteins including the membrane attack complex (MAC). However, cross-species differences between human and non-human complement systems have limited ability to, test the efficacy of human complement regulatory proteins in non-human systems in vivo.

Provided herein is a humanized murine model for measuring human MAC deposition in vitro and in vivo. Examples herein use this model to measure protection by human CD59 of murine RPE, the pigmented cell layer just outside the neurosensory retina that nourishes retinal visual cells, from attack by human MAC. Using this model, local expression of exogenously delivered human complement regulatory protein CD59 was found to protect the RPE from human MAC deposition in vivo. Such protection of the RPE by CD59 indicates that this protection can prevent or treat AMD. The humanized model of MAC deposition on murine retina allows for safe and rapid testing of human complement proteins in vivo.

The complement system, a component of the overall immune system of an organism, is a biochemical cascade that assists clearing of pathogens within an organism. The complement system includes a number of small proteins found circulating in blood, usually as inactive zymogens. Stimulated by one of several triggers, proteases in the system cleave specific proteins to release cytokines and initiate an amplifying cascade of further cleavages. Activation of this biochemical cascade results in activation of MAC, a function for killing pathogens.

The complement system is classified into a set of differently activated pathways: the classical complement pathway, the alternative complement pathway, and the mannose-binding lectin pathway. These pathways generate homologous variants of a protease, the C3-convertase. The classical complement pathway typically involves antibodies for activation (specific immune response), while the alternative and mannose-binding lectin pathways are activated by C3 hydrolysis or antigens without the presence of antibodies (non-specific immune response).

In these pathways, a C3-convertase cleaves and activates component C3, creating C3a and C3b and causing a cascade of further cleavage and activation events. One such activation event initiates component C5b. Activation of C5b initiates the membrane attack pathway, which results in formation of MAC, a cytolytic endproduct of the complement cascade that forms a transmembrane channel and causes osmotic lysis of target cells.

MAC is formed for example, on the surface of intruding pathogenic bacterial cells as a result of activation of the complement system. MAC is a complex of four complement system proteins (C5b, C6, C7, and C8) that bind to the outer surface of a plasma membrane of a target cell, and with a fifth protein (C9) that binds subsequently (Sims et al., U.S. Pat. No. 7,166,568). The complement proteins bind together in such a conformation that an external face of the proteins is hydrophobic and associates with the lipid bilayer of the membrane of the target cell, while an internal face is hydrophilic, allowing passage of water through the cell. The proteins form a ring through the membrane of the cell and the ring structure acts as a tunnel through the membrane, allowing free diffusion of molecules through the cell which disrupts the internal environment of the cell killing it quickly.

CD59 Protein

Data in Examples herein show that CD59 acts to inhibit MAC, preventing lysis of retina cells. CD59 is a membrane-bound glycoprotein found associated with membranes of cells including human erythrocytes, lymphocytes, and vascular endothelial cells. CD59 protein inhibits assembly of functional MACs and thus protects cells from complement-mediated activation and/or lysis.

Without being limited by any particular theory or mechanism of action, it is here envisioned that plasma membranes of cells are normally protected from the effects of complement by cell-surface proteins, e.g., CD59, that specifically inhibit activation of the C5b-9 pore upon C9 complement protein binding to membrane C5b-8 (Holguin, et al., J. Clin. Invest. 84, 7 17, 1989; Sims et al., J. Biol. Chem. 264, 19228 19235, 1989; Davies, et al., J. Exp. Med. 170, 637 654, 1989; Rollins et al. J. Immunol. 144, 3478 3483, 1990; and Hamilton et al., Blood 76, 2572 2577, 1990). CD59 appears to function by competing with C9 complement protein for binding to C8 complement protein in the C5b-8 complex, thereby decreasing or preventing the formation of the C5b-9 membrane attack complex (Rollins et al., 1990). CD59 thus acts to reduce both cell activation and cell lysis by terminal complement MACs.

Mature human CD59 protein is composed of 77 amino acids and has a molecular weight of 1810. Precursor human CD59 protein has a molecular weight of 2110. Amino acid sequences of precursor human CD59, a mature human CD59, and CD59 of other mammals, e.g., baboon, African green monkey, owl monkey, marmoset, HVS-15, pig, rabbit, rat, and mouse, are shown in Sims et al. (U.S. Pat. No. 7,166,568, issued Jan. 23, 2007).

The protein structure of CD59 is characterized as a single cysteine-rich domain, having a hydrophobic core with three loops and a small fourth helical loop (Yu et al., Journal of Experimental Medicine, 185(4):745-753, 1997). Disulfide-bonded cysteine pairs connect each of these loops (Yu et al., 1997).

The structure of the gene encoding CD59 has been characterized (Fodor et al. U.S. Pat. No. 5,624,837, issued Apr. 29, 1997). The gene is located on the short arm of chromosome 11 in humans, specifically chromosome 11p13 and 11p14 (Online Mendelian Inheritance in Man accession number and 107271), and consists of 4 exons spanning 20 kb (Petranka et al. Proc. Nat. Acad. Sci. 89:7876-7879, 1992). An untranslated first exon is preceded by a G and C-rich promoter region that lacks a consensus TATA or CAAT motif. The second exon encodes the hydrophobic leader sequence of the protein, and the third exon encodes the N-terminal portion of the mature protein. The fourth exon encodes the remainder of the mature protein, including the hydrophobic sequence for glycophosphoinosital anchor attachment to a cell membrane.

Analysis of the physical association of CD59 with components of MAC show that separate binding sites for CD59 are contained within the α-chains of each of human C8 and human C9 (Sims et al.). The binding site for interactions of human CD59 with human C9 has been identified as amino acid residues 42 to 58 in the sequence of mature human CD59, that bind to the region of human C9 corresponding to human amino acid residues 334 to 418 of that protein, more particularly human C9 amino acid residues 359 to 384, immediately C-terminal to the predicted membrane-inserting domain of C9 (PCT/US96/17940 "C9 Complement Inhibitor" by Oklahoma Medical Research Foundation; Sims et al.).

The active surface exposed amino acid residue side chains that are available to bind C8/C9, identified from solution structure of mature human CD59 from published NMR data and the knowledge of the active portion of the CD59 molecule, are histidine at position 44, asparagine at position 48, aspartic acid at position 49, threonine at positions 51 and 52, arginine at position 55, and glutamic acid at position 58. NMR structures for CD59 are described in deposits by Kieffer et al., Human Complement Regulatory Protein CD59 (Extracellular Region, Residues 1 70; NMR, 10 Structures), MMDB Id: 891, PDB Id: 1ERH; Kieffer et al., Human Complement Regulatory Protein CD59 (Extracellular Region, Residues 1 70; NMR, Restrained), MMDB Id: 890, PDB Id: 1ERG; Fletcher et al., CD59 Complexed With Glcnac-Beta-1,4-(Fuc-Alpha-1,6)-Glcnac-Beta-1 (NMR, 10 Structures), MMDB Id: 498, PDB Id: 1CDS; Fletcher et al., CD59 Complexed With Glcnac-Beta-1,4-Glcnac-Beta-1 (NMR, 10 Structures), MMDB Id: 497, PDB Id: 1 CDR. The 1 CDS and 1 CDR deposits by Fletcher et al. Amino acid sequences of CD59 that present these side chains at the same relative positions function in a manner similar to human CD59 (Sims et al.), and such variants are within the scope of the methods, kits and pharmaceutical compositions herein.

Thus in certain embodiments, the CD59 protein includes conservative sequence modifications. As used herein, the term "conservative sequence modifications" refers to amino acid modifications that do not significantly affect or alter the characteristics of the CD59 protein containing the amino acid sequence, i.e., amino acid sequences of CD59 that present these side chains at the same relative positions will function in a manner similar to human CD59. Such conservative modifications include amino acid substitutions, additions and deletions. Modification of the amino acid sequence of CD59 is achieved using any known technique in the art e.g., site-directed mutagenesis or PCR based mutagenisis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In certain embodiments, the CD59 amino acid sequence is an amino acid sequence that is substantially identical to that of the wild type sequence. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 85%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., *Nuc. Acids Research* 22:4673, 1994 (www.ebi.ac.uk/clustalw), BL2SEQ by Tatusova and Madden, *FEMS Microbiol. Lett.* 174:247, 1999 (www.ncbi.nlm.nih.gov/blast/b12seq/b12.html), SAGA by Notredame and Higgins, *Nuc. Acids Research* 24:1515, 1996 (igs-server.cnrs-mrs.fr/~cnotred), and DIALIGN by Morgenstern et al., *Bioinformatics* 14:290, 1998 (bibiserv.techfak.uni-bielefeld.de/dialign).

Vectors

In various embodiments of the invention herein, a method for treating AMD is provided, the method including contacting cells or tissue with a pharmaceutical composition including a source of CD59 protein or as a source of CD59 expression in vivo. For example, the CD59 protein is administered as a recombinantly produced protein. The term "recombinant" refers to proteins produced by manipulation of genetically modified organisms, for example micro-organisms.

In accordance with the present invention a source of CD59 includes polynucleotide sequences that encode the CD59 protein, for example, engineered into recombinant DNA molecules to direct expression of the CD59 protein in appropriate host cells. To express a biologically active CD59 protein, a nucleotide sequence encoding the CD59 protein, or functional equivalent, is inserted into an appropriate expression vector, i.e., a vector that contains the necessary nucleic acid encoding elements that regulate transcription and translation of the inserted coding sequence, operably linked to the nucleotide sequence encoding the CD59 protein amino acid sequence.

Methods that are well known to those skilled in the art are used to construct expression vectors containing a sequence encoding the CD59 protein operably linked to appropriate transcriptional and translational control elements. These methods include in vitro recombinant DNA techniques, synthetic techniques and in vivo recombination or genetic recombination. Such techniques are described in Sambrook et al., Molecular Cloning: A Laboratory Manual, Cold Spring Harbor Press, Plainview, N.Y., 1989.

A variety of commercially available expression vector/host systems are useful to contain and express a CD59 protein encoding sequence. These include but are not limited to microorganisms such as bacteria transformed with recombinant bacteriophage, plasmid or cosmid DNA expression vectors; yeast transformed with yeast expression vectors; insect cell systems contacted with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. See Ausubel et al., Current Protocols in Molecular Biology, John Wiley & Sons, New York, N.Y., 1989.

Virus vectors include, but are not limited to, adenovirus vectors, lentivirus vectors, adeno-associated virus (AAV) vectors, and helper-dependent adenovirus vectors. Virus vectors deliver a nucleic acid sequence that encodes CD59 protein that as shown herein interferes with the deleterious action of the MAC in pathogenesis of AMD. Adenovirus packaging vectors are commercially available from American Type Tissue Culture Collection (Manassas, Va.). Methods of constructing adenovirus vectors and using adenovirus vectors are shown in Klein et al., Opthalmology, 114:253-262, 2007 and van Leeuwen et al., Eur. J. Epidemiol., 18:845-854, 2003.

Adenovirus vectors have been used in eukaryotic gene expression (Levrero et al., Gene, 101:195-202, 1991) and vaccine development (Graham et al., Methods in Molecular Biology: Gene Transfer and Expression Protocols 7, (Murray, Ed.), Humana Press, Clifton, N.J., 109-128, 1991). Further, recombinant adenovirus vectors are used for gene therapy (Wu et al., U.S. Pat. No. 7,235,391).

Recombinant adenovirus vectors are generated, for example, from homologous recombination between a shuttle vector and a provirus vector (Wu et al., U.S. Pat. No. 7,235,391). The adenovirus vectors herein are replication defective, for example, are conditionally defective, lacking adenovirus E1 region, and a polynucleotide encoding CD59 is introduced at the position from which the E1-coding sequences have been removed. The polynucleotide encoding the CD59 gene alternatively is inserted in the E3 region, or is inserted in an E4 region using a helper cell line.

Helper cell lines may be derived from human cells such as, 293 human embryonic kidney cells, muscle cells, hematopoietic cells or other human embryonic mesenchymal or epithelial cells. Alternatively, the helper cells may be derived from the cells of other mammalian species that are permissive for human adenovirus, e.g., Vero cells or other monkey embryonic mesenchymal or epithelial cells. Generation and propagation of these replication defective adenovirus vectors using a helper cell line is described in Graham et al, J. Gen. Virol., 36:59-72, 1977.

Lentiviral vector packaging vectors are commercially available from Invitrogen Corporation (Carlsbad Calif.). An HIV-based packaging system for the production of lentiviral vectors is prepared using constructs in Naldini et al., Science 272: 263-267, 1996; Zufferey et al., Nature Biotechnol., 15: 871-875, 1997; and Dull et al., J. Virol. 72: 8463-8471, 1998.

A number of vector constructs are available to be packaged using a system, based on third-generation lentiviral SIN vector backbone (Dull et al., J. Virol. 72: 8463-8471, 1998). For example the vector construct pRRLsinCMVGFPpre contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the *Aequora* jellyfish green fluorescent protein (GFP) driven by the CMV promoter, and the woodchuck hepatitis virus PRE element, which appears to enhance nuclear export. The GFP marker gene allows quantitation of transfection or transduction efficiency by direct observation of UV fluorescence microscopy or flow cytometry (Kafri et al., Nature Genet., 17: 314-317, 1997 and Sakoda et al., J. Mol. Cell. Cardiol., 31: 2037-2047, 1999).

Manipulation of retroviral nucleic acids to construct a retroviral vector containing the gene that encodes for CD59 protein and packaging cells is accomplished using techniques known in the art. See Ausubel, et al., 1992, Volume 1, Section III (units 9.10.1-9.14.3); Sambrook, et al., 1989. Molecular Cloning: A Laboratory Manual. Second Edition. Cold Spring Harbor Laboratory Press, Cold Spring Harbor, N.Y.; Miller, et al., Biotechniques. 7:981-990, 1989; Eglitis, et al., Biotechniques. 6:608-614, 1988; U.S. Pat. Nos. 4,650,764, 4,861,719, 4,980,289, 5,122,767, and 5,124,263; and PCT patent publications numbers WO 85/05629, WO 89/07150, WO 90/02797, WO 90/02806, WO 90/13641, WO 92/05266, WO 92/07943, WO 92/14829, and WO 93/14188.

A retroviral vector is constructed and packaged into non-infectious transducing viral particles (virions) using an amphotropic packaging system. Examples of such packaging systems are found in, for example, Miller, et al., Mol. Cell. Biol. 6:2895-2902, 1986; Markowitz, et al., J. Virol. 62:1120-1124, 1988; Cosset, et al., J. Virol. 64:1070-1078, 1990; U.S. Pat. Nos. 4,650,764, 4,861,719, 4,980,289, 5,122,767, and 5,124,263, and PCT patent publications numbers WO 85/05629, WO 89/07150, WO 90/02797, WO 90/02806, WO 90/13641, WO 92/05266, WO 92/07943, WO 92/14829, and WO 93/14188.

Generation of "producer cells" is accomplished by introducing retroviral vectors into the packaging cells. Examples of such retroviral vectors are found in, for example, Korman, et al., Proc. Natl. Acad. Sci. USA. 84:2150-2154, 1987; Morgenstern, et al., Nucleic Acids Res. 18:3587-3596, 1990; U.S. Pat. Nos. 4,405,712, 4,980,289, and 5,112,767; and PCT patent publications numbers WO 85/05629, WO 90/02797, and WO 92/07943.

Herpesvirus packaging vectors are commercially available from Invitrogen Corporation, (Carlsbad, Calif.). Exemplary herpesviruses are an α-herpesvirus, such as Varicella-Zoster virus or pseudorabies virus; a herpes simplex virus such as HSV-1 or HSV-2; or a herpesvirus such as Epstein-Barr virus. A method for preparing empty herpesvirus particles that can be packaged with a desired nucleotide segment, for example a CD59 nucleotide or polynucleotide sequence, in the absence of a helper virus that is capable to most herpesviruses is shown in Fraefel et al. (U.S. Pat. No. 5,998,208, issued Dec. 7, 1999).

The herpesvirus DNA vector can be constructed using techniques familiar to the skilled artisan. For example, DNA segments encoding the entire genome of a herpesvirus is divided among a number of vectors capable of carrying large DNA segments, e.g., cosmids (Evans, et al., Gene 79, 9-20, 1989), yeast artificial chromosomes (YACS) (Sambrook, J. et al., MOLECULAR CLONING: A LABORATORY MANUAL, 2nd Edition, Cold Spring Harbor Press, Cold Spring Harbor, N.Y., 1989) or E. coli F element plasmids (O'Conner, et al., Science 244:1307-1313, 1989).

For example, sets of cosmids have been isolated which contain overlapping clones that represent the entire genomes of a variety of herpesviruses including Epstein-Barr virus, Varicella-Zoster virus, pseudorabies virus and HSV-1. See M. van Zijl et al., J. Virol. 62, 2191, 1988; Cohen, et al., Proc. Nat'l Acad. Sci. U.S.A. 90, 7376, 1993; Tomkinson, et al., J. Virol. 67, 7298, 1993; and Cunningham et al., Virology 197, 116, 1993.

AAV is a dependent parvovirus in that it depends on co-infection with another virus (either adenovirus or a member of the herpes virus family) to undergo a productive infection in cultured cells (Muzyczka, Curr Top Microbiol Immunol, 158:97 129, 1992). For example, recombinant AAV (rAAV) virus is made by co-transfecting a plasmid containing the gene of interest, for example, the CD59 gene, flanked by the two AAV terminal repeats (McLaughlin et al., J. Virol., 62(6): 1963 1973, 1988; Samulski et al., J. Virol, 63:3822 3828, 1989) and an expression plasmid containing the wild-type AAV coding sequences without the terminal repeats. Cells are also contacted or transfected with adenovirus or plasmids carrying the adenovirus genes required for AAV helper function. Recombinant AAV virus stocks made in such fashion include with adenovirus which must be physically separated from the recombinant AAV particles (for example, by cesium chloride density centrifugation).

Adeno-associated virus (AAV) packaging vectors are commercially available from GeneDetect (Auckland, New Zealand). AAV has been shown to have a high frequency of integration and infects nondividing cells, thus making it useful for delivery of genes into mammalian cells in tissue culture (Muzyczka, Curr Top Microbiol Immunol, 158:97 129, 1992). AAV has a broad host range for infectivity (Tratschin et al., Mol. Cell. Biol., 4:2072 2081, 1984; Laughlin et al., J. Virol., 60(2):515 524, 1986; Lebkowski et al., Mol. Cell. Biol., 8(10):3988 3996, 1988; McLaughlin et al., J. Virol., 62(6):1963 1973, 1988).

Methods of constructing AAV vectors and using AAV vectors are described, for example in U.S. Pat. Nos. 5,139,941 and 4,797,368. Use of AAV in gene delivery is further described in LaFace et al., Virology, 162(2):483 486, 1988; Zhou et al., Exp. Hematol, 21:928 933, 1993; Flotte et al., Am. J. Respir. Cell Mol. Biol., 7(3):349 356, 1992; and Walsh et al., J. Clin. Invest, 94:1440 1448, 1994.

Recombinant AAV vectors have been used successfully for in vitro and in vivo) transduction of marker genes (Kaplitt et al., Nat. Genet., 8(2):148 54, 1994; Lebkowski et al., Mol. Cell. Biol., 8(10):3988 3996, 1988; Samulski et al., EMBO J., 10:3941 3950, 1991; Shelling and Smith, Gene Therapy, 1: 165 169, 1994; Yoder et al., Blood, 82 (Supp.): 1:347 A, 1994; Zhou et al., Exp. Hematol, 21:928 933, 1993; Tratschin et al., Mol. Cell. Biol., 5:3258 3260, 1985; McLaughlin et al., J. Virol., 62(6):1963 1973, 1988) and transduction of genes involved in human diseases (Flotte et al., Am. J. Respir. Cell Mol. Biol., 7(3):349 356, 1992; Ohi et al., Gene, 89(2):279 282, 1990; Walsh et al., J. Clin. Invest, 94:1440 1448, 1994; and Wei et al., Gene Therapy, 1:261268, 1994).

Antibodies

The present invention relates also to diagnosing or prognosing presence or progression of macular degeneration by determining extent of MAC deposition on a retina by immunohistochemistry, using antibodies that are specific for human MAC. The term "antibody" as referred to herein includes whole antibodies and any antigen binding fragment (i.e., "antigen-binding portion") or single chains of these. A naturally occurring "antibody" is a glycoprotein including at least two heavy (H) chains and two light (L) chains interconnected by disulfide bonds.

As used herein, an antibody that "specifically binds to human MAC" is intended to refer to an antibody that binds to human MAC with a $K_D$ of $5 \times 10^{-9}$ M or less, $2 \times 10^{-9}$ M or less, or $1 \times 10^{-10}$ M or less. For example, the antibody is monoclonal or polyclonal. The terms "monoclonal antibody" or "monoclonal antibody composition" as used herein refer to a preparation of antibody molecules of single molecular composition. A monoclonal antibody composition displays a single binding specificity and affinity for MAC or for a particular epitope of MAC. The antibody is an IgM, IgE, IgG such as IgG1 or IgG4.

Also useful for MAC assay is an antibody that is a recombinant antibody. The term "recombinant human antibody", as used herein, includes all antibodies that are prepared, expressed, created or isolated by recombinant means, such as antibodies isolated from an animal (e.g., a mouse). Mammalian host cells for expressing the recombinant antibodies used in the methods herein include Chinese Hamster Ovary (CHO cells) including dhfr-CHO cells, described Urlaub and Chasin, Proc. Natl. Acad. Sci. USA 77:4216-4220, 1980 used with a DH FR selectable marker, e.g., as described in R. J. Kaufman and P. A. Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. To produce antibodies, expression vectors encoding antibody genes are introduced into mammalian host cells, and the host cells are cultured for a period of time sufficient to allow for expression of the antibody in the host cells or secretion of the antibody into the culture medium in which the host cells are grown. Antibodies can be recovered from the culture medium using standard protein purification methods.

Standard assays to evaluate the binding ability of the antibodies toward the target of various species are known in the art, including for example, ELISAs, western blots and RIAs. The binding kinetics (e.g., binding affinity) of the antibodies also can be assessed by standard assays known in the art, such as by Biacore analysis.

General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such as the intact protein or a portion thereof containing an epitope from human MAC, effective to produce an immune response. An exemplary protocol is as follows. The animal is subcutaneously injected in the back with 100 micrograms to 100 milligrams of antigen, dependent on the size of the animal, followed three weeks later with an intraperitoneal injection of 100 micrograms to 100 milligrams of immunogen with adjuvant dependent on the size of the animal, for example Freund's complete adjuvant. Additional intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing human MAC.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies. Any antibody of fragment thereof having affinity and specific for human MAC is within the scope of the assay for MAC deposition provided herein.

The invention herein provides in one embodiment a method of assaying extent of macular degeneration (MD) arising from a complement component in a serum in a model cell system, the method including: exposing a first sample of cells to a sample of the serum and measuring resulting lysis, and comparing extent of lysis to that in a second sample of control cells not so exposed to the serum and otherwise identical, such that the extent of lysis in the first sample compared to that in the second sample is a measure of complement-induced MD.

In other embodiments, the invention provides methods of assaying a potential therapeutic agent for efficacy in treatment of human macular degeneration (MD) in a model cell system, the method including: contacting a first sample of cells to serum and measuring resulting lysis, and contacting a second sample of otherwise identical control cells with serum and a source of human CD59 protein and measuring resulting lysis; and contacting at least a third sample of cells to a candidate therapeutic composition and otherwise identically to serum and measuring lysis, such that the extent of lysis of the third sample compared to that in the first sample and the second sample is a measure of protection by the candidate composition, thereby assaying for a potential therapeutic agent for efficacy in treatment of human MD. The source of CD59 includes pure isolated CD59 without limitation, such as purified from a natural source or made recombinantly and purified, or delivered by a vector such as a viral vector or a nucleic acid vector, the vector encoding the CD59 and capable of expressing CD59 in vivo. In examples herein, contacting with CD59 is achieved by pretreating cells or tissues with a vector encoding the CD59 gene.

In an embodiment of these methods, cell lysis is measured by propidium iodide (PI) uptake. PI is commercially available from, for example, Fluka BioChemica (Buchs, Switzerland). PI is an intercalating agent that fluoresces when bound to DNA. PI is membrane impermeant and generally excluded from viable cells, thus PI is commonly used to identify and/or determine the amount of non-living cells in a mixed population.

In other embodiments, the invention provides methods in a model cell system of assaying a serum complement component for prognosis or diagnosis of macular degeneration (MD), the method including: contacting detectably labeled cells with serum from a subject and measuring amount of extracellular and/or intracellular detectable agent for contacted cells; and comparing extracellular and/or intracellular agent in the cells to that in detectably labeled control cells not exposed to the serum and otherwise identical, such that amount of extracellular and/or intracellular agent in the contacted cells is compared to that in the control cells, such that a greater amount of extracellular detectably labeled agent in cells contacted with serum is an indication of prognosis or diagnosis of MD.

In other embodiments, the invention provides methods of assaying a potential therapeutic agent for efficacy in treatment of human macular degeneration (MD) in a model cell system, the method including: contacting a first sample of detectably labeled cells with serum from a subject and measuring amount of extracellular and/or intracellular detectable agent, and contacting a second sample of otherwise identical detectably labeled control cells with serum and a source of human CD59 protein and measuring amount of extracellular and/or intracellular detectable agent; and contacting at least a third sample of detectably labeled cells to at least one candidate therapeutic composition and otherwise identically to serum and measuring amount of extracellular and/or intracellular detectable agent, such that the amount of extracellular and/or intracellular detectable agent of the third sample compared to that in the first sample and the second sample is a measure of protection by the candidate composition, such that a greater amount of extracellular detectably labeled agent is an indication of MD, thereby assaying for a potential therapeutic agent for efficacy in treatment of human MD.

In embodiments of these methods, the detectable agent is, for example, a recombinant vector having a gene capable of expressing a detectable protein, a fluorescent agent, a colorimetric agent, an enzymatic agent, and a radioactive agent.

In certain embodiments, the detectable protein is a fluorescent protein, for example, green fluorescent protein, aequorin, cyan fluorescent protein, DsRed fluorescent protein, enhanced green fluorescent protein, and yellow fluorescent protein. Green fluorescent protein (GFP) and aequorin are bioluminescent compositions isolated from the jellyfish *Aequorea victoria*. When a calcium ion binds to aequorin, the complex breaks down into apoaequorin and a luminescent composition, which emits blue light. Synthetic aequorin is commercially available from Sealite, Sciences (Bogart, Ga.) as AQUALITE®. GFP emits light in the lower green portion of the visible spectrum, and synthetic GFP is commercially available from Clontech (Mountain View, Calif.).

Mutations to the amino acid sequence of GFP have been made to produce derivative amino acid sequences of GFP that fluoresce different colors, for example, cyan fluorescent protein, DsRed fluorescent protein, enhanced green fluorescent protein, and yellow fluorescent protein. Synthetic cyan fluorescent protein, synthetic DsRed fluorescent protein, synthetic enhanced green fluorescent protein, and synthetic yellow fluorescent protein are each commercially available from Clontech (Mountain View, Calif.).

In alternative embodiments, the detectable agent is a fluorescent agent that is not a fluorescent protein, for example, Indocyanine Green, Doxorubicin, Riboflavin, Chlorophyll, and Porphyrin.

Indocyanine Green (ICG) is a tricarbocyanine dye that upon excitation, emits lights at about 800 nm, about 820 nm, about 840 nm or at about 860 nm. ICG is commercially available from H.W.Sands Corp. (Jupiter, Fla.). Doxorubicin is fluorescent and emits light at wavelengths of, for example, about 550 nm, 600 nm, or 650 nm. Doxorubicin is commercially available from Sigma-Aldrich (St. Louis, Mo.). Riboflavin is commercially available from Sigma-Aldrich (St. Louis, Mo.) and is fluorescent, emitting light at a wavelength of, for example, about 450 nm, about 550 nm, about 650 nm, or about 750 nm. Chlorophyll A is a green photosynthetic pigment that emits light at a wavelength of, for example, about 600 nm, about 700 nm, or about 800 nm. Chlorophyll A is commercially available from suppliers such as Sigma Chemical (St. Louis, Mo.) and Turner Designs (Sunnyvale, Calif.). Porphyrin is a heterocyclic macrocycle made from 4 pyrrole subunits linked on opposite sides through 4 methine bridges (=CH—). The extensive conjugated structure of Porphyin makes the compound chromatic, i.e., fluorescent at a wavelength of, for example, about 600 nm, or about 650 nm, or about 700 nm. Porphyrin is commercially available from Sigma-Aldrich (St. Louis, Mo.).

In other alternative embodiments, the detectable agent is an enzymatic agent which is a protein, for example, β-galactosidase or alkaline phosphatase, that can be expressed on a nucleotide vector.

β-galactosidase is a hydrolase enzyme that catalyzes the hydrolysis of β-galactosides into monosaccharides. A luminescent β-galactosidase detection kit is commercially available from Clontech (Mountain View, Calif.). Alkaline phosphatase is a hydrolase enzyme responsible for removing phosphate groups from many types of molecules, including nucleotides, proteins, and alkaloids. A luminescent alkaline phosphatase detection kit is commercially available from Sigma Aldrich (St. Louis, Mo.).

Pharmaceutical Compositions

An aspect of the present invention provides pharmaceutical compositions that include a CD59 protein or a source of CD59 protein expression. In certain embodiments, these compositions optionally further include one or more additional therapeutic agents. In certain embodiments, the additional therapeutic agent or agents are selected from the group consisting of growth factors, anti-inflammatory agents, vasopressor agents including but not limited to nitric oxide and calcium channel blockers, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid.

In other embodiments, the additional agent is a compound, composition, biological or the like that potentiates, stabilizes or synergizes or even substitutes for the ability of CD59 protein to protect cells from MAC deposition. Also included are therapeutic agents that may beneficially or conveniently be provided at the same time as the CD59 protein, such as agents used to treat the same, a concurrent or a related symptom, condition or disease. In some embodiments, the drug may include without limitation anti-tumor, antiviral, antibacterial, anti-mycobacterial, anti-fungal, anti-proliferative or anti-apoptotic agents. Drugs that are included in the compositions of the invention are well known in the art. See for example, Goodman & Gilman's The Pharmacological Basis of Therapeutics, 9th Ed., Hardman, et al., eds., McGraw-Hill, 1996, the contents of which are herein incorporated by reference herein.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 provides various carriers used in formulating pharmaceutical compositions and known techniques for the preparation thereof. Some examples of materials which can serve as pharmaceutically acceptable carriers include, but are not limited to, sugars such as glucose and sucrose; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, according to the judgment of the formulator.

Therapeutically Effective Dose

Treatment of AMD by methods provided herein involves contacting retinal pigment cells with a pharmaceutical composition, for example, administering a therapeutically effective amount of a pharmaceutical composition having as an active agents a CD59 protein or a source of expression of a CD59 protein, to a subject in need thereof, in such amounts and for such time as is necessary to achieve the desired result.

The compositions, according to the method of the present invention, may be administered using any amount and any route of administration effective for treating AMD. Thus, the expression "amount effective for treating AMD", as used herein, refers to a sufficient amount of composition to beneficially prevent or ameliorate the symptoms of AMD.

The exact dosage is chosen by the individual physician in view of the patient to be treated. Dosage and administration are adjusted to provide sufficient levels of the active agent(s)

or to maintain the desired effect. Additional factors which may be taken into account include the severity of the disease state, e.g., intermediate or advanced stage of AMD; age, weight and gender of the patient; diet, time and frequency of administration; route of administration; drug combinations; reaction sensitivities; and tolerance/response to therapy. Long acting pharmaceutical compositions might be administered hourly, twice hourly, every 3 to four hours, daily, twice daily, every 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, as provided herein, usually mice, but also potentially from rats, rabbits, dogs, or pigs. The animal cell model provided herein is also used to achieve a desirable concentration and total dosing range and route of administration. Such information can then be used to determine useful doses and routes for administration in humans.

A therapeutically effective dose refers to that amount of active agent that ameliorates the symptoms or condition or prevents progression of AMD. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use.

The daily dosage of the products may be varied over a wide range, such as from 0.001 to 100 mg per adult human per day. For ocular administration, the compositions are preferably provided in the form of a solution containing 0.001, 0.01, 0.05, 0.1, 0.5, 1.0, 2.5, 5.0, 10.0, 15.0, 25.0, 50.0, 100.0, 250.0, or 500.0 micrograms of the active ingredient for the symptomatic adjustment of the dosage to the patient to be treated.

A unit dose typically contains from about 0.001 micrograms to about 500 micrograms of the active ingredient, preferably from about 0.1 micrograms to about 100 micrograms of active ingredient, more preferably from about 1.0 micrograms to about 10 micrograms of active ingredient. An effective amount of the drug is ordinarily supplied at a dosage level of from about 0.0001 mg/kg to about 25 mg/kg of body weight per day. For example, the range is from about 0.001 to 10 mg/kg of body weight per day, or from about 0.001 mg/kg to 1 mg/kg of body weight per day. The compositions may be administered on a regimen of, for example, one to four or more times per day.

Administration of a source of expression of a CD59 protein is administration of a dose of a viral vector or a nucleic acid vector, such that the dose contains at least about 50, 100, 500, 1000, or at least about 5000 particles per cell to be treated. Cell number can be calculated from retinal area in need of treatment by methods known to one of skill in the art of AMD.

Administration of Pharmaceutical Compositions

As formulated with an appropriate pharmaceutically acceptable carrier in a desired dosage, the pharmaceutical composition provided herein is administered to humans and other mammals topically such as ocularly (as by solutions, ointments, or drops), nasally, bucally, orally, rectally, parenterally, intracisternally, intravaginally, or intraperitoneally.

Ocular injections include intra-ocular injection into the aqueous or the vitreous humor, or injection into the external layers of the eye, such as via subconjunctival injection or subtenon injection.

Liquid dosage forms for ocular, oral, or other systemic administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be therapeutic or it may be prophylactic. The invention includes opthalmological devices, surgical devices, audiological devices or products which contain disclosed compositions (e.g., gauze bandages or strips), and methods of making or using such devices or products. These devices may be coated with, impregnated with, bonded to or otherwise treated with a composition as described herein.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

The invention having now been fully described, it is further illustrated by the following examples and claims, which are illustrative and are not meant to be further limiting.

A portion of this work was published in a paper entitled, "Evaluation of Adenovirus-Delivered Human CD59 as a Potential Therapy for AMD in a Model of Human Membrane Attack Complex Formation on Murine RPE", co-authored by the inventors Kasmir Ramo, Siobhan Cashman, and Rajendra Kumar-Singh, (Invest Opthalmol V is Sci. September 2008; vol. 49, pp. 4126-4136), and this paper is hereby incorporated by reference herein in its entirety.

The invention now having been fully described, it is further exemplified by the following examples and claims. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference.

EXAMPLES

Compositions that include CD59 protein or a source of in vivo expression of CD59 protein are shown by the following Examples to be effective to treat AMD. A humanized murine model of measuring human MAC deposition in vitro and in vivo is shown in the following Examples, and this model is used to measure protection of murine RPE from the deleterious deposition of human MAC by a vector that expresses human CD59 protein.

Example 1

Adenovirus Vector Constructs

Human CD59 cDNA was obtained from the American Type Tissue Culture Collection (ATCC, Manassas, Va.) and PCR amplified using a forward primer containing an XhoI site, (underlined; 5' ccccctcgagtggacaatcacaatggg3'; SEQ ID NO:1) and a reverse primer with an EcoRV site (underlined; 5' cccccgatatcaacggggagtttgggagaag3'; SEQ ID NO:2).

The PCR product was gel purified and, after XhoI/EcoRV digestion, cloned into XhoI/EcoRV digested pShCAG (constructed by cloning a SalI/BamHI fragment of pCAGEN into XhoI/BglIII digested pShuttle) generating pShCAGCD59. Automated sequencing confirmed that the CD59 sequence had been introduced into the generated plasmid. This shuttle plasmid was then used to produce the adenovirus vector using protocols published in Klein et al., Opthalmology, 114:253-262, 2007 and van Leeuwen et al., Eur. J. Epidemiol., 18:845-854, 2003. pShCAGCD59 was linearized with PmeI, gel purified and recombined with pAdEasy-1 by co-transformation of *Escherichia coli* BJ5183 cells. The recombined plasmid was linearized with PacI, transfected into the human embryonic retinoblast (911) cell line and the resulting vector (AdCAGCD59) was purified using the adenovirus purification kit Adenopure (Puresyn, Inc., Malvern, Pa.).

Control vector AdEMPTY was generated similarly by recombining the PmeI linearized pSHCAG with pAdEasy-1. The AdCAGGFP control vector is described in Johnson et al., Exp. Eye Res., 70:441-449, 2000.

Example 2

Cell Lines and Pretreating with CD59 by Adenovirus Contacting

Human embryonic retinoblast cell line 911 was maintained in Dulbecco's Modified Eagle's Medium (DMEM) supplemented with 10% fetal bovine serum (FBS) and mouse hepatoma cell line hepa-1c1c7 (ATCC, Manassas, Va.) in α-MEM supplemented with 10% FBS. Cells were cultured in a humidified incubator at 37° C. under 5% $CO_2$:95% air atmosphere.

For Western blot analysis or the human serum cell lysis assay $1.2 \times 10^6$ hepa-1c1c7 cells and for CD59 immunocytochemistry or the human serum MAC deposition assay $2.5 \times 10^4$ hepa-1c1c7 cells were contacted with either AdCAGGFP or AdCAGCD59 vectors at multiplicities of infection of the virus particles per cell as indicated, or control cells were not so contacted. Adenovirus contacting to cells was performed in media with 2% FBS. Three days after contacting, cells were further treated as described in Examples herein. While specific conditions are described herein, equivalent conditions of media, temperature, etc., to achieve effective pretreatment of cells or tissues with CD59 are within the scope of the methods herein.

Primary Mouse RPE cells were harvested from eyes of sacrificed 6-10 week old C57Bl/6J mice. After removing each of the anterior chamber, lens and retina as described below, eyecup tissues were incubated in 200 μl 0.25% trypsin-EDTA in 1.5 ml eppendorf tubes for 40 to 50 minutes at 37° C. Eyecup tissues were subsequently transferred to a 60 mm cell culture plate containing α-MEM supplemented with 10% FBS. The RPE cells were gently scraped with a pipet tip, the RPE sheets were aspirated using a 200 μl pipet and transferred to an eppendorf tube. After dispersing the RPE sheets by pipeting the media several times, cells were counted and about $3 \times 10^4$ cells (generally the yield obtained from one eye) were seeded in one chamber of a poly-D-lysine-coated chamberslide (Becton Dickinson, Franklin Lakes, N.J.). After one week in culture, cells were used as described in Examples herein. Contacting cells with adenovirus vector was performed in media with 2% FBS.

Example 3

Western Blot Analysis

Cells were lysed in 50 mM Tris-HCl, pH 8.0/150 mM NaCl/0.1% sodium dodecyl sulfate/1% Triton X-100 containing 2% (v:v) protease inhibitor cocktail (Sigma-Aldrich, St. Louis, Mo.). Media from cells were collected, centrifuged, passed through a 0.22 μm filter or other filter as indicated in the figures, to remove remaining cell debris and media were concentrated 10× using a Biomax centrifugal filter with a 10,000 Dalton pore size (Millipore Corporation, Billerica, Mass.). Lysates were analyzed by gel electrophoresis under non-reducing conditions on a 15% Tris-glycine SDS-PAGE gel (Bio-Rad Laboratories, Hercules, Calif.) and proteins were transferred to a polyvinylidene fluoride (PVDF) membrane (Millipore, Billerica, Mass.). Following blocking in 5% (w:v) skim milk (Becton Dickinson, Sparks, Md.), the membrane was probed for human CD59 using a mouse anti-human CD59 monoclonal antibody (1:1000 dilution; Clone Mem-43; Abcam, Cambridge, Mass.), followed by a secondary antibody horseradish peroxidase-conjugated goat anti-mouse antibody (1:10 000 dilution; Jackson Immunoresearch, West Grove, Pa.). Following stripping and blocking as described above, the same membrane was probed for β-Actin with a mouse anti-β-actin monoclonal antibody (1:5 000 dilution; Clone AC-15; Sigma-Aldrich, St. Louis, Mo.). Secondary detection was performed as described above.

Example 4

Human Serum Cell Lysis Assay

Normal human serum (NHS) was purchased in lyophilized form from Sigma (St. Louis, Mo.) and reconstituted (per manufacturer instructions) with 1 ml of cold sterile deionized water to obtain a volume of serum equal to that of the human plasma from which the powder was obtained. The resulting human serum lots having a hemolytic titer of 43 $CH_{50}$ units/ml or 74 $CH_{50}$ units/ml respectively (determined by the manufacturer using the method of Kabat and Mayer) were aliquoted and stored at −80° C. The first lot with a hemolytic titer K) of 43 $CH_{50}$ units/ml was used in experiments with hepa-1c1c7 cells. The second lot, with a hemolytic titer of 74 $CH_{50}$ units/ml, was used in the other experiments.

For the human serum cell lysis assay, single cell suspensions of pretreated cells, i.e., including control cells not contacted with vector, or adenovirus contacted hepa-1c1c7 cells in a total volume of 500 μl were used. Following removal of media, cells were washed twice with 1× phosphate buffered saline (PBS) and after brief trypsinization (0.25% trypsin-EDTA, 4-6 mins), harvested with 1×PBS containing 0.5% FBS. Cells were collected by centrifugation at 4° C. and resuspended in ice-cold gelatin veronal buffer with $Ca^{2+}$ and $Mg^{2+}$ ($GVB^{++}$, Complement Technology, Tyler, Tex.). Cells were counted on a hemacytometer and $5 \times 10^5$ cells were aliquoted into eppendorf tubes. Normal human serum (NHS) or heat inactivated (56° C. for 1 hour) normal human serum (HI-NHS) was added to cells, and the cell suspensions were incubated at 37° C. for 1 hour with gentle rotatory shaking. Cell lysis was determined by the propidium iodide (PI) exclusion method followed by FACS analysis.

Shortly prior to FACS, one microliter of PI (1 mg/ml; Fluka BioChemica, Buchs, Switzerland) was added to a cell suspension and 25,000 events per sample were counted on a FACSCalibur (Becton Dickinson, Franklin Lakes, N.J.). Results were analyzed using the CellQuest Pro software (Becton Dickinson, Franklin Lakes, N.J.) and percent cell lysis was calculated using the formula shown below.

% Cell Lysis=[1−(% live cells in HI-NHS/% live cells in NHS)]×100

Example 5

MAC Deposition Assay in Cell Culture

Mouse hepa-1c1c7 cells were cultured for three days, and were pretreated by contacting with AdCAGGFP (negative control), or AdCAGCD59, in poly-D-lysine-coated chamberslides (Becton Dickinson, Franklin Lakes, N.J.) and were washed twice with 1×PBS. Cells were then incubated with 10% (v:v) NHS or HI-NHS in $GVB^{++}$ (Complement Technology, Tyler, Tex.) at 37° C. for 1, 3, 5, 7 or 10 minutes.

Primary mouse RPE cells were incubated with or without 25 μg/ml goat anti-mouse emmprin antibody (R&D Systems, Minneapolis, Minn.) in $GVB^{++}$ (Complement Technology, Tyler, Tex.) for 1 hour and either washed and fixed (for emmprin immunocytochemistry) or were treated for the MAC deposition assay followed by addition of NHS or HI-NHS (final concentration 50%) for 4 or 7 minutes. Thereafter cells were washed three times with ice cold 1×PBS and fixed with 3.7% formaldehyde (MP Biomedicals, Solon, Ohio) in 1×PBS for 15 minutes. Cells were washed another three times with 1×PBS to remove remaining fixative and stored in 1×PBS at 4° C. until immunocytochemical analysis, as described in Examples herein.

Example 6

Immunocytochemistry/Immunohistochemistry

Fixed cells or tissues described above were incubated with primary mouse monoclonal antibodies to human CD59

(clone M-43) or human C5b-9 (clone aE11) (each at 1:50 dilution, Abcam, Cambridge, Mass.) in 1×PBS containing 6% (w:v) normal goat serum (Jackson Immunoresearch, West Grove, Pa.) for 2.5 hours with gentle rotatory shaking. Secondary detection was performed using a Cy3 conjugated goat anti-mouse antibody (1:400 dilution; Jackson Immunoresearch, West Grove, Pa.) for 1.5 hours in a dark chamber.

For RPE65 immunostaining, primary RPE cells were pre-blocked and permeabilized in 1×PBS containing 6% (w:v) normal goat serum (Jackson Immunoresearch, West Grove, Pa.) and 0.25% (v:v) Triton X-100 (Fisher Bio-reagents, Fair Lawn, N.J.) for 1 hour. A mouse anti-RPE65 antibody was then applied and primary and secondary detection were performed as above except that the antibody and washing solutions contained 0.25% (v:v) Triton X-100 (Fisher Bio-reagents, Fair Lawn, N.J.).

For mouse emmprin staining, goat anti-mouse emmprin antibody treated and fixed cells and tissues were blocked in 1×PBS containing 6% (w:v) normal donkey serum (Jackson Immunoresearch, West Grove, Pa.) for 1 hour and secondary detection was performed using a Cy3-conjugated donkey anti-goat antibody (1:400 dilution; Jackson Immunoresearch, West Grove, Pa.) in 1×PBS containing 6% (w:v) normal donkey serum for 1.5 hours.

Example 7

Trypan Blue Exclusion Assay

Cells were treated as for the MAC deposition assay in cell culture as described in Examples above, except that after washing to remove the serum, cells were incubated in 0.1% trypan blue solution for 5 minutes. Cells were subsequently washed twice with 1×PBS and fixed as described in Examples above.

Example 8

Subretinal Injections

Mice (C57B1/6J) were purchased from Jackson Laboratories (Bar Harbor, Me.), bred and maintained in a 12-hour light-dark cycle. Mice were anesthetized by intraperitoneal injection of xylazine (10 mg/ml)/ketamine (1 mg/ml). Subretinal injections were performed as described in Anderson Am J. Opthalmol., 134:411-431, 2002, using the transcleral-transchoroidal approach with a 32-gauge needle attached to a 5 µl glass syringe (Hamilton, Reno, Nev.). One microliter of a control mixture of nine parts AdEMPTY and one part AdCAGGFP (total of $3 \times 10^8$ vector particles; control) or of a mixture of nine parts AdCAGCD59 and one part AdCAGGFP (total of $3 \times 10^8$ vector particles) was injected into each subject mouse.

Example 9

MAC Deposition on RPE and Cornea

Six days after administering to pretreat by injection, mice were sacrificed by $CO_2$ inhalation and eyes were harvested and placed in 1×PBS containing penicillin (100 U/ml) and streptomycin (100 U/ml). A circular incision was made 1-2 mm posterior to the ora serata and the entire anterior chamber including the lens was carefully removed. After making a small incision at the base of the optic nerve to cut the ganglionic axons, the retina was removed and the eyecup tissue was either fixed immediately in 4% paraformaldehyde in phosphate buffer (pH 7.4) overnight (for CD59 immunohistochemistry) or incubated with 25 µg/ml goat anti-mouse emmprin antibody (R&D Systems, Minneapolis, Minn.) in cold GVB++ (Complement Technology, Tyler, Tex.) at 4° C. for 1 hour.

Eyecup tissues were then either washed three times with cold PBS and were fixed for emmprin immunohistochemistry. For MAC deposition assay, an equal volume of NHS or HI-NHS (final concentration 50%) was added to the eyecup tissues which were then incubated at 37° C. for 15 minutes and were washed three times with cold PBS and were fixed.

Cornea tissues were harvested from uninjected mice, the iris was removed and the corneas cultured in 300 µl of DMEM with 2% FBS. Corneas were contacted with $1.5 \times 10^9$ vector particles of AdCAGGFP (negative control) or the AdCAGCD59 vector. Three days post-harvesting/contacting, each of untreated corneas (negative control), AdCAGGFP pretreated corneas (negative control) and AdCAGCD59 pretreated corneas was mixed with anti-mouse emmprin antibody as with eyecup tissues, and each was either washed and fixed (for emmprin immunohistochemistry), or was contacted with 50% NHS or HI-NHS for 20 minutes and then washed and fixed (for the MAC deposition assay). Prior to immunohistochemistry, tissues were washed three times for ten minutes each with 1×PBS to remove remaining fixative.

Example 10

Figure 1A:
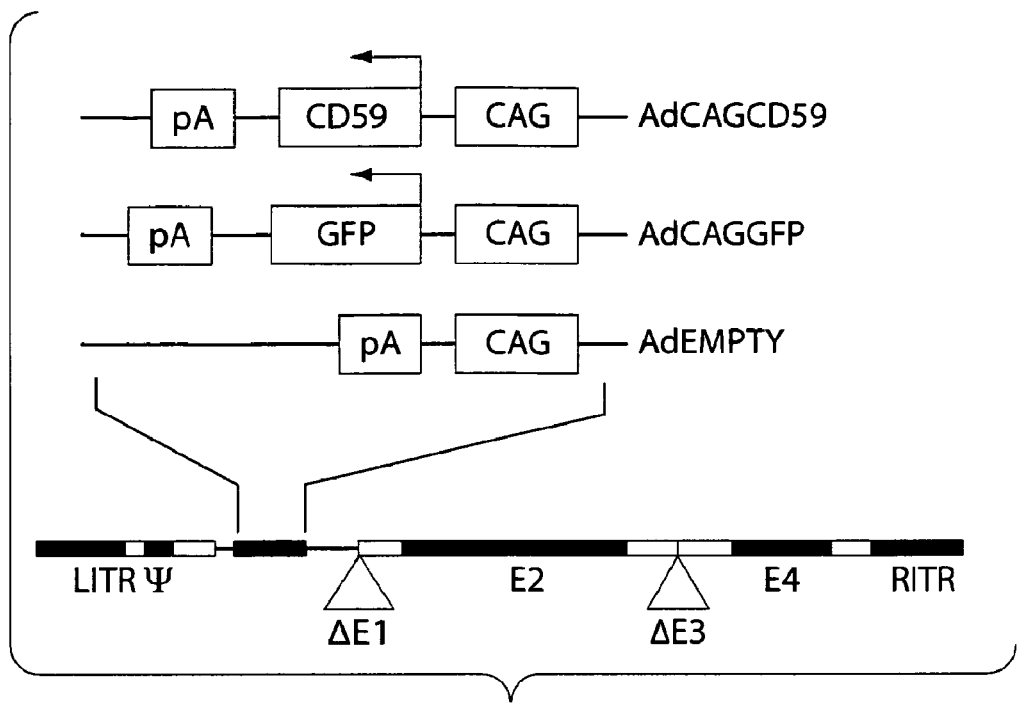
FIG. 1 panel A is a drawing showing constructs AdCAGCD59 serotype 5 adenovirus vector containing a gene encoding human CD59 under control of the chicken beta actin (CAG) promoter, and of two control adenovirus vectors, AdCAGGFP expressing GFP also regulated by the CAG promoter, and negative control vector AdEMPTY. Symbols used: pA, polyadenylation signal; CAG, cytomegalovirus chicken β-actin β-globin promoter; Ψ, Ad packaging signal; ITR, adenovirus inverted terminal repeat; Δ, deleted; E, early region labels.
Figure 1B:
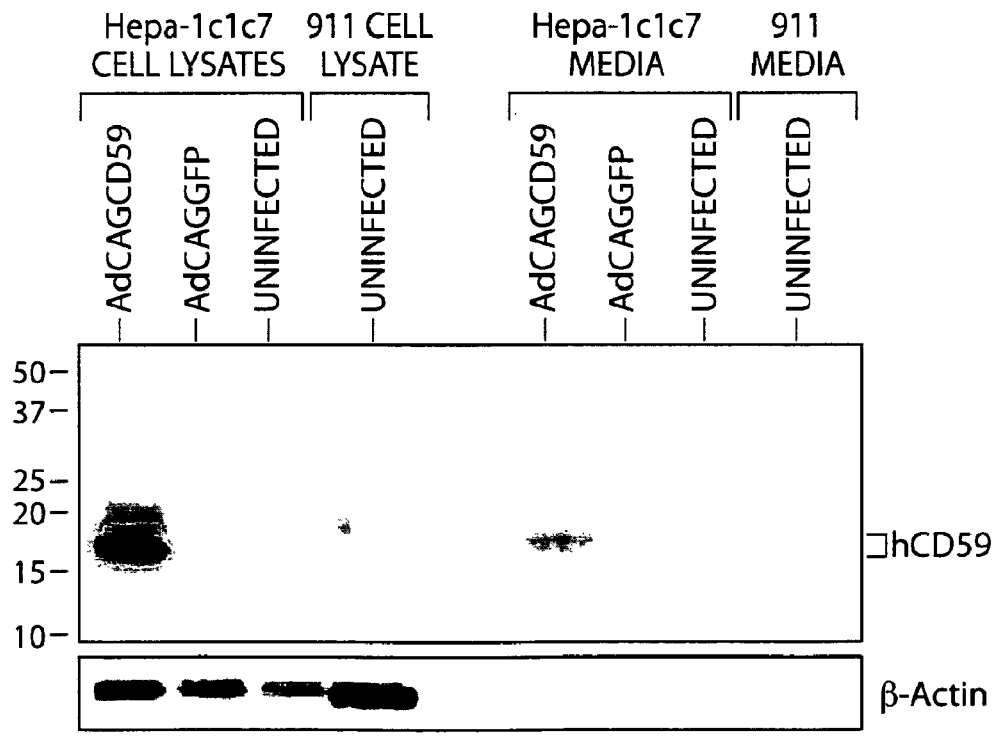
Figure 2A:
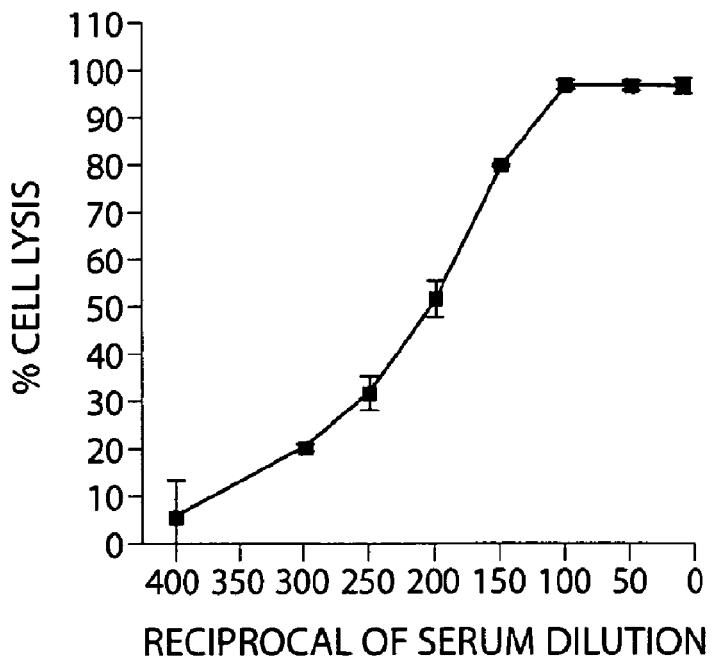
FIG. 2 is a set of graphs showing functional activity of human CD59 expressed in cells contacted with AdCAGCD59 vector.
Figure 2B:
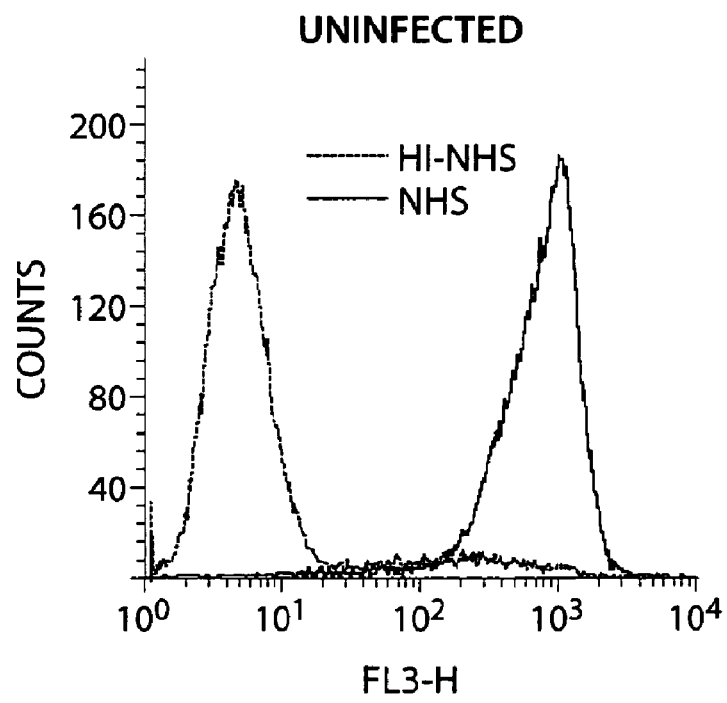
Figure 2C:
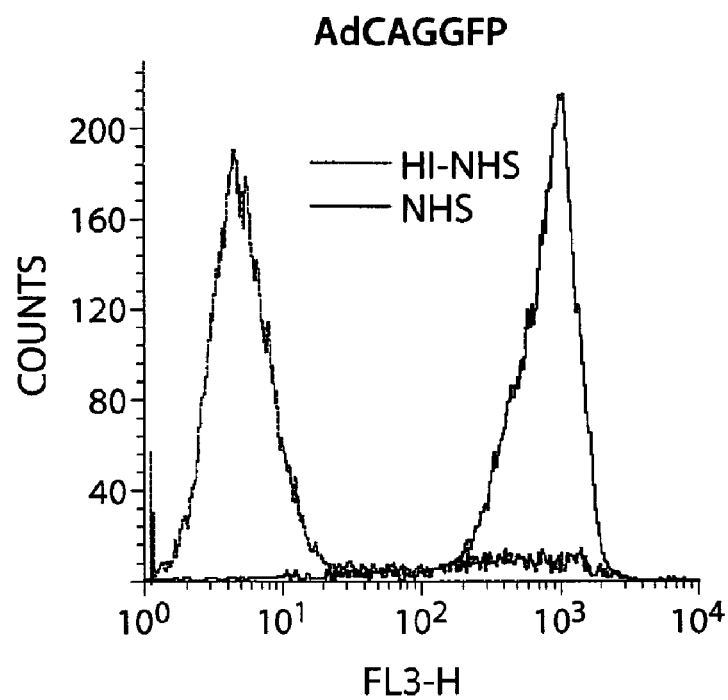
Figure 2D:
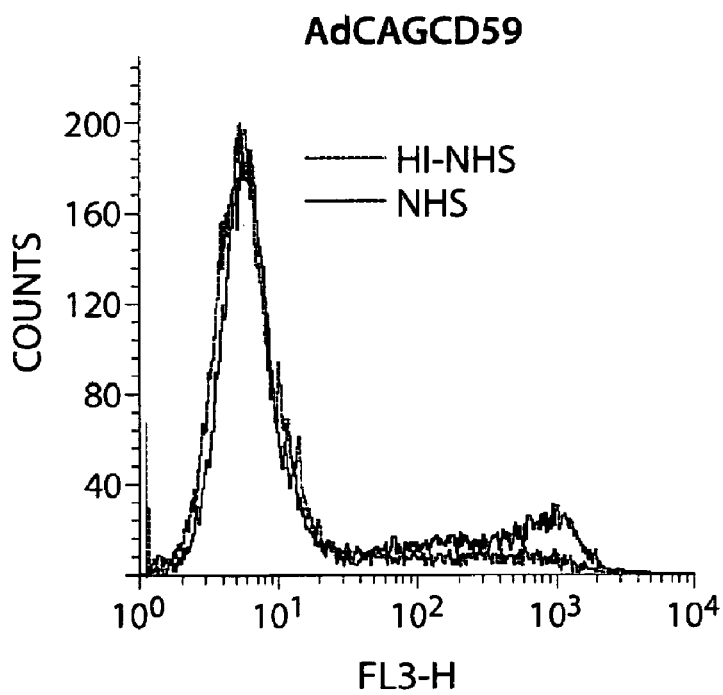
Figure 2E:
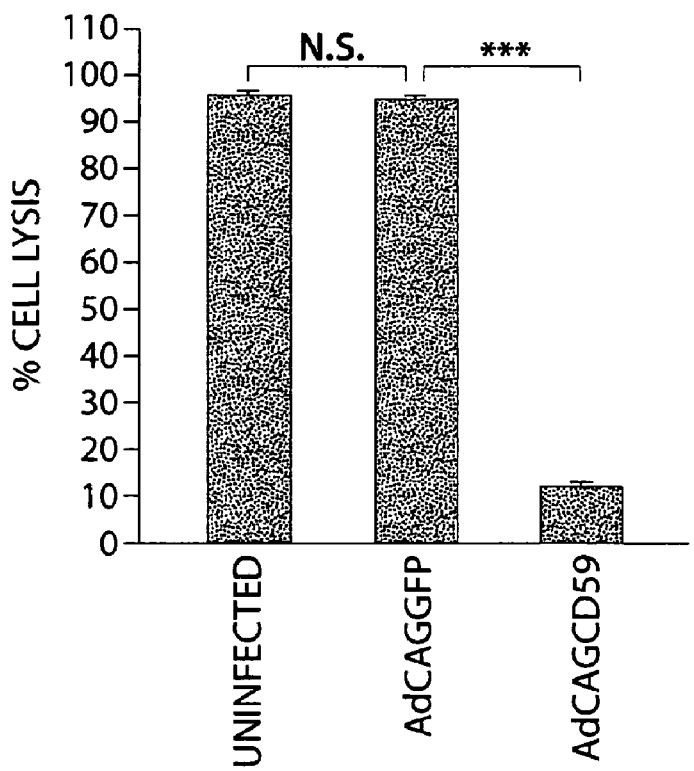
Figure 2F:
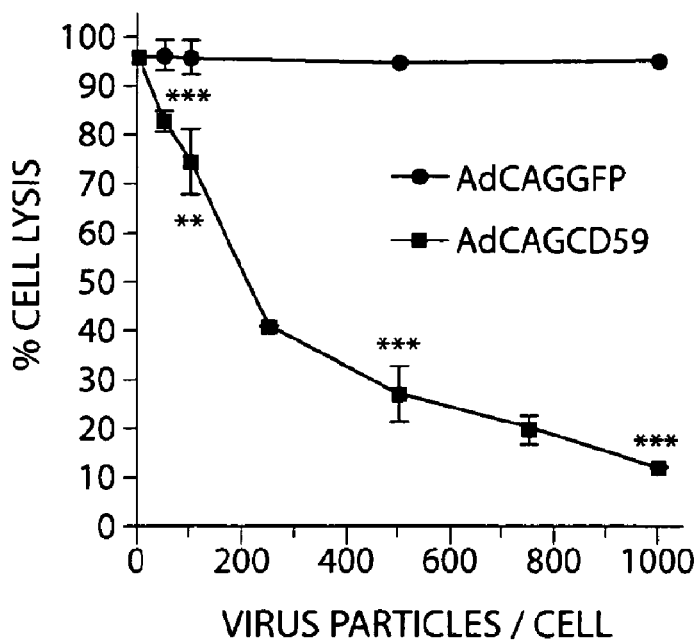

Vector Constructs and Human CD59 Expression in Vector-Pretreated Hepa-1c1c7 Cells To deliver human CD59 (hCD59) in order to pretreat murine RPE and retina in vivo, a first generation serotype 5 adenovirus containing hCD59 cDNA under control of chicken beta actin (CAG) promoter (AdCAGCD59 vector; FIG. 1 panel A) was produced. Two negative adenovirus control vectors were also constructed, AdCAGGFP expressing GFP under control of the CAG promoter, and AdEMPTY (FIG. 1 panel A). These vectors were constructed to have a deletion in region E1 of adenovirus, and are therefore replication deficient outside of the packaging cells.

Human CD59 is an 18-21 kDa glycosylphosphatidylinositol (GPI)-anchored membrane protein. To analyze expression of the protein, mouse hepa-1c1c7 cells were contacted for pretreatment with a multiplicity of 1000 vector particles (vp/cell) of the purified AdCAGCD59 or control vector. Cell lysates were analyzed by Western blotting using a monoclonal antibody to hCD59, and the presence of hCD59 was observed in cell lysates of AdCAGCD59 pretreated cells (FIG. 1 panel B). No CD59 protein was detected in lysates of cells contacted with the control vector (AdCAGGFP, negative control) or control cells not pretreated with vector (negative control; FIG. 1 panel B).

Endogenous hCD59 was detected in human embryonic retinoblast (911) cell lysates (FIG. 1 panel B), however this signal was much weaker compared to the signal from the AdCAGCD59 contacted mouse cells. The slight shift in electrophoretic mobility between the endogenous hCD59 detected in 911 cell lysates and the recombinant hCD59 detected in AdCAGCD59 contacted mouse cell lysates may be due to differences in protein modification; for example, variation in protein glycosylation pattern in the two cell lines.

Immunostaining of non-permeabilized AdCAGCD59 contacted mouse hepa-1c1c7 cells using the anti-hCD59 antibody showed expression and localization of hCD59 on the cell membrane (FIG. 1 panel C) and revealed that essentially 100% of cells were expressing the protein. Stain was not observed on cells contacted with the negative control vector. Additional controls included immunocytochemistry of untreated cells and omission of the primary antibody during immunocytochemistry of AdCAGCD59 contacted cells, and results obtained using these controls were negative.

Example 11

Adenovirus Pretreatment with hCD59 by Vector Contact Protects Mouse Cells from Human Complement Mediated Cell Lysis To test the functional activity of hCD59 expressed from the AdCAGCD59 vector, human serum cell lysis assays were performed on mouse hepa-1c1c7 cells. Cell suspensions were incubated with NHS or HI-NHS (as a control for non-complement specific lysis) to expose the cells to complement, and percent cell lysis was determined by uptake of PI as detected and quantified by FACS analysis.

Effect of concentration of serum on the extent of lysis of control untreated cells was initially investigated (FIG. 2 panel A). Mouse hepa-1c1c7 cells effectively activated human complement, and a serum concentration as low as 0.5% (1/200 dilution) was observed to lyse greater than 50% of cells. It was observed that lysis of cells was serum concentration dependent and the function appeared to be sigmoidal (FIG. 2 panel A). The lowest serum concentration tested that resulted in maximal cell lysis was 1% (1/100 dilution; cell lysis was 96.06%±0.87%). This serum concentration was used in subsequent cell lysis Examples with cells pretreated by contacting with adenovirus vector.

Cells were pretreated with 1000 vp/cell of the AdCAGCD59 or the negative control AdCAGGFP vector and 65 hours after contacting, the cells were harvested and used in human serum cell lysis experiments. Adenovirus pretreatment at amounts used here did not result in cell toxicity as observed by microscopy or as detected by PI uptake followed by FACS, and by comparison with data obtained from cells contacted with the two vectors and from control untreated cells as shown herein. It was observed that cell lysis of contacted cells incubated in HI-NHS was minimal and was similar to that of cells not pretreated with a vector (control) incubated with HI-NHS (FIG. 2 panels B, C and D). Cells pretreated with the AdCAGCD59 vector were significantly protected, as complement mediated cell lysis was reduced (about eight-fold) to 12.29%±0.18% (cell lysis is an indication of cell killing and an inverse measure of cell survival; FIG. 2 panels B, D and E).

In contrast, mouse cells pretreated with the negative control AdCAGGFP vector were not protected, i.e., remained susceptible to human complement, with extent of complement mediated cell lysis observed at 95.27%±0.01% of cells (FIG. 2 panels C and E). Similarly, it was observed that untreated mouse cells were susceptible to human complement and cell lysis (FIG. 2 panels A, B and E). Pretreatment with control vector AdCAGGFP, by contrast, did not protect cells, as the extent of lysis observed was 95.27%±0.01% (FIG. 2 panels C and E), similar to that observed for control cells (FIG. 2 panels B and E). These data show that protection was due to expression of hCD59 rather than adenovirus pretreatment per se.

Protection of cells from lysis was obtained herein by expression of human CD59 in cells pretreated with AdCAGCD59 vector. It was further observed that protection was dependent on the multiplicity of AdCAGCD59 vector administered. Administering 250 vp/cell and 500 vp/cell of AdCAGCD59, respectively, inhibited cell lysis by over 50% and 70%, respectively (FIG. 2 panel F). In contrast, AdCAG-GFP pretreated cells were susceptible to lysis regardless of multiplicity of vector administered. Thus, expression of recombinant hCD59 from the AdCAGCD59 vector significantly protected the mouse cells from human complement mediated cell lysis.

Example 12 hCD59 Protein Protects Mouse Cells from Human MAC Deposition

Data in Examples above show that incubation of mouse hepa-1c1c7 cells with normal human serum led to complement activation and extensive cell lysis, and that this lysis was efficiently inhibited when recombinant human CD59 was expressed in these cells.

Examples were performed to determine whether recombinant human CD59 expressed by adenovirus pretreated mouse cells would prevent formation of the C5b-9 complex in an in vitro MAC deposition assay developed for this purpose.

Figure 3A:
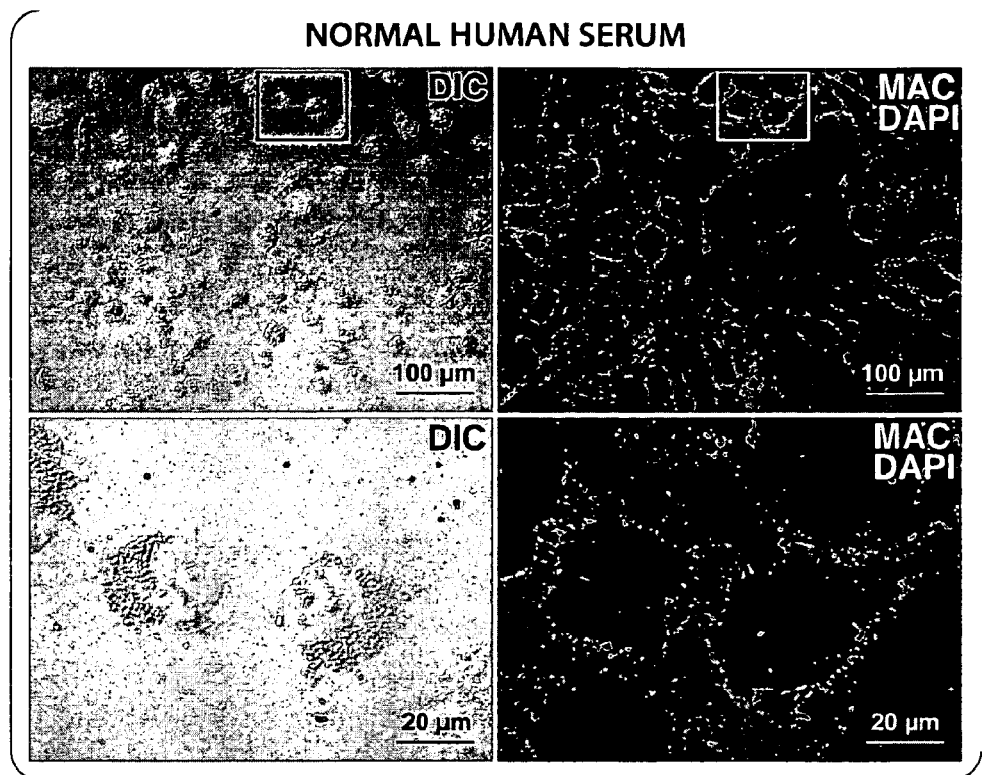
FIG. 3 panels A and B are each a set of four photomicrographs showing that mouse cells are susceptible to C5b-9 deposition when exposed to NHS.
Figure 3B:
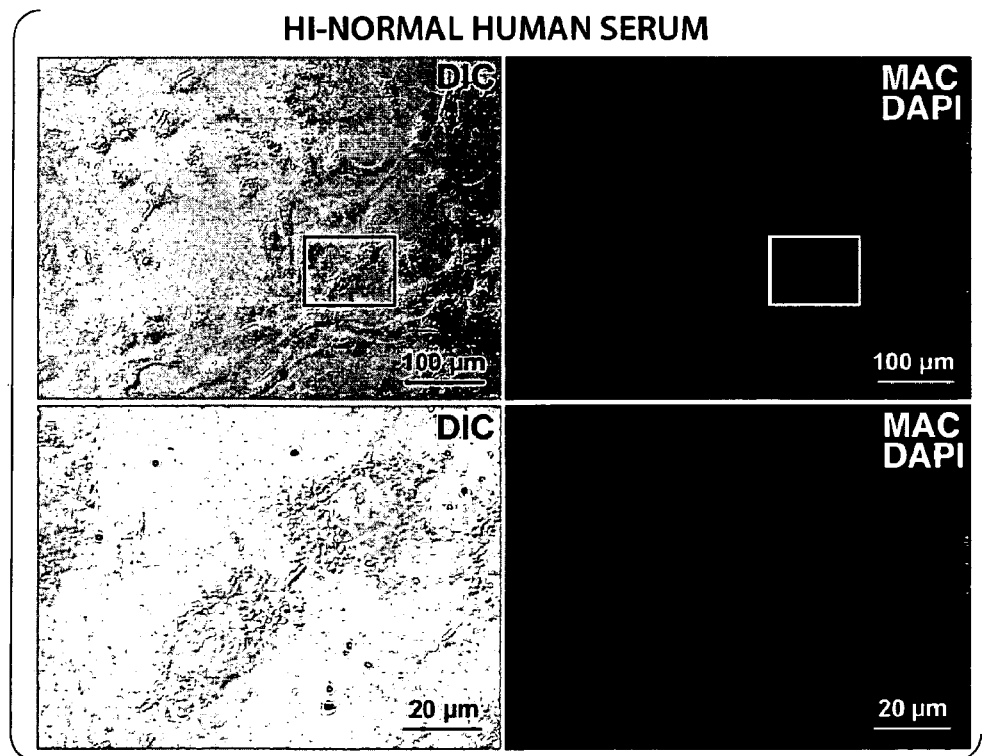
Figure 3C:
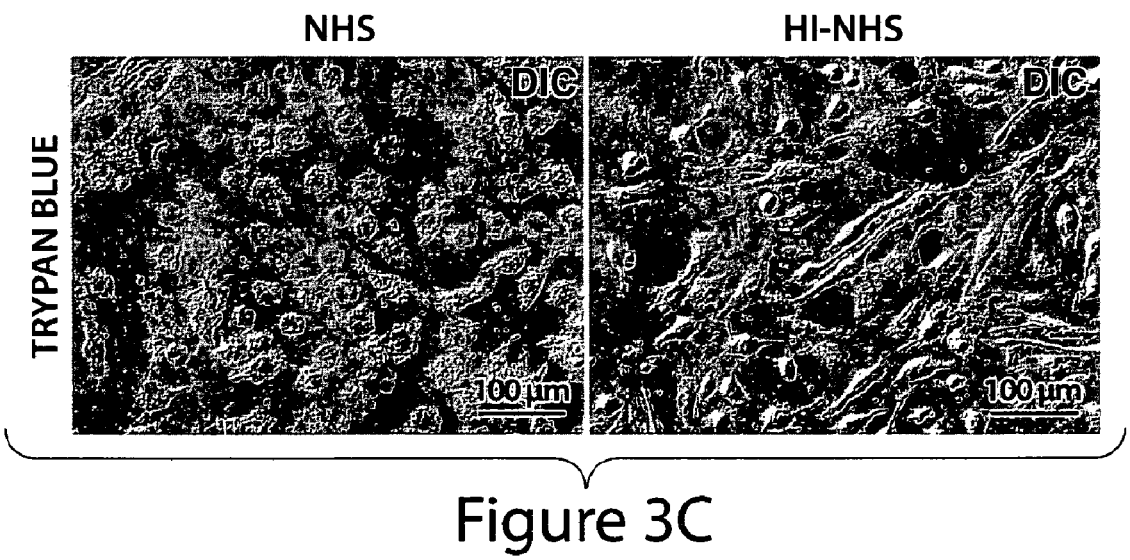

Mouse cells in poly-D-lysine coated chamberslides were incubated with 10% NHS or HI-NHS in GVB$^{++}$ at 37° C. for 1 to 10 minutes and subsequently washed and fixed. Incubation of these cells with NHS for 5 minutes caused significant changes in cell morphology (FIG. 3 panel A, DIC visualization of cells). Cells showed deleterious effects as they lost their extensive cytoplasmic processes and became round and granular. In contrast, these effects were not observed with cells incubated with HI-NHS (FIG. 3 panel B, DIC visualization of cells) in which complement is inactivated.

Immunocytochemical analysis using a monoclonal antibody directed to a neoepitope on the C5b-9 complex revealed extensive membrane staining at the borders of cells exposed to NHS confirming deposition of the MAC on these cells (FIG. 3 panel A). Almost no MAC staining was not observed on cells exposed to HI-NHS (FIG. 3 panel B). Control samples included immunocytochemistry of untreated cells (not incubated with human serum) as well as omission of the primary antibody during immunocytochemistry of NHS contacted cells, both of which controls yielded negative data. Under conditions of exposure to the complement in human serum, lysis of a substantial amount of the NHS exposed cells was shown also by trypan blue staining (FIG. 3 panel C). No lysis was observed on HI-NHS exposed cells as indicated by the absence of trypan blue uptake by these cells (FIG. 3 panel C).

Pretreating the mouse hepa-1c1c7 cells with 1000 vp/cell of the AdCAGCD59 vector was found to significantly protect these cells from human MAC deposition and eventual lysis (FIG. 4 panels B and C). Following exposure to NHS for 5 minutes, these pretreated cells maintained their normal morphological characteristics (FIG. 4 panel B, DIC). Immunocytochemistry using anti-MAC antibody showed almost complete absence of MAC staining (FIG. 4 panel B), and cell lysis was efficiently inhibited as indicated by the absence of trypan blue staining (FIG. 4 panel C). In contrast, cells pretreated with the negative control vector expressing GFP were not protected from MAC deposition following 5 minutes of NHS exposure. Morphological changes (FIG. 4 panel A, DIC), MAC immunostaining (FIG. 4 panel A) and cell lysis (FIG. 4 panel C) of these cells were similar to that observed for untreated control cells (control; FIG. 3 panels A and C), i.e., characteristic of MAC deposition and cell lysis.

It was observed that MAC staining was present on even a few of the AdCAGCD59 pretreated cells following 7 minutes of NHS treatment (FIG. 4 panel B) and this number increased after 10 minutes of serum treatment. Following 7 minutes of NHS treatment, MAC staining of AdCAGGFP pretreated cells (FIG. 4 panel A) was significantly stronger than of AdCAGCD59 pre-contacted cells (FIG. 4 panel B). Following 10 minutes of serum treatment almost all AdCAGGFP pretreated cells were detached from the cell culture slide due to complete lysis, while only a few cells pretreated with AdCAGCD59 vector showed any changes or MAC deposition. Furthermore, the pattern of MAC immunofluorescence indicated the extent of cell membrane damage, with strong punctate staining delineating cell borders correlating with greater damage to cells (FIG. 3 panel A, FIG. 4 panel A and FIG. 5), and more diffuse staining extending throughout the cell membrane correlating with cells that appeared to be intact (FIG. 4 panel B and FIG. 5). MAC deposition on untreated control cells and on AdCAGGFP pretreated cells was rapid and punctate. Diffuse staining, indicating lower less damaging levels of MAC deposition, was seen primarily on AdCAGCD59 pretreated cells (FIG. 4 panel B and FIG. 5).

The different patterns of MAC immunostaining was more readily observed when cells were pre-contacted at lower multiplicities of the AdCAGCD59 vector. Following 5 minutes of NHS exposure, cells pretreated with 100 or 500 vp/cell showed more MAC immunostaining compared to cells contacted with 1000 vp/cell (FIG. 5, especially greater magnification in the lower left photomicrograph). Pretreating by contacting cells with even these lower multiplicities of the hCD59 expressing adenovirus yielded significant protection of the cells from MAC deposition (see FIG. 4 panel A for comparison).

Example 13

Model of Human MAC Deposition on Murine RPE, Primary RPE Cells and Corneal Endothelium A MAC deposition assay was developed in order to use murine ocular tissues to assay extent of AMD damage or potential for AMD, and to use to screen agents to treat or prevent AMD.

Eyecup tissues were harvested from C57B1/6J mice and exposed to various concentrations of NHS or HI-NHS. Immunohistochemical analysis with the anti-human C5b-9 antibody was followed by an appropriate Cy3 conjugated secondary antibody. The data showed no fluorescent signal on the RPE, even when eyecup tissues were contacted with a concentration of NHS as high as 50%. Contacting with 100% NHS resulted in occasional scattered weak staining (FIG. 6 panel C). The inconsistent weak signal obtained was not useful for purposes of any development. Further, attempts to use the cornea to test the potential of adenovirus delivered hCD59 to protect murine ocular tissues from human MAC deposition also were not successful. No MAC deposition, at any NHS concentration used, was detected on the corneal endothelium, which is known to be efficiently transduced by adenoviruses. Strong MAC immunostaining was always detected on the corneal epithelium.

The MAC deposition assay was performed on primary mouse RPE cells in order to further explore the absence of MAC deposition on murine RPE cells following exposure to human serum, and to determine whether the extracellular matrix on the ocular tissues was interfering with accessibility of complement proteins to the RPE or endothelial cell surface. RPE cells were identified by presence of typical pigmentation, characteristic morphology and routine immunostaining for the RPE cell marker, RPE65 (FIG. 7; top row shows bright field illuminated cells, third row shows staining with anti-RPE65). As with tissues, weak and inconsistent MAC immunostaining was observed on passage 0 mouse RPE cells upon exposure to 50% NHS (FIG. 8 panel C).

The absence of extensive MAC deposition on the RPE and corneal endothelium upon exposure to NHS could be due to inefficient complement activation and/or enhanced protection by murine complement regulatory proteins expressed on the surface of these cells. To determine if complement activation on murine RPE could be enhanced, an antibody against the extracellular domain of mouse emmprin, which is an abundantly expressed membrane protein on RPE as well as corneal endothelium was next used. An anti-mouse emmprin antibody produced in goat was selected to avoid potential cross-reactivity with the secondary antibody (Cy3-conjugated goat anti-mouse IgG and IgM) used for MAC immunostaining.

Incubation of mouse eyecup tissues or cornea tissues with the anti-mouse emmprin antibody followed by exposure to NHS (final concentration 50% for 15 minutes eyecup tissues, or 20 minutes cornea tissues at 37° C.) yielded extensive, bright MAC immunostaining of the RPE dissected tissue (FIG. 9 panel A) and corneal endothelium (FIG. 9 panel C). This immunostaining was a result of complement-activated MAC deposition, as addition of control HI-NHS rather than NHS, eliminated the staining: MAC immunostaining was not observed with use of HI-NHS (FIG. 9 panels B and D). The RPE monolayer contacted with NHS often appeared convoluted and various patterns of staining were observed due to different amounts of MAC deposition and various amounts of cell damage. Additional negative controls included MAC immunostaining of eyecup tissues and cornea tissues contacted with the anti-mouse emmprin antibody, but not with human serum as well as omission of the primary antibody during immunohistochemistry of eyecup tissues and cornea tissues contacted with both the anti-mouse emmprin antibody and NHS, and no staining was observed with these controls.

Similar results were also obtained with primary passage 0 mouse RPE cells (FIG. 8 panels A and B). Upon incubation with the anti-emmprin antibody and exposure to 50% NHS for 4 minutes, cell destruction was observed on the RPE cells (FIG. 8 panel A). By 7 minutes of NHS exposure, almost all cells had detached from the slide. Occasionally only cell aggregates of high confluence areas remained (FIG. 8 panel A). Only minimal staining was observed of the control HI-NHS exposed cells (FIG. 8 panel B).

Example 14

Complement-Mediated Vesiculation of RPE Cell Membranes

To further investigate the effects of MAC deposition and protection, primary (passage 0) mouse RPE cells were pretreated with either a mixture of AdCAGCD59+AdCAGGFP (800+200 vp/cell respectively) or with a control mixture of AdEMPTY+AdCAGGFP (800+200 vp/cell respectively). After 7 minutes of NHS treatment, washing and fixation, cells were examined. Three days post-treatment, these cells were analyzed by the MAC deposition assay.

Presence of numerous GFP-positive vesicles associated with cells was observed (FIG. 10 panels A and B, arrows). Examination of the cells revealed the presence of numerous GFP-positive vesicles (FIG. 10 panels A and B, arrows). The number and size of these vesicles was substantially greater for cells pretreated with the mixture of AdEMPTY+AdCAGGFP (FIG. 10 panel A) compared to cells pretreated with the mixture of AdCAGCD59+AdCAGGFP (FIG. 10 panel B). This observation indicates that the vesiculation observed herein was a result of MAC deposition. Furthermore, after contacting with NHS, cells pretreated with the mixture of AdEMPTY+AdCAGGFP showed a reduction in GFP fluorescence compared to fluorescence of cells pretreated with the mixture of AdCAGCD59+AdCAGGFP (FIG. 10 panel A compared to panel B). The reduced GFP fluorescence in cells pretreated with the mixture of AdEMPTY+AdCAGGFP was associated with a concomitant increase in diffuse green fluorescence observed outside of these cells, indicating that GFP had leaked from the cells or had diffused across the plasma membrane in these control cells.

Example 15

Protection of Ocular Tissues and Primary RPE Cells from MAC Deposition by Adenovirus Delivered hCD59

Efficacy of hCD59 pretreatment to protect murine RPE from human MAC deposition was assessed. Mice were administered in vivo subretinal injections of each adenovirus vector. Six days after injection, expression of hCD59 on murine RPE following subretinal injection of the AdCAGCD59 vector was observed by immunohistochemistry with anti-hCD59 antibody (FIG. 11 panel A). Staining for hCD59 was not observed in eyecup tissues that had been injected with the negative control AdCAGGFP (FIG. 11 panel B; top row). Rather, GFP fluorescence was visible at the site of injection (FIG. 11 panel B; bottom row)

For the MAC deposition assay, subretinal injections were performed in two groups of mice. Mice in one group were injected with a mixture of AdCAGCD59 and AdCAGGFP vectors in a 9:1 ratio (AdCAGGFP was co-injected to allow easy identification of the injection site and area of transgene expression by spontaneous fluorescence). Mice from the second group were injected with a control mixture of AdEMPTY and AdCAGGFP (negative controls) also in a 9:1 ratio. Six days after injection, eyes were harvested and eyecup tissues were exposed to anti-mouse emmprin and NHS, along with eyecup tissues from uninjected control mice.

Immunohistochemistry for human MAC of eyecup tissues injected with the mixture of AdCAGCD59 and AdCAGGFP (n=10) showed significantly reduced staining on the RPE at the area of GFP expression (which was used to identify and was found to correlate with hCD59 expression) compared to the uncontacted remaining area of eyecup tissue (FIG. 12 panel B, compare dissected tissues on top row). The RPE cells at this area appeared undamaged with defined cell boundaries and normal hexagonal morphology (FIG. 12 panel B, compare photomicrograph of cells with those in FIG. 12 panel A). In contrast, MAC immunostaining at the GFP expressing area of tissues injected with negative control vectors (mixture of AdEMPTY and AdCAGGFP vectors) of the injected eyecup tissues (n=10) was similar to the uncontacted remaining area of the eyecup tissue (FIG. 12 panel A), and, MAC immunostaining was significantly more extensive and stronger than the MAC immunostaining observed at the area of GFP expression of eyecup tissues injected with the mixture of AdCAGCD59 and AdCAGGFP. Further, the RPE cells at the GFP expressing area of negative control injected eyecup tissues appeared extensively damaged as indicated by their rounded shape, loss of normal hexagonal morphology and loss of defined cell boundaries (FIG. 12 panel A, photomicrographs compared to those in FIG. 12 panel B).

Quantification of the MAC immunofluorescence at the area of GFP expression revealed an overall reduction of ~55% in mean MAC immunofluorescence intensity on the eyecup tissues injected with the mixture of AdCAGCD59 and AdCAG-GFP (n=10) compared to eyecup tissues injected with the mixture of the negative control (n=10), a difference which was statistically significant (p=0.0014, FIG. 13 panel A). These calculations showed that mean MAC fluorescence intensity on the eyecup tissues injected with the mixture of AdCAGCD59 and AdCAGGFP was increased by the lack of significant protection from MAC deposition for only a few eyecup tissues with poor hCD59 expression as indicated by GFP expression, and the figure of 55% was affected by inclusion of these samples. It was observed that there was an inverse relationship between the GFP and MAC fluorescence intensities (FIG. 13 panel B) on the eyecup tissues that had been pretreated with the mixture of AdCAGCD59 and AdCAGGFP. This inverse relationship indicates that a potential therapeutic method involving expression of CD59 can protect tissues from MAC deposition.

Eyecups were then pretreated with mixtures of each of AdEMPTY and AdCAGGFP, and with AdCAGCD59 and AdCAGGFP to analyze the possibility that reduced MAC was a function of transduction of the vector. No significant difference was observed in results between the two groups (n=10 per group) in GFP levels (FIG. 13 panel B). The RPE cell morphology in the AdEMPTY and AdCAGGFP-pretreated eyecups and the AdCAGCD59 and AdCAGGFP-pretreated eyecups were similar (FIG. 12 panels D and E). Further, MAC staining of the AdEMPTY and AdCAGGFP-pretreated eyecups was significantly greater than that of the AdCAGCD59 and AdCAGGFP-pretreated eyecups (FIG. 12 panels D and E).

Quantification of reduction in MAC immunofluorescence at the area of GFP expression revealed an average of about 68% (p=0.0018) at 7.5 min NHS treatment and 56%) (p=0.0007) at 15 min NHS treatment on the AdCAGCD59+ AdCAGGFP-pretreated eyecups compared to AdEMPTY+ AdCAGGFP-pretreated eyecups (FIG. 12 panel C). Moreover, an inverse relationship between the GFP and MAC fluorescence intensities on the AdCAGCD59+AdCAGGFP-pretreated eyecups compared to AdEMPTY+AdCAGGFP-pretreated eyecups (FIG. 13 panel B). This further indicates that protection from MAC deposition is a function of the level of hCD59 expression.

It is possible that the difference in MAC deposition between AdCAGCD59 and negative control pretreated eyecup tissues was due to a difference in mouse emmprin expression and/or to a difference in anti-emmprin antibody binding. To evaluate this possibility, immunohistochemistry for mouse emmprin on eyecup tissues pretreated by pretreatment with the mixture of AdCAGCD59 and AdCAGGFP or eyecup tissues pretreated with the negative control (mixture of AdEMPTY+AdCAGGFP) was performed. Anti-mouse emmprin antibody analysis was performed using the same procedure as for the MAC deposition assay, and eyecup tissues were washed fixed and incubated with an appropriate Cy3-conjugated antibody. No differences in emmprin immunofluorescence on the RPE were observed between the area of transgene expression and the rest of the eyecup tissue (FIG. 14 panels A and B) or uninjected control eyecup tissues (control). Further, no differences in emmprin immunofluorescence were observed between the areas of transgene expression of eyecup tissues pretreated with the mixture of AdCAGCD59 and AdCAGGFP compared to negative control pretreated eyecup tissues (FIG. 14 panels A and B). These data clearly show that protection of murine RPE from human MAC deposition was due to the in vivo expression of adenovirus delivered hCD59.

No differences in emmprin immunofluorescence were observed between the areas of transgene expression of the mixture of AdCAGCD59+AdCAGGFP, and in control injected eyecups (FIG. 14 panels A and B and FIG. 15) observed at two magnifications. Similar results were obtained with primary mouse RPE cells (FIG. 16). Passage 0 RPE cells were pretreated with about 500 vp/cell of AdCAGCD59 vector or AdCAGGFP vector, and three days after contacting, cells were contacted with the anti-mouse emmprin antibody followed by exposure to 50% NHS for 4 minutes. Immunohistochemistry showed a significant reduction in MAC immunostaining of cells pretreated with AdCAGCD59 vector compared to cells pre-treated with AdCAGGFP vector (FIG. 16), data for the latter of which MAC immunofluorescence were similar to that for primary mouse RPE cells not contacted with any vector (control).

Primary murine RPE cells pretreated with AdCAGGFP (FIG. 14 panel C) or AdCAGCD59 (FIG. 14 panel D) assayed by immunohistochemistry methods showed that expression of hDC59 resulted in no changes in emmprin expression levels in primary mouse RPE cells.

Protection from MAC deposition was not due to differences in emmprin expression and/or anti-emmprin antibody binding as immunocytochemistry for mouse emmprin revealed no differences between control and AdCAGCD59 pretreated cells. The data described demonstrate the destructive effects of human MAC deposition on the RPE and on primary RPE cells and significant protection of these cells by expression of hCD59.

Example 16

Protection of Corneal Endothelium from MAC Deposition by Vector-Mediated Delivery of hCD59

MAC deposition and protection by adenovirus-delivered hCD59 was further assayed using murine corneal epithelium. Corneal epithelium is easily accessible tissue and cultured, and pretreated with adenovirus and other vectors in vivo and ex vivo. In addition, assays herein using corneal endothelium were shown to be efficient for homogenous transduction of the endothelial cells and efficient measurement of other factors such as agents that affect complement regulators. Investigation of MAC deposition on corneal endothelium is further useful for screening inhibitors of MAC deposition and complements testing in RPE in vitro and in vivo.

Delivery ex vivo of hCD59 to the corneal endothelium was observed herein to significantly protect those cells from human MAC deposition upon further mixing with the anti-mouse emmprin antibody and 50% NHS for 20 minutes (FIG. 17 panel B; see also FIG. 11 panel C). In contrast, delivery of control marker protein GFP failed to protect the corneal endothelium from human MAC deposition (FIG. 17 panel A), which was observed to be similar in extent to MAC deposition on the corneal endothelium of corneas that had not been treated (control; FIG. 9 panel C). GFP expression on the corneal endothelium of NHS contacted corneas appeared fragmented (FIG. 17 panel A), for example due to loss of endothelial cells following damage by deposition of the MAC. This fragmentation was not observed with control corneas not exposed to NHS (FIG. 11 panel D and FIG. 17 panel C). Data showed that protection of corneal endothelium from MAC by AdCAGCD59 was not due to a difference in emmprin expression and/or anti-emmprin antibody binding as immunohistochemistry revealed no differences in emmprin immunostaining on the corneal endothelium pre-treated with each of AdCAGCD59 and control AdCAGGFP (FIG. 17 panels C and D).

Contacting corneas with the anti-mouse emmprin antibody followed by addition of 50% NHS for 20 minutes at 37° C. resulted in extensive, bright MAC immunostaining on the corneal endothelium (FIG. 18 panel A). Minimal staining was observed on the endothelium of 50% HI-NHS treated (for 20 minutes at 37° C.) corneas. To assess efficacy of hCD59 to protect the corneal endothelium from human MAC deposition, corneas were pretreated ex vivo with the AdCAGCD59 or the control AdCAGGFP vectors.

Data showed that expression of hCD59 on the corneal endothelium following ex vivo infection with the AdCAGCD59 was confirmed by immunohistochemistry using the anti-hCD59 antibody, while no staining for hCD59 was observed on control (AdCAGGFP)-pretreated corneas (FIG. 18 panel B). Pretreatment of corneal endothelium with hCD59 significantly protected those cells from human MAC deposition, as data showed a reduction in MAC immunofluorescence intensity of 86% ($p<0.0001$, FIG. 18 panel C) compared to pretreatment with GFP, which failed to protect the corneal endothelium as MAC deposition levels were similar to those on the corneal endothelium of control corneas not pretreated. Moreover, the GFP expression on the corneal endothelium of NHS treated corneas appeared fragmented indicating loss of endothelial cells due to damage by deposition of the MAC. This fragmentation was not observed on AdCAGGFP-pretreated corneas not exposed to NHS (FIG. 18 panels B and D).

The protection from MAC deposition on the corneal endothelium of AdCAGCD59-pretreated corneas was shown not to be due to a difference in emmprin expression and/or anti-emmprin antibody binding, as immunohistochemistry data showed no differences in emmprin immunostaining on the corneal endothelium of each of AdCAGCD59 and AdCAG-GFP-pretreated, and control not pretreated corneas (FIG. 18 panel D).

These data further show that hCD59 pretreatment protects ocular tissues from MAC deposition. Protection on the corneal endothelium was observed to be higher than that of the RPE. Additional factors might affect this protection, such as higher and more homogenous transduction of endothelium of ex vivo pretreated corneas and efficiency of modulators and regulators of serum components, and of other possible agents that affect macular degeneration.

Example 17

Soluble Secreted hCD59 Construct and Human CD59 Expression in Vector-Contacted Cells The CD59 constructs used in examples above was constructed to expression a membrane associated protein through a GPI linker. Human CD59 lacking the sequence coding for the C terminal 26 amino acids, which includes a signal sequence for attachment of the GPI anchor at the nucleotides encoding residue amino acid Asparagine at position 77 was PCR amplified using a forward primer containing an XhoI site (underlined) (5' ccccctcgagtggacaatcacaatggg3'; SEQ ID No: 1) and a reverse primer with an EcoRV site (underlined) (5' taaggagatatcttaattttcaagctgttcgtta3'; SEQ ID No: 3). The reverse primer introduced a stop codon following Asparagine 77 resulting in a sequence that encodes a soluble form of human CD59. The XhoI/EcoRV digested PCR product was cloned into XhoI/EcoRV digested pShCAG and the resulting plasmid pShCAGsCD59 was used to produce the adenovirus AdCAGsCD59 as described herein. Thus, the GPI signal was removed by recombinant methods to obtain a construct that expresses a soluble, secreted version, and analyses were performed to test whether the secreted version might be useful as a therapeutic agent, as it would more readily spread through the retina and confer protection from MAC deposition for cells that were not directly contacted and transduced with a gene transfer vector.

To evaluate this construct, cells were prepared that carry the soluble CD59 construct, either expressed on a plasmid or on an adenovirus, and were grown and expression in medium was determined. FIG. 19 is a photograph of a Western blot. The second channel from the right was the soluble secreted version (with the GPI linker removed) and was labeled AdCAG$_S$CD59/Unfiltered Media on the photograph. The lane shows secretion of a large amount of protein of about 16 KDa. The channel two over to the right of AdCAG$_S$CD59/Unfiltered Media (i.e., AdCAGCD59, first channel on the right) is the non-soluble form of CD59 from an adenovirus. The signal for the membrane bound version was much weaker because the antibody used on this blot detected the soluble form much better than the membrane bound form. Signal strength was only compared between the same peptide forms.

To determine the effect of expression CD59 having no GPI signal, engineered so that soluble secreted CD59 protein spreads extracellularly through the retina and confers protection against MAC deposition on cells that were not directly transduced with a gene transfer vector, the soluble CD59 protein was expressed in retinal cells and in corneas. Thus these cells and tissues were prepared for in vivo testing of the soluble secreted CD59 construct as a potential improved therapeutic agent, to determine whether this construct is even more efficient in remediation of MAC deposition than the membrane-bound form.

Experiments were performed to determine the extent that the soluble secreted CD59 expressing vector protected tissues and cells from cell morphology changes and cell lysis associated with MAC deposition. The soluble secreted CD59 expressing vector was tested also in the a model of wet AMD.

Results from these experiments will be an indication of potential advantages of the soluble form of CD59 as a therapeutic agent for macular degeneration compared to the membrane-bound form. Additional possibilities include use of both the membrane-bound form and the soluble forms under different conditions, or in combination.

What is claimed is:

1. A method for treating age-related macular degeneration (AMD) in a subject, the method comprising administering a composition into an AMD-affected eye in a subject by ocular injection, wherein said composition comprises a nucleic acid encoding a soluble CD59 protein operably linked to a promoter, wherein said administering results in expression and secretion of said soluble CD59 protein by cells of said AMD-affected eye and said expression results in treatment of AMD-affected tissues or cells in said AMD-affected eye.

2. The method according to claim 1, wherein said nucleic acid is in a viral vector or is a naked nucleic acid.

3. The method according to claim 2, wherein the viral vector is derived from a genetically engineered genome of at least one virus selected from the group consisting of adenovirus, adeno-associated virus, a herpesvirus, and a lentivirus.

4. The method according to claim 3, wherein the lentivirus is a retrovirus.

5. The method according to claim 2, wherein said ocular injection is an intra-ocular injection.

6. The method according to claim 1, wherein the AMD is a dry AMD.

7. The method according to claim 1, wherein said ocular injection is selected from the group consisting of subretinal injection, vitreous injection, intra-ocular injection, subconjunctival injection, and subtenon injection.

8. The method according to claim 1, wherein said ocular injection is an injection of the composition to an external layer of said AMD-affected eye.

9. The method according to claim 1, further comprising administering a therapeutic agent to the AMD-affected eye.

10. The method according to claim 1, wherein the therapeutic agent is selected from the group consisting of: anti-tumor, antiviral, antibacterial, anti-mycobacterial, anti-fungal, anti-proliferative and anti-apoptotic.

11. The method according to claim 10, wherein the therapeutic agent is selected from the group consisting of: a growth factor, an anti-inflammatory agent, a vasopressor agent, a collagenase inhibitor, a steroid, a matrix metalloproteinase inhibitor, an ascorbate, an angiotensin, a calreticulin, a tetracycline, a fibronectin, a collagen, a thrombospondin, a transforming growth factors (TGF), a keratinocyte growth factor (KGF), a fibroblast growth factor (FGF), an insulin-like growth factors (IGFs), an IGF binding protein (IGFBP), an epidermal growth factor (EGF), a platelet derived growth factor (PDGF), a neu differentiation factor (NDF), a hepatocyte growth factor (HGF), a vascular endothelial growth factor (VEGF), a heparin-binding EGF (HBEGF), a thrombospondin, a von Willebrand Factor-C, a heparin, a heparin sulfate, and a hyaluronic acid.

12. The method according to claim 1, where the soluble CD59 protein comprises a deletion of the glycosyl phosphatidyl inositol (GPI) anchoring domain.

13. The method according to claim 1, where the AMD-affected tissues or cells are selected from the group consisting of retina, cornea, vitreous humor, and retinal pigment epithelium.

14. The method according to claim 1, wherein the composition comprises a pharmaceutically acceptable carrier.

15. The method according to claim 1, wherein said soluble CD59 protein spreads extracellularly and affects cells not directly transduced with the nucleic acid of said composition.

* * * * *

```
SEQUENCE LISTING

<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: The sequence was designed and synthesized

<400> SEQUENCE: 1
ccccctcgag tggacaatca caatggg                                     27

<210> SEQ ID NO 2
<211> LENGTH: 31
<212> TYPE: DNA
<213> ORGANISM: Artificial Sequence
<220> FEATURE:
<223> OTHER INFORMATION: The sequence was designed and synthesized

<400> SEQUENCE: 2
cccccgatat caacggggag tttgggagaa g                                31

<210> SEQ ID NO 3
<211> LENGTH: 34
<212> TYPE: DNA
<213> ORGANISM: Artificial Sequence
<220> FEATURE:
<223> OTHER INFORMATION: The sequence was designed and sythesized

<400> SEQUENCE: 3
taaggagata tcttaatttt caagctgttc gtta                             34
```